(12) United States Patent
Huang et al.

(10) Patent No.: US 11,766,420 B2
(45) Date of Patent: Sep. 26, 2023

(54) APPLICATION OF PI4KIIIA PROTEIN AND RELATED MEMBRANE PROTEIN COMPLEX IN TREATING ALZHEIMER'S DISEASE

(71) Applicant: Jiangsu Nuo-Beta Pharmaceutical Technology Co., Ltd., Nantong Jiangsu (CN)

(72) Inventors: Fude Huang, Shanghai (CN); Xiao Zhang, Shanghai (CN); Wenan Wang, Shanghai (CN); Le Zhang, Shanghai (CN); Lixiang Jiang, Shanghai (CN); Tong Zhu, Shanghai (CN); Haiyan Liu, Shanghai (CN); Yudong Zhou, Zhejiang (CN); Yang He, Zhejiang (CN); Wanguo Wei, Shanghai (CN)

(73) Assignee: JIANGSU NUO-BETA PHARMACEUTICAL TECHNOLOGY CO. LTD., Nantong (CN)

( * ) Notice: Subject to any disclaimer, the term of this patent is extended or adjusted under 35 U.S.C. 154(b) by 623 days.

(21) Appl. No.: 15/570,681

(22) PCT Filed: May 3, 2016

(86) PCT No.: PCT/CN2016/080907
§ 371 (c)(1),
(2) Date: Jun. 4, 2019

(87) PCT Pub. No.: WO2016/173562
PCT Pub. Date: Nov. 3, 2016

(65) Prior Publication Data
US 2019/0314321 A1 Oct. 17, 2019

(30) Foreign Application Priority Data
Apr. 30, 2015 (WO) ................ PCT/CN2015/078058

(51) Int. Cl.
| | | |
|---|---|---|
| A61K 31/285 | (2006.01) | |
| A61K 31/341 | (2006.01) | |
| A61K 31/343 | (2006.01) | |
| A61K 31/381 | (2006.01) | |
| A61K 31/404 | (2006.01) | |
| A61K 31/42 | (2006.01) | |
| A61K 31/4406 | (2006.01) | |
| A61K 31/47 | (2006.01) | |
| A61K 31/5375 | (2006.01) | |
| A61K 31/538 | (2006.01) | |
| A61K 31/54 | (2006.01) | |
| A61K 38/45 | (2006.01) | |
| A61K 38/00 | (2006.01) | |
| C07K 14/395 | (2006.01) | |
| C07K 14/415 | (2006.01) | |
| C07K 16/12 | (2006.01) | |

(Continued)

(52) U.S. Cl.
CPC .......... *A61K 31/285* (2013.01); *A61K 31/341* (2013.01); *A61K 31/343* (2013.01); *A61K 31/381* (2013.01); *A61K 31/404* (2013.01); *A61K 31/42* (2013.01); *A61K 31/4406* (2013.01); *A61K 31/47* (2013.01); *A61K 31/538* (2013.01); *A61K 31/5375* (2013.01); *A61K 31/54* (2013.01); *A61K 38/45* (2013.01); *C07K 14/395* (2013.01); *C07K 14/415* (2013.01); *C07K 16/1203* (2013.01); *C07K 16/18* (2013.01); *C07K 16/40* (2013.01); *C12Y 207/01067* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 2007/0212717 A1 | 9/2007 | Kukolj et al. | |
| 2010/0035811 A1* | 2/2010 | Kim ..................... | A61K 31/663 514/6.9 |
| 2012/0258967 A1* | 10/2012 | Qiao ........................ | A61P 3/00 514/233.8 |

FOREIGN PATENT DOCUMENTS

| | | |
|---|---|---|
| CN | 101392027 A | 3/2009 |
| CN | 103529182 A | 1/2014 |

(Continued)

OTHER PUBLICATIONS

Bishe "Role of Phosphatidylinositol 4-Phosphate (PI4P) and Its Binding Protein GOLPH3 in Hepatitis C Virus Secretion" The Journal of Biological Chemistry vol. 287, No. 33, pp. 27637-27647, (Year: 2012).*

(Continued)

*Primary Examiner* — Adam Weidner
(74) *Attorney, Agent, or Firm* — Goodwin Procter LLP

(57) ABSTRACT

The use of a genetic method to down-regulate RBO/EFR3/EFR3A/EFR3B proteins, TTC7 protein or PI4KIIIα enzyme protein which interacts with RBO/EFR3/EFR3A/EFR3B proteins and TTC7 protein, or the use of a drug to inhibit PI4KIIIα protein kinase activity reduces the accumulation of A$\beta_{42}$ within neurons and age-dependent synaptic transmission failure and other obstacles in a fruit fly AD model, and obtains an effect of improving the learning and memory abilities of AD model mice. Provided is a method for using an RBO/EFR3/EFR3A/EFR3B inhibitor, a TTC7 inhibitor and a PI4KIIIα inhibitor to treat Alzheimer's disease. Also provided is a method for screening a drug treating Alzheimer's disease by whether Aβ secretion by nerve cells is promoted or not.

5 Claims, 11 Drawing Sheets
Specification includes a Sequence Listing.

(51) Int. Cl.
    C07K 16/18      (2006.01)
    C07K 16/40      (2006.01)

(56)                References Cited

FOREIGN PATENT DOCUMENTS

| WO | WO-2002/043654 A2 | 6/2002 |
| WO | WO-2004/080416 A2 | 9/2004 |
| WO | WO-2006/060753 A2 | 6/2006 |
| WO | WO-2011/031896 A2 | 3/2011 |
| WO | WO-2012/122383    | 9/2012 |
| WO | WO-2012/122383 A2 | 9/2012 |
| WO | WO 2013010218   * | 1/2013 |

OTHER PUBLICATIONS

Gupta "Rare deleterious mutations of the gene EFR3A in autism spectrum disorders" Molecular Autism 2014, 5:31 (Year: 2014).*
Eagle "The Toxicity, Treponemicidal Activity, and Potential Therapeutic Utility of SUBSTItuted phenylarsenoxides" J pharm Experi Thera (Year: 1940).*
Song "Inhibition of beta-AMYLOID1-42 Internalization Attenuates Neuronal Death by Stabilizing the Endosomal-Lysosomal System in Rat Cortical Cultured Neurons"Neuroscience 178 (2011) 181-188 (Year: 2011).*
Reitz "Toward precision medicine in Alzheimer's disease" Ann Transl Med 2016;4(6):107 (Year: 2016).*
Stanford "Alzheimer's Prevention, Treatment and Research -A Q&A with Dr. Frank Longo" accessed from stanfordhealthcare.org on May 3, 2016 (Year: 2016).*
Reardon "Alzheimer's researchers seek better mice" nature 563:611-612 (Year: 2018).*
Drummond "Alzheimer's Disease: Experimental Models and Reality" Acta Neuropathol. Feb. 2017 ; 133(2): 155-175. (Year: 2017).*
Walker "The Exceptional Vulnerability of Humans to Alzheimer's Disease" Trends Mol Med. Jun. 2017 ; 23(6): 534-545. (Year: 2017).*
Franco "Successful therapies for Alzheimer's disease: why so many in animal models and none in humans?" front pharma 5(146):1-13 (Year: 2014).*
Vitek "Translational animalmodels for Alzheimer's disease: An Alzheimer's Association Business Consortium Think Tank" Alzheimer's Dement. 2020;6:e12114. (Year: 2020).*
Balla A, Tuymetova G, Barshishat M, Geiszt M, Balla T. Characterization of type II phosphatidylinositol 4-kinase isoforms reveals association of the enzymes with endosomal vesicular compartments. J Biol Chem. May 31, 2002;277(22):20041-50. Epub Mar. 28, 2002.
Balla, "Phosphatidylinositol 4-kinase, type III, alpha", Nov. 15, 2005, UCSD Nature Molecule Pages (6 pages).
Chen et al., "Protective Effect of Bajijiasu Against b-Amyloid-Induced Neurotoxicity in PC12 Cells", Cellular and Molecular Neurobiology, Jun. 29, 2013 (14 pages).
Chung et al., "Plasticity of PI4KIIIα interactions at the plasma membrane," EMBO Reports, 2015, 16:312-320.
Clayton et al., "Phosphatidylinositol 4-Kinases and PI4P Metabolism in the Nervous System: Roles in Psychiatric and Neurological Diseases", Molecular Neurobioloby, 2013, 47:361-372.
Guerreiro et al., "A Sensitized RNA Interference Screen Identifies a Novel Role for the PI3K p110γ Isoform in Medulloblastoma Cell Proliferation and Chemoresistance", Molecular Cancer Research, Jul. 2011 9(7):925-936.
Harak et al., "Mapping of Functional Domans of the Lipid Kinase Phosphatidylinositol 4-Kinase Type III Alpha Involved in Enzymatic Activity and Hepatitis C Virus Replication", Journal of Virology, Sep. 2014, 88(17): 9909-9926.
Haugabook, et al., "Reduction of AB accumulation in the Tg2576 animal model of Alzheimer's disease after oral administration of the phosphatidylinositol kinase inhibitor wortmannin", The FASEB Journal, Nov. 9, 2000 (12 pages).

International Search Report for International Patent Application No. PCT/CN2016/080907 dated Jul. 21, 2016 (5 pages).
Kuboyama, et al., "Inhibition of clathrin-mediated endocystosis prevents amyloid B-induced axonal damage", Neurobiology of Aging, 2015, 36:1808-1819.
Lee, "Roles of Phosphoinositides and Phosphoinositides Kinases in Hepatitis C Virus RNA Replication", Arch Pharm Res, 2012, 35(10):1701-1711.
Nagele et al., "Intracellular Accumulation of β-Amyloid$_{1-42}$ in Neurons Is Facilitated by the α7 Nicotinic Acetylcholine Receptor in Alzheimer's Disease", Neurscience, 2002, 110(2):199-211.
Nakatsu, et al., "PtdIns4P synthesis by PI4KIIIα lot at the plasma membrane and its impact on plasma membrane identity", The Journal of Cell Biology, Dec. 2012, 199(6):1003-1016.
Cai et al., (2013), "Rapamycin, Autophagy, and Alzheimer's Disease," *J Biochem Pharmacol Res.*, 1(2):84-90.
Dickson et al., (2014), "Golgi and plasma membrane pools of PI(4)P contribute to plasma membrane PI(4,5)P2 and maintenance of KCNQ2/3 ion channel current," *Proc Natl Acad Sci U S A.*, 2014;111(22):E2281-E2290.
McIntire et al., (2014), "Screening assay for small-molecule inhibitors of synaptojanin 1, a synaptic phosphoinositide phosphatase.," *J Biomol Screen.*, 19(4):585-594.
Avdesh et al., Memory function in a mouse genetic model of Alzheimer's disease. J Alzheimers Dis. 2011 ;25(3):433-44. doi: 10.3233/JAD-2011-101944. Pmid: 21460433.
Berman et al., Oligomeric amyloid-beta peptide disrupts phosphatidylinositol-4,5-bisphosphate metabolism. Nat Neurosci. May 2008;11(5):547-54. doi: 10.1038/nn.2100. Epub Apr. 6, 2008. PMID: 18391946; Pmcid: PMC2532986.
Bu, Apolipoprotein E and its receptors in Alzheimer's disease: pathways, pathogenesis and therapy. Nat Rev Neurosci. May 2009;10(5):333-44. doi: 10.1038/nrn2620. Epub Apr. 2, 2009. PMID: 19339974; Pmcid: PMC2908393.
Chen et al., Multiple forms of dynamin are encoded by shibire, a Drosophila gene involved in endocytosis. Nature. Jun. 1, 19913;351(6327):583-6. doi: 10.1038/351583a0. PMID: 1828536.
Di Paolo et al., Decreased synaptic vesicle recycling efficiency and cognitive deficits in amphiphysin 1 knockout mice. Neuron. 2002 Feb. 28;33(5):789-804. doi: 10.1016/s0896-6273(02)00601-3. PMID: 11879655.
Fa et al., Dynamin 1 is required for memory formation. PLoS One. Mar. 1, 20148;9(3):e91954. doi: 10.1371/journal.pone.0091954. PMID: 24643165; Pmcid: PMC3958425.
Frost et al., Uptake and binding of radiolabelled phenylarsine oxide in 3T3-L1 adipocytes. Biochem J. Aug. 1, 1990;269(3):589-95. doi: 10.1042/bj2690589. PMID: 2202293; Pmcid: PMC1131627.
Fuentealba et al., Low-density lipoprotein receptor-related protein 1 (LRP1) mediates neuronal Abeta42 uptake and lysosomal trafficking. PLoS One. Jul. 2, 20109;5(7):e11884. doi: 10.1371/iournal.pone.0011884. PMID: 20686698; Pmcid: PMC2912373.
Gibson et al., Phenylarsine oxide inhibition of endocytosis: effects on asialofetuin internalization. Am J Physiol. Aug. 1989;257(2 Pt 1):C182-4. doi: 10.1152/ajpcell.1989.257.2.C182. PMID: 2475026.
Harold et al., Genome-wide association study identifies variants at CLU and PICALM associated with Alzheimer's disease. Nat Genet. Oct. 2009;41(10):1088-93. doi: 10.1038/ng.440. Epub Sep. 6, 2009. Erratum in: Nat Genet. Oct. 2009;41(10):1156. Erratum in: Nat Genet. Jun. 2013;45(6):712. Haun, Reinhard [added]. PMID: 19734902; Pmcid: PMC2845877.
Jiang et al., TREM2 modifies microglial phenotype and provides neuroprotection in P301S tau transgenic mice. Neuropharmacology. Jun. 2016;105:196-206. doi: 10.1016/j.neuropharm.2016.01.028. Epub Jan. 2, 20161. PMID: 26802771.
Jiang et al., Upregulation of TREM2 ameliorates neuropathology and rescues spatial cognitive impairment in a transgenic mouse model of Alzheimer's disease. Neuropsychopharmacology. Dec. 2014;39(13):2949-62. doi: 10.1038/npp.2014.164. Epub Jul. 2, 20142. PMID: 25047746; Pmcid: PMC4229581.
Kanekiyo et al., Neuronal clearance of amyloid-p by endocytic receptor LRP1. J Neurosci. Dec. 4, 2013;33(49):19276-83. doi: 10.1523/JNEUROSCI.3487-13.2013. Pmid: 24305823; Pmcid: PMC3850043.

(56) References Cited

OTHER PUBLICATIONS

Korge et al., Phenylarsine oxide induces mitochondrial permeability transition, hypercontracture, and cardiac cell death. Am J Physiol Heart Circ Physiol. May 2001;280(5):H2203-13. doi: 10.1152/ajpheart.2001.280.5.H2203. PMID: 11299223.

Lambert et al., Is there a relation between APOE expression and brain amyloid load in Alzheimer's disease? J Neurol Neurosurg Psychiatry. Jul. 2005;76(7):928-33. doi: 10.1136/jnnp.2004. 048983. PMID: 15965197; Pmcid: PMC1739723.

Liu et al., APOE4 enhances age-dependent decline in cognitive function by down-regulating an NMDA receptor pathway in EFAD-Tg mice. Mol Neurodegener. 2015 Mar5;10:7. doi: 10.1186/s13024-015-0002-2. PMID: 25871877; Pmcid: PMC4391134.

Liu Q et al., Neuronal LRP1 knockout in adult mice leads to impaired brain lipid metabolism and progressive, age-dependent synapse loss and neurodegeneration. J Neurosci. Dec. 1, 20105;30(50):17068-78. doi: 10.1523/JNEUROSCI.4067-10.2010. Pmid: 21159977; Pmcid: PMC3146802.

McIntire et al., Reduction of synaptojanin 1 ameliorates synaptic and behavioral impairments in a mouse model of Alzheimer's disease. J Neurosci. Oct. 3, 20121;32(44):15271-6. doi: 10.1523/JNEUROSCI.2034-12.2012. Pmid: 23115165; Pmcid: PMC3711720.

Metzler et al., Disruption of the endocytic protein HIP1 results in neurological deficits and decreased AMPA receptor trafficking. Embo J. Jul. 1, 2003 ;22(13):3254-66. doi: 10.1093/emboj/cdg334. PMID: 12839988; Pmcid: PMC165658.

Moreno-Ortega AJ et al., Cano-Abad MF. Neuroprotective Effect of the Novel Compound ITH33/IQM9.21 Against Oxidative Stress and Na(+) and Ca(2+) Overload in Motor Neuron-like NSC-34 Cells. Neurotox Res. Oct. 2016;30(3):380-91. doi: 10.1007/s12640-016-9623-7. Epub Apr. 2, 20168. PMID: 27126806.

Neniskyte et al., Death induced by nanomolar amyloid 3 is mediated by primary phagocytosis of neurons by microglia. J Biol Chern. Nov. 1, 20118;286(46):39904-13. doi: 10.1074/jbc.M111.267583. Epub Sep. 8, 2011. PMID: 21903584; Pmcid: PMC3220594.

Pettengell et al., Effect of phenylarsine oxide on protein synthesis in 3T3-L1 adipocytes. Biochem Biophys Res Commun. Jun. 1, 19895;161(2):633-9. doi: 10.1016/0006-291 x(89)92646-6. PMID: 2735914.

Randall et al., functional neurophysiology of the amyloid precursor protein (APP) processing pathway. Neuropharmacology. Sep. 2010-Oct. 59(4-5):243-67. doi: 10.1016/j.neuropharm.2010.02.011. Epub Feb. 1, 20106. PMID: 20167227.

Regeur et al., No. global neocortical nerve cell loss in brains from patients with senile dementia of Alzheimer's type. Neurobiol Aging. May 1994-Jun. 15(3):347-52. doi: 10.1016/0197-4580(94)90030-2. PMID: 7936059.

Roth, Caspases, apoptosis, and Alzheimer disease: causation, correlation, and confusion. J Neuropathol Exp Neurol. Sep. 2001;60(9):829-38. doi: 10.1093/jnen/60.9.829. PMID: 11556539.

Sabbagh et al., PF-04494700, an oral inhibitor of receptor for advanced glycation end products (RAGE), in Alzheimer disease. Alzheimer Dis Assoc Disord. Jul. 2011-Sep. 25(3):206-12. doi: 10.1097/WAD.0b013e318204b550. PMID: 21192237; Pmcid: PMC3346183.

Searl et al., The phosphatidylinositol 4-kinase inhibitor phenylarsine oxide blocks evoked neurotransmitter release by reducing calcium entry through N-type calcium channels. Br J Pharmacol. May 2000;130(2):418-24. doi: 10.1038/sj.bjp.0703299. PMID: 10807681; Pmcid: PMC1572064.

Selkoe, Translating cell biology into therapeutic advances in Alzheimer's disease. Nature. Jun. 2, 19994;399(6738 Suppl):A23-31. doi: 10.1038/399a023. PMID: 10392577.

Song et al., Memantine protects rat cortical cultured neurons against beta-amyloid-induced toxicity by attenuating tau phosphorylation. Eur J Neurosci. Nov. 2008;28(10):1989-2002. doi: 10.1111/j.1460-9568.2008.06498.x. PMID: 19046381.

Song et al., Lipoprotein-based nanoparticles rescue the memory loss of mice with Alzheimer's disease by accelerating the clearance of amyloid-beta. ACS Nano. Mar. 2, 20145;8(3):2345-59. doi: 10.1021/nn4058215. Epub Feb. 2, 20141. PMID: 24527692.

Terry et al., Physical basis of cognitive alterations in Alzheimer's disease: synapse loss is the major correlate of cognitive impairment. Ann Neurol. Oct. 1991;30(4):572-80. doi: 10.1002/ana.410300410. PMID: 1789684.

Verstreken et al., mutations block clathrin-mediated endocytosis but not neurotransmitter release. Cell. Apr. 5, 2002;109(1 ):101-12. doi: 10.1016/s0092-8674(02)00688-8. PMID: 11955450.

Wang et al., TREM2 lipid sensing sustains the microglial response in an Alzheimer's disease model. Cell. Mar. 1, 20152;160(6):1061-71. doi: 10.1016/j.cell.2015.01.049. Epub Feb. 2, 20156. PMID: 25728668; Pmcid: PMC4477963.

Xue et al., A multifunctional peptide rescues memory deficits in Alzheimer's disease transgenic mice by inhibiting Ap42-induced cytotoxicity and increasing microglial phagocytosis. Neurobiol Dis. Jun. 2012;46(3):701-9. doi: 10.1016/j.nbd.2012.03.013. Epub 2012 Mar9. PMID: 22426388.

Yao et al., Changes in synaptic expression of clathrin assembly protein AP180 in Alzheimer's disease analysed by immunohistochemistry. Neuroscience. 1999;94(2):389-94. doi: 10.1016/s0306-4522(99)00360-7. PMID: 10579202.

Yao et al., Defects in expression of genes related to synaptic vesicle trafficking in frontal cortex of Alzheimer's disease. Neurobiol Dis. Mar. 2003;12(2):97-109. doi: 10.1016/s0969-9961 (02)00009-8. PMID: 12667465.

Yeh et al., TREM2 Binds to Apolipoproteins, Including APOE and CLU/APOJ, and Thereby Facilitates Uptake of Amyloid-Beta by Microglia. Neuron. Jul. 2, 20160;91 (2):328-40. doi: 10.1016/j.neuron.2016.06.015. PMID: 27477018.

Yoo et al., Reduction of dynamin 1 in the hippocampus of aged mice is associated with the decline in hippocampal-dependent memory. Mol Med Rep. Nov. 2016;14(5):4755-4760. doi: 10.3892/mmr.2016. 5804. Epub Oct. 5, 2016. PMID: 27748822.

Yue et al., Inhibition of phosphatidylinositol 4-kinase results in a significant reduced respiratory burst in formyl-methionyl-leucyl-phenylalanine-stimulated human neutrophils. J Biol Chern. Dec. 2, 20018;276(52):49093-9. doi: 10.1074/jbc.M101328200. Epub Oct. 9, 2001. PMID: 11592957.

Zhao et al., Central role for PICALM in amyloid-p blood-brain barrier transcytosis and clearance. Nat Neurosci. Jul. 2015;18(7):978-87. doi: 10.1038/nn.4025. Epub May 2, 20155. PMID: 26005850; Pmcid: PMC4482781.

Zhao et al., Expression of beta-amyloid induced age-dependent presynaptic and axonal changes in Drosophila. J Neurosci. Jan. 2, 20107;30(4):1512-22. doi: 10.1523/JNEUROSCI.3699-09.2010. Pmid: 20107079; Pmcid: PMC6633795.

Zhu et al., Reduction of synaptojanin 1 accelerates A clearance and attenuates cognitive deterioration in an Alzheimer mouse model. J Biol Chern. Nov. 1, 2013 ;288(44):32050-63. doi: 10.1074/jbc. M113.504365. Epub Sep. 1, 20139. PMID: 24052255; Pmcid: PMC3814799.

Al-Ramahi, Ismael et al. "Inhibition of PIP4Kγ ameliorates the pathological effects of mutant huntingtin protein." *eLife* vol. 6 e29123. Dec. 26, 2017, doi:10.7554/eLife.29123.

Baskys, Andrius et al. "Rab-mediated endocytosis: linking neurodegeneration, neuroprotection, and synaptic plasticity?." *Annals of the New York Academy of Sciences* vol. 1122 (2007): 313-29. doi:10.1196/annals.1403.023.

Batarseh, Yazan S et al. "Amyloid-β and Astrocytes Interplay in Amyloid-β Related Disorders," *International journal of molecular sciences* vol. 17,3 338. Mar. 4, 2016, doi:10.3390/ijms17030338.

Bateman, Randall J et al. "Clinical and biomarker changes in dominantly inherited Alzheimer's disease." *The New England journal of medicine* vol. 367,9 (2012): 795-804. doi:10.1056/NEJMoa1202753.

Begum, N. "Phenylarsine oxide inhibits insulin-stimulated protein phosphatase 1 activity and GLUT-4 translocation." *The American journal of physiology* vol. 267,1 Pt 1 (1994): E14-23. doi:10.1152/ajpendo.1994.267.1.E14.

Bitoun, Marc et al. "Mutations in dynamin 2 cause dominant centronuclear myopathy," *Nature genetics* vol. 37,11 (2005): 1207-9. doi:10.1038/ng1657.

(56) References Cited

OTHER PUBLICATIONS

Boumil, Rebecca M et al. "A missense mutation in a highly conserved alternate exon of dynamin-1 causes epilepsy in fitful mice." *PLoS genetics* vol. 6,8 e1001046. Aug. 5, 2010, doi:10.1371/journal.pgen.1001046.

Carrillo-Mora, Paul et al. "Amyloid beta: multiple mechanisms of toxicity and only some protective effects?." *Oxidative medicine and cellular longevity* vol. 2014 (2014): 795375. doi:10.1155/2014/795375.

Coussens, C M et al. "Tyrosine phosphorylation-dependent inhibition of hippocampal synaptic plasticity." *Neuropharmacology* vol. 39,12 (2000): 2267-77. doi:10.1016/s0028-3908(00)00087-3.

De Camilli, P et al. "Phosphoinositides as regulators in membrane traffic." *Science (New York, N.Y.)* vol. 271,5255 (1996): 1533-9. doi:10.1126/science.271.5255.1533.

Douen, A G, and M N Jones. "The action of phenylarsine oxide on the stereospecific uptake of D-glucose in basal and insulin-stimulated rat adipocytes." *Biochimica et biophysica acta* vol. 968,1 (1988): 109-18. doi:10.1016/0167-4889(88)90050-x.

Drouet, Valérie, and Suzanne Lesage. "Synaptojanin 1 mutation in Parkinson's disease brings further insight into the neuropathological mechanisms." *BioMed research international* vol. 2014 (2014): 289728. doi:10.1155/2014/289728.

Dutta, Dipannita, and Julie G Donaldson. "Search for inhibitors of endocytosis: Intended specificity and unintended consequences." *Cellular logistics* vol. 2,4 (2012): 203-208. doi:10.4161/cl.23967.

Ferguson, Shawn M, and Pietro De Camilli. "Dynamin, a membrane-remodelling GTPase." *Nature reviews. Molecular ceil biology* vol. 13,2 75-88. Jan. 11, 2012, doi:10.1038/nrm3266.

Foley, Timothy D et al. "Oxidative inhibition of protein phosphatase 2A activity: role of catalytic subunit disulfides." *Neurochemical research* vol. 32,11 (2007): 1957-64. doi:10.1007/s11064-007-9394-x.

Giuffrida, Maria Laura et al. "Beta-amyloid monomers are neuroprotective." *The Journal of neuroscience : the official journal of the Society for Neuroscience* vol. 29,34 (2009): 10582-7. doi:10.1523/JNEUROSCI.1736-09.2009.

Gouras, Gunnar K et al. "Intraneuronal beta-amyloid accumulation and synapse pathology in Alzheimer's disease." *Acta neuropathologica* vol. 119,5 (2010): 523-41. doi:10.1007/s00401-010-0679-9.

Jacobsen, J Steven et al. "Current concepts in therapeutic strategies targeting cognitive decline and disease modification in Alzheimer's disease." *NeuroRx : the journal of the American Society for Experimental NeuroTherapeutics* vol. 2,4 (2005): 612-26. doi:10.1602/neurorx.2.4.612.

Jenkins, S M, and G V Johnson. "Microtubule/MAP-affinity regulating kinase (MARK) is activated by phenylarsine oxide in situ and phosphorylates tau within its microtubule-binding domain." *Journal of neurochemistry* vol. 74,4 (2000): 1463-8. doi:10.1046/j.1471-4159.2000.0741463.

Krebs, Catharine E et al. "The Sac1 domain of SYNJ1 identified mutated in a family with early-onset progressive Parkinsonism with generalized seizures." *Human mutation* vol. 34,9 (2013): 1200-7. doi:10.1002/humu.22372.

Lee, V M et al. "Neurodegenerative tauopathies." *Annual review of neuroscience* vol. 24 (2001): 1121-59. doi:10.1146/annurev.neuro.24.1.1121.

Li, J et al. "Phenylarsine oxide and vanadate: apparent paradox of inhibition of protein phosphotyrosine phosphatases in rat adipocytes." *Biochimica et biophysica acta* vol. 1312,3 (1996): 223-30. doi:10.1016/0167-4889(96)00038-9.

Liu, Fei et al. "Dephosphorylation of tau by protein phosphatase 5: impairment in Alzheimer's disease." *The Journal of biological chemistry* vol. 280,3 (2005): 1790-6. doi:10.1074/jbc.M410775200.

Mattsson, Niklas et al. "CSF biomarkers and incipient Alzheimer disease in patients with mild cognitive impairment." *JAMA* vol. 302,4 (2009): 385-93. doi:10.1001/jama.2009.1064.

Pei, J J et al., "Subcellular distribution of protein phosphatases and abnormally phosphorylated tau in the temporal cortex from Alzheimer's disease and control brains," *Journal of neural transmission (Vienna, Austria : 1996)* vol. 105,1 (1998): 69-83. doi:10.1007/s007020050039.

Plant, Leigh D et al. "The production of amyloid beta peptide is a critical requirement for the viability of central neurons." *The Journal of neuroscience : the official journal of the Society for Neuroscience* vol. 23,13 (2003): 5531-5. doi:10.1523/JNEUROSCI.23-13-05531.2003.

Retta, S F et al. "Focal adhesion and stress fiber formation is regulated by tyrosine phosphatase activity." *Experimental cell research* vol. 229,2 (1996): 307-17. doi:10.1006/excr.1996.0376.

Schmidt, A et al. "Protein-tyrosine phosphatase activity regulates osteoclast formation and function: inhibition by alendronate." *Proceedings of the National Academy of Sciences of the United States of America* vol. 93,7 (1996): 3068-73. doi:10.1073/pnas.93.7.3068.

Selkoe, Dennis J. "Alzheimer's disease is a synaptic failure," *Science (New York, N.Y.)* vol. 298,5594 (2002): 789-91. doi:10.1126/science.1074069.

Selkoe, Dennis J, and John Hardy. "The amyloid hypothesis of Alzheimer's disease at 25 years." *EMBO molecular medicine* vol. 8,6 595-608. Jun. 1, 2016, doi:10.15252/emmm.201606210.

Sims, Rebecca et al. "Rare coding variants in PLCG2, ABI3, and TREM2 implicate microglial-mediated innate immunity in Alzheimer's disease." *Nature genetics* vol. 49,9 (2017): 1373-1384. doi:10.1038/ng.3916.

Sontag, Jean-Marie, and Estelle Sontag. "Protein phosphatase 2A dysfunction in Alzheimer's disease." *Frontiers in molecular neuroscience* vol. 7 16. Mar. 11, 2014, doi:10.3389/fnmol.2014.00016.

Sowell, M O et al. "Phenylarsine oxide and denervation effects on hormone-stimulated glucose transport." *The American journal of physiology* vol. 255,2 Pt 1 (1988): E159-65. doi:10.1152/ajpendo.1988.255.2.E159.

Sunderland, Trey et al. "Decreased beta-amyloid1-42 and increased tau levels in cerebrospinal fluid of patients with Alzheimer disease." *JAMA* vol. 289,16 (2003): 2094-103, doi:10.1001/jama.289.16.2094.

Tarasenko, A S et al, "Phenylarsine oxide is able to dissipate synaptic vesicle acidic pool." *Neurochemistry international* vol. 46,7 (2005): 541-50. doi:10.1016/j.neuint.2005.02.004.

Zhu, Li et al. "Phospholipid dysregulation contributes to ApoE4-associated cognitive deficits in Alzheimer's disease pathogenesis." *Proceedings of the National Academy of Sciences of the United States of America* vol. 112,38 (2015): 11965-70. doi:10.1073/pnas.1510011112.

Züchner, Stephan et al. "Mutations in the pleckstrin homology domain of dynamin 2 cause dominant intermediate Charcot-Marie-Tooth disease." *Nature genetics* vol. 37,3 (2005): 289-94. doi:10.1038/ng1514.

Malek, Adel M et al. "Hypertonicity triggers RhoA-dependent assembly of myosin-containing striated polygonal actin networks in endothelial cells." *American journal of physiology. Ceil physiology* vol. 292,5 (2007): C1645-59. doi:10.1152/ajpcell.00533.2006.

Doussiere, J et al. "Phenylarsine oxide as an inhibitor of the activation of the neutrophil NADPH oxidase—identification of the beta subunit of the flavocytochrome b component of the NADPH oxidase as a target site for phenylarsine oxide by photoaffinity labeling and photoinactivation." *European journal of biochemistry* vol. 251,3 (1998): 649-58.

McCrea, Heather J, and Pietro De Camilli. "Mutations in phosphoinositide metabolizing enzymes and human disease." *Physiology (Bethesda, Md.)* vol. 24 (2009): 8-16.

\* cited by examiner

APPLICATION OF PI4KIIIA PROTEIN AND RELATED MEMBRANE PROTEIN COMPLEX IN TREATING ALZHEIMER'S DISEASE

CROSS-REFERENCE TO RELATED APPLICATIONS

This application is a U.S. National Stage Application filed under 35 U.S.C. § 371 of International Patent Application No. PCT/CN2016/080907, filed May 3, 2016, which claims priority to and the benefit of PCT/CN2015/078058, filed Apr. 30, 2015, the entire disclosures of each of which are incorporated by reference herein in their entireties.

STATEMENT ON FUNDED RESEARCH

This invention was ever supported by the 973 programs of Ministry of Science and Technology (Grant Nos. 2013CB530900 and 2011CBA00408), by the National Natural Science Foundation (Grant Nos. 81371400, 81071026 and 81571101), and by Shanghai fundamental major program (Grant No. 06dj 14010) of China.

SEQUENCE LISTING

The instant application contains a Sequence Listing which has been submitted electronically in ASCII format and is hereby incorporated by reference in its entirety. Said ASCII copy, created on Jun. 20, 2019, is named JNB-002_SL.txt and is 4,096 bytes in size.

TECHNICAL FIELD

The present invention belongs to the field of medicine specifically, relates to a method for the down-regulation of PI4KIIIα kinase and membrane protein complexes thereof formed with RBO/EFR3/EFR3A/EFR3B protein and TTC7 protein using related inhibitors so as to treat Alzheimer's disease. In another aspect the present invention relates to a method for screening medicines and therapeutic targets for the treatment of Alzheimer's disease according to whether Aβ secretion from cells is facilitated or not.

BACKGROUND

Alzheimer's disease (AD) is the most common neurodegenerative disease in elderly people, characterized in by a progressive loss of learning and memory abilities. Synaptic dysfunction and loss occurs in the early stages of AD which is widely recognized as a major cellular mechanism of learning and memory dysfunction in AD wherein accumulation of Aβ (particularly $A\beta_{42}$) plays an important role. Although a variety of clinical trials on compounds or molecules intended for inhibiting Aβ production and for enhance Aβ clearance were conducted, it is not yet to find a compound or molecule that may improve learning and memory or prevent the further deterioration of learning and memory dysfunction. One possible explanation is that these medicines or treatment methods failed to change the key pathogenesis causing learning and memory dysfunction of AD. More deep understanding is required in all aspects of Aβ accumulation in AD.

Aβ not only accumulates in extracellular space, but also accumulates in neurons. Mounting evidences suggest that Aβ accumulates within various intracellular organs in neuron, and participates in AD pathogenesis changes such as synaptic deficits, amyloid plaque formation, neuronal death and the like. In addition, oligomeric Aβ, which is believed to be the most deleterious effect on synaptic and cognitive functions, forms intracellularly and accumulates in brain neurons or cell membranes of AD patients and APP transgenic mice. Such membrane-associated Aβ may reside on cell membrane of neurons or membrane of intracellular organs. There are certain possibilities that may result in neuronal Aβ accumulation, e.g., endocytosis of extracellular Aβ, retention caused by reduced secretion of intracellularly generated Aβ, Aβ production and accumulation in autophagosome, and reduction of intracellular Aβ degradation.

Although Aβ accumulates both intra- and extracellularly, $A\beta_{42}$ concentration in cerebrospinal fluid (CSF) of AD patients or early stage AD patients are reduced by about half of control population. In AD model mice, $A\beta_{42}$ concentration in cerebrospinal fluid and brain interstitial fluid (ISF) shows an age-dependent reduction, while Aβ dimers are not detectable in ISF. It is presumed that the reduction of $A\beta_{42}$ concentration in CSF is possibly caused by the sequestering effect of extracellular amyloid plaque, decline of $A\beta_{42}$ secretion, and $A\beta_{42}$ accumulation in neurons or cerebral cell membranes.

Studies have demonstrated that phospholipids and their metabolizing enzymes may contribute to AD pathogenesis via its interaction with Aβ or participation in AD-related changes through various cellular and molecular processes, including: 1) $A\beta_{42}$ insert into lipid membrane and bind to acidic phospholipids, which in turn induces the conversion of random coil into β-structure in $A\beta_{42}$, leading to $A\beta_{42}$ aggregation in or on the membrane; 2) plasmalemmal phosphatidylinositol-4,5-phosphate ($PIP_2$) level inversely correlates $A\beta_{42}$ secretion from cultured cells; 3) $A\beta_{42}$-expression induces neuronal dysfunction and learning and memory dysfunction in flies, which can be rescued by the inhibition of phosphatidylinositol 3-kinase (PI3K); 4) recent discovery that the product of phosphatidylinositol 4-kinase (PI4KIIIα), Phosphatidylinositol-4-phosphate ($PI_4P$) increases significantly in cerebral cortex in AD patients, and the increased level is closely related to the degree of cognitive disorder in AD patients (Zhu, L., et al., Proc Natl Acad Sci USA, 2015).

In *Drosophila*, rolling blackout (rbo) gene encodes a plasma membrane protein RBO, which has a certain homology with diacylglycerol lyase. RBO protein functions in phospholipids metabolism, phototransduction, synaptic transmission and bulk endocytosis in *Drosophila*. RBO protein is conservative from yeast to human. The homologs of RBO in yeast (EFR3) and mouse (EFR3A and EFR3B) form a complex with phosphatidylinositol 4-kinase IIIα (PI4KIIIα) and a scaffold protein (referred to as Tetratricopeptide repeat domain 7, TTC7, see Baird D, Stefan C, et al., 2008, J Cell Biol; Nakatsu F, Baskin J F, et al., 2012, J Cell Biol) on cell membrane so as to anchor PI4KIIIα on the cell membrane, and further regulate plasmalemmal levels of phosphatidylinositol 4-phosphate (PI4P) and $PIP_2$.

In *Drosophila*, pan-neuronal expressed $A\beta_{42}$ fused to a secretory signal peptide induces intraneuronal Aβ accumulation and neural deficits. The inventors have shown previously that expression of $A\beta_{42}$ containing a secretory signal peptide in a simple neural pathway, the *Drosophila* giant fiber (GF) pathway, causes intraneuronal Aβ accumulation and age dependent synaptic failure and motor ability deficit. Such *Drosophila* expressing $A\beta_{42}$ provides a convenient platform to test the role of candidate genes in intraneuronal $A\beta_{42}$ accumulation and associated synaptic deficits. With this in mind, the inventors tested the effect of mutation or over-expression of genes rbo, PI4KIIIα, and ttc7, as well as common PI4KIIIα protein inhibitors on neurodegenerative disease in this model. The inventors further examined in APP/PS1 transgenic mice the effect of Efr3a (a mouse homolog of rbo gene) knockdown on the atrophy of hippocampal neurons, and the effect of small molecule inhibitor phenylarsine oxide (PAO), a frequently used inhibitor of PI4KIIIα on learning and memory, the level of A$\beta_{42}$ in CSF and brain parenchyma membrane, as well as the effect of PI4KA gene (which encodes PI4KIIIα protein) down-regulation on learning and memory, and the effect of PI4KIIIα product PI$_4$P on oligomeric formation of A$\beta_{42}$ in liposomes.

SUMMARY OF INVENTION

The present invention discloses that down-regulation of PI4KIIIα protein, RBO/EFR3/EFR3A/EFR3B protein, TTC7 protein, and amount of membrane protein complexes thereof or activities of related enzymes using genetic means or related inhibitors can facilitate Aβ (particularly A$\beta_{42}$) secretion of neuron cells and correspondingly reduce intraneuronal Aβ accumulation, so as to ameliorate neural deficits in *Drosophila* and mouse AD models. Therefore, the invention reveals the essential role of neuronal A$\beta_{42}$ secretion in AD treatment, and provides a novel strategy for treating AD; meanwhile, the invention provides novel medicines for treating AD, and further points out a new direction for screening medicine and therapeutic target for the treating AD.

In one aspect, the invention relates to a novel method of treating AD. According to a specific embodiment of the present invention, the present invention discloses a method for treating AD by using a PI4KIIIα inhibitor, which may be an anti-PI4KIIIα antibody, an inhibitory nucleotide specific for PI4KIIIα or Small molecule compound inhibitors specific for PI4KIIIα. Preferably, the specific inhibitory nucleotide to PI4KIIIα may be the nucleotide sequence as shown in SEQ ID NO: 6; the PI4KIIIα inhibitor is selected from one or more of the following small molecule compound inhibitors: PAO, derivatives of PAO, analogs of G1, A1, G1 or A1.

According to another embodiment of the present invention, the present invention also discloses a method for treating AD by using RBO/EFR3/EFR3A/EFR3B inhibitor. The RBO/EFR3/EFR3A/EFR3B inhibitor may be an anti-RBO/EFR3/EFR3A/EFR3B antibody.

Meanwhile, according to another embodiment of the present invention, the present invention also discloses a method for treating AD by using a PI$_4$P inhibitor. The PI$_4$P inhibitor may be an anti-PI$_4$P antibody, an OSH2-PH2X fusion protein, or an OSH2-2x-PH fusion protein.

In another aspect, the present invention also relates to a pharmaceutical composition that can be used to treat AD comprising one or more of PI4KIIIα inhibitors, RBO/EFR3/EFR3A/EFR3B inhibitors, and PI4P Inhibitor, and optionally a pharmaceutical carrier. Preferably, the pharmaceutical composition may further comprise one or more anti-Aβ antibodies and/or compounds capable of scavenging or clearing extracellular Aβ plaques or deposits selected from the group consisting of marine oligosaccharides Carbohydrates HSH971 and its analogs, acamprosate and its analogs, and edaravone and its analogs.

In addition, the present invention also relates to a method of how to screen for a drug for treating AD. According to a specific embodiment of the present invention, the present invention discloses a method for screening AD drugs which target the kinase activity of PI4KIIIα protein, and the method comprises the following steps: observing the effect of the drug candidate on the phosphokinase activity of PI4KIIIα, if the candidate drugs can inhibit the phosphokinase activity of PI4KIIIα, indicating that the candidate drug is a potential drug for the treatment of AD.

According to another embodiment of the present invention, the present invention also discloses a method for screening AD-targeted drug by targeting the interaction between RBO/EFR3/EFR3A/EFR3B protein, TTC7 protein and PI4KIIIα protein, comprising the following steps: observing the effect of candidate drugs on the interaction of RBO/EFR3/EFR3A/EFR3B protein, TTC7 protein and PI4KIIIα protein if the candidate drug can inhibit the interaction of RBO/EFR3/EFR3A/EFR3B protein, TTC7 protein and PI4KIIIα protein, thereby reducing the formation of the RBO/EFR3/EFR3A/EFR3B-TTC7-PI4KIIIα protein complex, indicating that the candidate drug is a potential drug for the treatment of AD.

According to another specific embodiment of the present invention, the present invention also discloses a method for screening AD drugs which targets the level of PI4P on the cell membrane, and the method comprises the following steps: observing drug candidates whether it has an effect on the level of PI4P on the cell membrane or not, and if the candidate drug can reduce the PI4P level on the cell membrane, it indicates that the candidate drug is a potential drug for treating AD.

DETAILED DESCRIPTION

Figure 1:
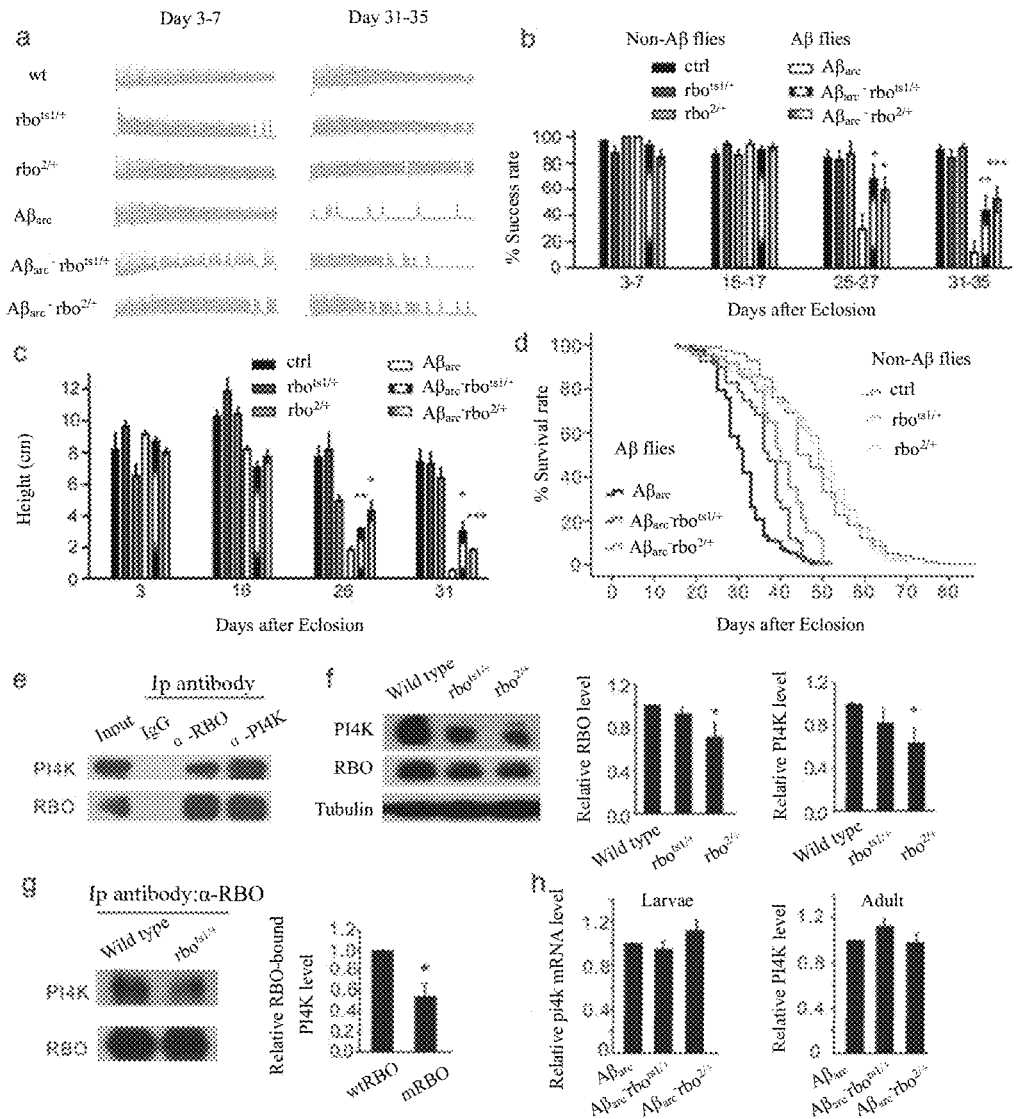
FIG. 1. rbo gene mutation ameliorates neural deficits in A$\beta_{arc}$-expressing flies, and reduce PI4KIIIα protein expression level or weaken interaction of PI4KIIIα protein with RBO protein.

In the present invention including the description and claims unless otherwise specified the following terms are used with the following meanings:

The term "rbo/Efr3/Efr3a/Efr3b gene" used herein refers to rbo gene originated from *Drosophila*, Efr3 gene originated from yeast, or Efr3a gene and Efr3b gene originated from mammals; term "RBO/EFR3/EFR3A/EFR3B protein" used herein refers to proteins encoded by rbo gene originated from *Drosophila*, Efr3 gene originated from yeast, or Efr3a/Efr3b gene originated from mammals.

The term "PI4KIIIα/PI4KA gene" used herein refers to PI4KIIIα gene or PI4KA gene originated from *Drosophila* or mammals; term "PI4KIIIα protein" used herein refers to proteins encoded by PI4KIIIα/PI4KA gene in *Drosophila* or mammals.

The term "ttc7 gene" used herein refers to ttc7 gene originated from *Drosophila* and mammals; term "TTC7 protein" used herein refers to proteins encoded by ttc7 in afore-mentioned *Drosophila* and mammals.

The term "inhibitor" used herein refers to materials capable of lowering, reducing or eliminating the amount, particular function, and particular property of a target object. Said target object can be a protein, polypeptide, nucleic acid and the like, while said inhibitor affects the amount, particular function, and particular property of the target object either directly or indirectly so as to result in the corresponding lowering, reducing or eliminating of the amount, particular function, and particular property of the target object. Said inhibitor can be a protein, polypeptide, nucleic acid, small molecule compound and the like.

For example, the term "PI4KIIIα inhibitor" used herein refers to materials capable of lowering, reducing or eliminating the expression, transcription, translation of PI4KIIIα/PI4KA gene, and/or stability of PI4KIIIα protein produced therefrom, binding ability to RBO/EFR3/EFR3A/EFR3B protein and TTC7 protein, and phosphokinase activity thereof, etc., which includes but is not limited to inhibitory nucleotides specific to PI4KIIIα/PI4KA, antibodies against PI4KIIIα protein, small molecule compound inhibitors capable of inhibiting PI4KIIIα kinase activity, and/or materials capable of inhibiting the interaction between PI4KIIIα protein and other membrane proteins, and the like.

Similarly, the term "RBO/EFR3/EFR3A/EFR3B inhibitor" used herein refers to materials capable of inhibiting, lowering, or eliminating the expression, transcription, translation of rbo/Efr3/Efr3a/Efr3b gene, and/or stability of RBO/EFR3/EFR3A/EFR3B protein produced therefrom, and binding ability to PI4KIIIα protein, etc., which includes but is not limited to inhibitory nucleotides specific to rbo/Efr3/Efr3a/Efr3b, antibodies against RBO/EFR3/EFR3A/EFR3B protein, and materials capable of inhibiting formation of complexes of RBO/EFR3/EFR3A/EFR3B protein and PI4KIIIα protein, and the like.

The term "TTC7 inhibitor" used herein refers to materials capable of lowering, reducing or eliminating the expression, transcription, translation of ttc7 gene, and/or stability of TTC7 protein produced therefrom, and binding ability to RBO/EFR3/EFR3A/EFR3B protein, etc., which includes but is not limited to inhibitory nucleotides specific to ttc7, antibodies against TTC7 protein, and/or materials capable of inhibiting interaction between TTC7 protein and membrane protein RBO/EFR3/EFR3A/EFR3B, and the like.

Same as above, the term "PI4P inhibitor" used herein refers to materials capable of inhibiting, lowering, or eliminating the quantity level of PI4P on cell membrane, which includes but is not limited to antibodies against PI4P, and OSH2-PH2X fusion protein or OSH2-2x-PH fusion protein which is capable of specific binding to PI4P.

The term "antibody" used herein refers to any immunoglobulin or complete molecule and fragments thereof which binds to a specific epitope. Said antibody includes but not limited to polyclonal antibodies, monoclonal antibodies, chimeric antibodies, humanized antibodies, single chain antibodies, and fragments and/or parts of intact antibodies, as long as such fragments or parts retain the antigen binding capacity of the parent antibody. In the invention, for example, "antibody against PI4KIIIα" refers to monoclonal antibodies, polyclonal antibodies, single chain antibodies and immunological active fragments or parts thereof capable of specific binding to PI4KIIIα protein, or functional variants or functional fragments thereof. In the invention, terms such as "PI4KIIIα antibody", "antibody against PI4KIIIα", and "anti-PI4KIIIα antibody" are used interchangeably.

In the invention, "functional variant" refers to the protein or polypeptide of the invention with one or more amino acid modification in its amino acid sequence. The modification can be a "conservative" modification (wherein the substituted amino acid has similar structure or chemical property) or a "non-conservative" modification; similar modification also include addition or deletion of amino acid or both. However, neither the modification of amino acid residue nor the addition or deletion of amino acid would substaintially change or damage the biological or immunological activity and function of the original amino acid sequence. In the invention, similarly, "functional fragment" refers to any part of the protein or polypeptide of the invention, which retains the substantially similar or identical biological or immunological activity and function of the protein or polypeptide of which it is a part (the parent protein or polypeptide).

The term "inhibitory nucleotide" used herein refers to nucleotide compound capable of binding to and inhibiting expression of a specific gene. Typical inhibitory nucleotide includes but not limited to antisense oligonucleotides, triple helix DNAs, RNA aptamers, ribozymes, small interfering RNA (siRNA), short hairpin RNA (shRNA) and microRNA. These nucleotide compounds bind to said specific genes with higher affinity than other nucleotide sequences, so as to inhibit expression of the specific genes.

The term "small molecule compound" used herein refers to organic compounds with molecular weight less than 3 k dalton which can be either natural or chemically synthesized. Term "derivative" used herein refers to compounds generated by modifying the parent organic compound through one or more chemical reactions, which have similar structures as the parent organic compound and similar effects in their functions. Term "analogue" used herein refers to compounds which were not generated by chemically modifying the parent organic compound but are similar to the parent organic compound in structure and have similar effects in their functions.

The term "Alzheimer's disease" (AD) used herein refers to an age-related neurodegenerative disease characterized in a progressive learning and memory dysfunction. Most AD patients in middle and advanced stages have neural extracellular beta amyloid plaques, initracellular neurofibrillary tangles formed of Tau protein, or loss of synapse and nerve cells. The disease may exist in human or in animals, such as dogs.

The term "Aβ" used herein refers to a series of polypeptides with a length of 38-48 amino acids generated by secretase cleavage of amyloid precursor protein (APP), which include polypeptides $A\beta_{38}$, $A\beta_{40}$, $A\beta_{42}$, $A\beta_{44}$, $A\beta_{45}$ and the like having same amino acid sequences. In the invention, Aβ can also be generated by cleavage of other protein cleavage enzyme of Aβ fusion protein expressed by transgenic method or infecting cells with viral vectors through particular expression system, for example, Aβ through its N-terminus may form fusion proteins with the secretory signal peptide originated from proteins encoded by *Drosophila* necrotic gene (amino acid sequence: MASKVSILLLLTVHLLAAQTFAQDAE-FRHDSGYEVHHQKLVFFAEDVGSNKGAIIGL MVGGVVIA) (SEQ ID NO: 1) or secretory signal peptide originated from rat pre-proenkephalin (amino acid sequence: MAQFLRLCIWLLALGSCLLATVQA) (SEQ ID NO: 2) or the like.

The term "Aβ secretion" used herein refers to a process of discharge of Aβ generated intracellularly or on cell membranes via cell membrane, which may decrease intracellular Aβ accumulation. Wherein, "$A\beta_{42}$ secretion" specifically refers to a process of the discharge of $A\beta_{42}$ generated intracellularly or on cell membranes via cell membrane, which may decrease intracellular $A\beta_{42}$ accumulation.

The term "therapeutic target" used herein refers to various materials that can be used to treat a certain disease and the target of the material in animal or human bodies. Treatment effects on said disease are obtainable when said materials act on said target. Said materials can be a variety of materials such as protein, polypeptide, nucleic acid, small molecule compound, said target can be material substances such as a certain gene (including a specific sequence of a gene), a ceratin protein (including a specific site of a protein), a certain protein complex (including specific binding site thereof), or certain charactistics, certain functions, certain interaction relationships with peripheral substances and environment of aforementioned genes and/or proteins, etc., as long as said materials can affect the gene, protein, protein complex, or charactistic, function, interaction relationship thereof so as to treat the disease.

The terms "treat", "treating", or "treatment" used herein refer to reversing, ameliorating or inhibiting the progression of the disease to which the term is applied, or one or more symptoms of the disease. As used herein, depending on the condition of the patient, the term also include prevention of disease, which includes the prevention of disease or the onset of any symptoms associated therewith, and ameliorating symptoms or reducing the severity of any condition before its onset.

The terms "inhibit", "weaken", "down-regulate", "remove" and the like all refer to reduction or decreasing in quantity or degree. Such reduction or decreasing is not limited to any extent as long as it exhibits such a trend. For example, the reduction or decreasing can be 100% relative to the original quantity or degree, or can be 50% or even 1% or less.

The present invention reveals a variety of actions such as down-regulating the expressions of RBO/EFR3/EFR3A/EFR3B protein, TTC7 protein, or PI4KIIIα protein, weakening the interactions between RBO/EFR3/EFR3A/EFR3B protein, TTC7 protein, and PI4KIIIα protein, and inhibiting enzyme activity of PI4KIIIα can improve the age-related dysfunctions such as synaptic deficit and loss of nerve cells expressing $A\beta_{42}$, and discloses that these effects are achieved by facilitating Aβ (particularly $A\beta_{42}$) secretion of neuron cells and reducing Aβ (particularly $A\beta_{42}$) accumulation on neuron cell membranes or in cells.

In the invention, for example, the inventor discovered that Efr3a gene knockdown can reduce the atrophy of dendrites and spines of hippocampal neurons in APP/PS1 transgenic mice, while gavage with phenylarsine oxide (PAO), a common inhibitor of PI4KIIIα protein, can significantly ameliorate the learning and memory of APP/PS1 mice, and can reduce the content of plasmalemma coupled $A\beta_{42}$ (particularly the $A\beta_{42}$ in $A\beta_{42}$ aggregates/oligomers) in brain tissue, although the process may accompanied with increasing of $A\beta_{42}$ content in cerebrospinal fluid. These results demonstrated that dementia symptoms of APP/PS1 mice can be ameliorated by facilitating neuronal secretion of $A\beta_{42}$ and reducing accumulation of $A\beta_{42}$ (particularly aggregated $A\beta_{42}$) in neurons or on neuron membranes.

The inventors discovered that down-regulating the expressions of RBO/EFR3/EFR3A/EFR3B protein, TTC7 protein, or PI4KIIIα protein in cells or neurons, or preventing their formation of protein complexes to decrease the localization of PI4KIIIα protein on membranes, or inhibiting phosphokinase activity of PI4KIIIα protein, can facilitate $A\beta_{42}$ secretion of cells and neurons, reducing $A\beta_{42}$ accumulation in neurons, and ameliorating AD-related neorodegeneration and dysfunctions thereof; meanwhile, neither expression levels of $A\beta_{42}$ or APP, nor activities of α, β, and γ secretase which cleave APP were significantly affected. In addition, the inventors also discovered that PI4P, a product of PI4KIIIα protein, facilitate aggregation of $A\beta_{42}$ monomers in liposomes, while such facilitation is much stronger than that of the precursor of PI4P (PI) and its derivative PI4,5P.

The inventors believe that Aβ (including $A\beta_{42}$) are generated from plasmalemmal or intracellular organs; thus generated Aβ may be secreted from cells through passive release, exocytosis, lysosomal-mediated release, or other undiscovered pathways. Despite of the origin of Aβ or how it is secreted, plasmalemma is the last pathwaythrough which Aβ leaves the cell. Due to the hydrophobicity of Aβ, on plasmalemma, Aβ is inserted into hydrophobic fatty acid chain region on one hand, and interacts with phosphatidylinositol (particularly phosphorylated phosphatidylinositol PI4P) and other acidic phospholipid on the other hand, such interaction facilitates the conformation changes of Aβ from random coil into β-structure, and further aggregates as Aβ aggregate to be deposited on membranes or be accumulated in cells by endocytosis. Furthermore, studies have demonstrated that the affinity of soluble Aβ (including $A\beta_{42}$) aggregates/oligomers to cell or liposome membrane is much higher than that of Aβ monomer. Therefore, aggregated Aβ is much easier to accumulate on cell membranes.

PI4P is a major component of plasmalemmal phosphorylated phosphatidylinositol, which exhibits a stronger facilitation on the formation of Aβ aggregates/oligomers than PI and $PIP_2$. In the invention, the inventors discovered that the facilitation effect of PI4P on the formation Aβ$_{42}$ aggregates/oligomers in liposomes is clearly dose dependent. Down-regulating the expression of RBO/EFR3/EFR3A/EFR3B protein, TTC7 protein, or PI4KIIIα protein, preventing their formation of protein complexes, or inhibiting the kinase activity of PI4KIIIα protein, can reduce PI4P production on cell membranes. Therefore, down-regulating expression of RBO/EFR3/EFR3A/EFR3B protein, TTC7 protein, or PI4KIIIα protein, or preventing the formation of membrane attached protein complexes of RBO/EFR3/EFR3A/EFR3B protein, TTC7 protein, and PI4KIIIα protein, or inhibiting the corresponding phosphokinase activity of PI4KIIIα protein, can substantially decrease the amount of plasmalemma phosphorylated phosphatidylinositol (particularly PI4P) so as to weaken the interaction between plasmalemmal Aβ (including Aβ$_{42}$) and phosphorylated phosphatidylinositol, and result in more plasmalemmal Aβ existing in the random form of Aβ monomer. As described above, such random form of Aβ monomer has low affinity to membrane, thus is relatively easily released from membrane and secreted extracellularly. Therefore, above regulation behaviors can effectively reduce intracellular accumulation of Aβ without affecting the expression level of APP or the activities of α, β, and γ secretase, so as to result in an obvious increase of extracellular Aβ level.

Previous studies have reported that Aβ$_{42}$ accumulation in *Drosophila* can activate PI3K and related PI3K/Akt signaling pathway, thus inducing the AD-related synaptic deficits and loss of long-term memory; correspondingly, related research believed that inhibiting PI3K activity can be a method of treating AD. However, in the present invention, the inventors discovered that intracellular Aβ$_{42}$ accumulation is not caused by PI3K/Akt signaling pathway activation of phosphatidylinositol kinases (including PI3K), but is more directly caused by phosphatidylinositol on phosphorylated membranes after plasmalemmal phosphatidylinositol kinase is activated; moreover, the phosphatidylinositol kinase involved in the present invention is mainly PI4KIIIα rather than the PI3K in the PI3K/Akt signaling pathway. For example, the inventors discovered that by using phosphatidylinositol kinase inhibitor highly specific to PI4KIIIα but not sensitive to PI3K, such as PAO, Aβ$_{42}$ secretion from cells can be effectively facilitated with low concentration.

It is thus revealed by the inventors that in order to achieve AD treatment, it is possible to adopt a method of facilitating Aβ secretion, particularly Aβ$_{42}$ secretion, so as to decrease Aβ (including Aβ$_{42}$) accumulation in neural cells or on cell membranes. But the increased secretion of Aβ cannot be attributed to the up-regulation of APP or the increased production of Aβ caused by a change in the activities of α, β, and γ secretases.

It is understandable by one of ordinary skill in the art that there are a variety of routes to facilitate Aβ secretion of neural cells, including weakening the binding or interaction between Aβ and plasmalemma saccharides, lipids, and proteins. In the invention, it is preferred to facilitate Aβ secretion of cells by reducing Aβ (particularly Aβ$_{42}$) aggregation on cell membranes, as described above.

Furthermore, the present invention reveals that by regulating the quantities of RBO/EFR3/EFR3A/EFR3B protein, TTC7 protein, and PI4KIIIα protein and their capacity of forming complexes, as well as by regulating phosphokinase activity of PI4KIIIα protein, Aβ aggregates/oligomers formed on cell membranes can be reduced so as to facilitate Aβ (particularly Aβ$_{42}$) secretion of cells, therefore, these proteins and the relationships thereof can constitute potential therapeutic targets for treating AD.

Accordingly, it is understandable by one of ordinary skill in the art that inhibitors or methods capable of inhibiting, lowering, reducing, or eliminating the expression, transcription, or translation of rbo/Efr3/Efr3a/Efr3b gene, and capable of decreasing the stability of RBO/EFR3/EFR3A/EFR3B protein encoded therefrom, as well as inhibitors or methods capable of inhibiting its formation of protein complexes with phosphatidylinositol kinase PI4KIIIα protein and TTC7 protein, can be used to treat AD. Said RBO/EFR3/EFR3A/EFR3B inhibitors include but not limited to inhibitory nucleotides of rbo/Efr3/Efr3a/Efr3b gene (including antisense RNA, siRNA, miRNA or the like), antibodies against RBO/EFR3/EFR3A/EFR3B protein, and the like.

It is understood by the skilled in the art that inhibitory nucleotides of rbo/Efr3/Efr3a/Efr3b gene are well-known in the art (e.g., see, www.genecards.org, and available products: ORIGENE, Cat. #SR308056 and Cat. #TR303768). Similarly, antibodies against RBO/EFR3/EFR3A/EFR3B protein are well-known in the art (e.g., see, www.genecards.org, and available products: Novus, Cat. #NBP1-81539; Thermo Fisher Scientific, Cat. #PA5-24904).

Moreover, as described above, regulating the cellular expression, transcription, or translation of PI4KIIIα/PI4KA gene, regulating the stability of PI4KIIIα protein encoded from PI4KIIIα/PI4KA gene, regulating the capacity of PI4KIIIα protein forming complexes with membrane protein RBO/EFR3/EFR3A/EFR3B and TTC7 protein, and regulating phosphokinase activity of PI4KIIIα protein, can be regarded as methods of treating AD. Therefore, it is understandable by one of ordinary skill in the art that inhibitors or methods capable of inhibiting, lowering, reducing, or eliminating the expression, transcription, or translation of PI4KIIIα/PI4KA gene, or capable of decreasing the stability of PI4KIIIα protein encoded therefrom, inhibitory nucleotides includes but not limited to that specific to PI4KIIIα/PI4KA gene, antibodies against PI4KIIIα protein, and small molecule compound inhibitors capable of inhibiting protein complex formation of PI4KIIIα protein with membrane proteins and capable of inhibiting kinase activities, can be used to treat AD. Preferably, the inhibitor is a small molecule compound, for example, PAO (Phenylarsine Oxide), PAO derivatives, A1, G1, or analogues of A1 and G1. More preferably, the inhibitor is PAO or PAO derivatives.

It is understood by the skilled in the art that PAO is a small molecule compound having a basic structure comprising oxoarsine group and phenyl group, which exhibits a strong inhibitory effect on the phosphokinase activity of PI4KIIIα protein. Chemical structure of PAO is:

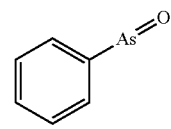

Phenylarsine oxide
(oxo(phenyl)arsane)

Synthesis method of PAO is well-known to the skilled in the art. According to the present invention, compounds that can be used in the treatment of AD further include derivatives of PAO, as long as the compound exhibit inhibitory effect on the phosphokinase activity of PI4KIIIα protein. It is understood by the skilled in the art that synthesis methods of such derivatives are well-known in the art.

Similarly, it is understood by the skilled in the art that A1 and G1 both are small molecule compound inhibitors of PI4KIIIα protein and having similar structures. The chemical structure of A1 is:

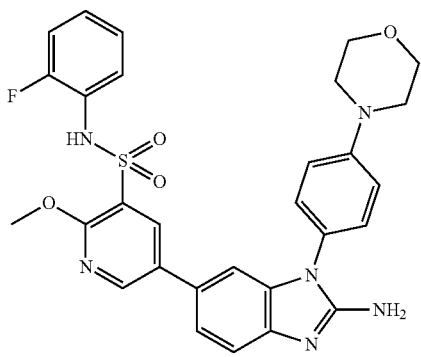

A1

5-(2-amino-1-(4-(4-morpholinyl)phenyl)-1H-benz-imidazol-6-yl)-N-(2-fluorophenyl)-2-methoxy-3-pyridinesulfonamide Chemical structure of G1 is:

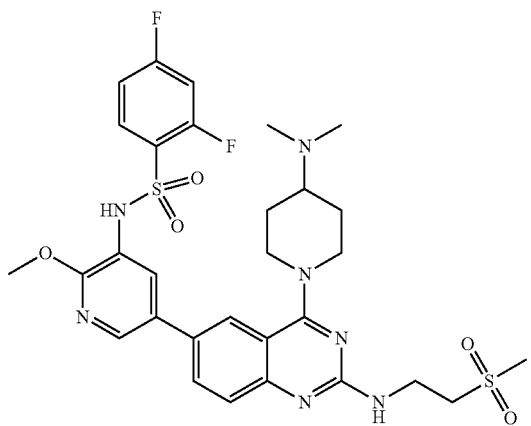

G1

(aS)-5-(2-amino-4-oxo-3-(2-(trifluoromethyl)phenyl)-3,4-dihydroquinazolin-6-yl)-N-(2,4-difluorophenyl)-2-methoxypyridine-3-sulfonamide Synthesis methods of A1 and G1 are well-known in the art (e.g., see, Bojjireddy, N., et al. (2014), JBC 289:6120-6132; Leivers, A. L., et al. (2014), JMC 57:2091-2106). According to the present invention, structural analogues of A1 and G1 can be used to treat AD as long as they exhibit inhibitory effect on the phosphokinase activity of PI4KIIIα protein. It is understood by the skilled in the art that synthesis methods of such structural analogues are well-known in the art.

In addition, the formation of membrane complexes of PI4KIIIα protein and RBO/EFR3/EFR3A/EFR3B protein requires the assistance of scaffold protein TTC7. Therefore, according to the invention, it is understandable by one of ordinary skill in the art that inhibitors or methods capable of inhibiting, lowering, reducing, or eliminating the expression, transcription, or translation of ttc7 gene, and capable of decreasing the stability of TTC7 protein encoded therefrom, as well as inhibitors or methods capable of inhibiting its formation of protein complexes with RBO/EFR3/EFR3A/EFR3B protein and PI4KIIIα protein, can be used to treat AD. Said TTC7 inhibitors include but not limited to inhibitory nucleotides of ttc7 gene (including antisense RNA, siRNA, miRNA or the like), antibodies against TTC7 protein, and the like.

Moreover, according to the invention, down-regulating the expression of RBO/EFR3/EFR3A/EFR3B protein and PI4KIIIα protein, or preventing their formation of protein complexes to decrease the distribution of PI4KIIIα protein on membranes, or inhibiting the phosphokinase activity of PI4KIIIα protein, essentially leads to reduction of plasmalemmal PI$_4$P and further facilitates Aβ secretion of cells. Therefore, it is understandable by one of ordinary skill in the art that any inhibitor or method capable of decreasing the quantity or level of plasmalemmal PI$_4$P, and further decreasing the formation of Aβ aggregates/oligomers on cell membranes, can achieve the effect of treating AD as described above.

It is understandable by the skilled in the art that aforementioned PI$_4$P inhibitors can be antibodies or other molecules that specifically binds to PI$_4$P. Currently, synthesis methods of antibodies against PI$_4$P are well-known in the art (see, Brown B K and Karasavass N, et al., 2007, J virol; Wassef N M and Roerdink F, et al. 1984, Mol Immuol). For example, it can be human-derived broad-neutralizing antibody 4E10, and other antibodies against PI$_4$P. Currently, synthesis methods of molecules specifically bind to PI$_4$P are well-known in the art (see, Balla A and Kim Y J, et al., 2008, Mol Biol Cell; Zubenko G S and Stiffler et al., 1999, Biol Psychiary). For example, it can be an OSH2-PH2X fusion protein, or an OSH2-2x-PH fusion protein.

Aforementioned materials provided by the present invention that can be used to treat AD or having treatment potential to AD (hereinafter collectively referred to as "the materials of invention"), including but not limited to antibodies against RBO/EFR3/EFR3A/EFR3B, antibodies against PI4KIIIα, antibodies against TTC7, antibodies against PI$_4$P, inhibitory polypeptides specific to rbo/Efr3/Efr3a Efr3b gene, inhibitory polypeptides specific to PI4KIIIα/PI4KA gene, and small molecule compounds inhibiting phosphokinase activity of PI4KIIIα protein, etc., can be isolated, purified, synthesized and/or recombined.

Moreover, the materials of invention can also be formulated into a composition, such as a pharmaceutical composition. In this regard, the invention provides a pharmaceutical composition comprising any of aforementioned antibodies, inhibitory polypeptides, and/or small molecule compounds, and a pharmaceutically acceptable carrier.

The pharmaceutical composition of the invention containing any of the materials of invention can comprise more than one material of invention, e.g., antibody and small molecule compound, inhibitory polypeptide and antibody, or two or more antibodies or small molecule compounds. Alternatively, the pharmaceutical composition can also comprise a material of invention in combination with another pharmaceutically active agent or drug. For example, it can comprise antibody drug against Aβ, such as Bapineuzumab, or compound which binds to neural extracellular Aβ or 3 amyloid plaque in brain to block Aβ aggregation or to facilitate disaggregation of Aβ aggregates, such as marine-derived sulfated oligosaccharide HSH971 and analogues thereof, acamprosate (tramiprosate) and analogues thereof, and Edaravone and analogues thereof. In this way, the pharmaceutical composition facilitates Aβ secretion from neurons on the one hand, and facilitates the removal of Aβ outside neurons on the other hand, thereby achieving a better therapeutic effect on the treatment of AD.

In another aspect, the present invention provides a method for screening new medicines or therapeutic targets for the treatment of AD. The method is designed based on aforementioned discoveries of the invention, i.e., intracellular $Aβ_{42}$ accumulation can be reduced by facilitating $Aβ_{42}$ secretion so as to ameliorate and prevent AD-associated neurodegeneration and dysfunction. Therefore, the criteria for screening medicines or therapeutic targets is the facilitation effect on Aβ secretion (particularly $Aβ_{42}$ secretion) after administration of the medicine or regulation of the therapeutic target, while increased Aβ secretion cannot be attributed to the up-regulation of APP or the increased production of Aβ caused by change in activities of α, β, and γ secretase.

According to the present invention, regulation of the therapeutic target refers to using relevant materials to act on the therapeutic target either directly or indirectly so as to change the function, property, or relationship with peripheral environment of the therapeutic target, thus causing or inducing the facilitation of Aβ secretion (particularly $Aβ_{42}$ secretion) of cells.

It is understood by one of ordinary skill in the art that in order to select effective drug for treating Alzheimer's disease, cell lines for screening test can be eukaryotic cell lines from mammals, insects or the like, e.g., HEK293, COS7, N2a, SH-SY5Y, S2, sf9 and the like. The method includes testing whether a candidate drug may reduce Aβ accumulation, particularly $Aβ_{42}$ accumulation, on cell membrane or in cells, so as to select effective drugs for treating Alzheimer's disease. Preferably, the test of whether Aβ secretion is increased can be performed in cell lines over-expressing APP (e.g., HEK293, COS7, N2a, SH-SY5Y cell lines stably transfected with human-derived APP) or with *Drosophila* model, preferably tissues of third instar larva of *Drosophila*. Whether Aβ secretion is increased can be detected with methods of immunoassay, including enzyme-linked immunosorbent assay (ELISA) or electro-chemiluminescence assay (ECLIA).

Preferably, the method for screening medicines or therapeutic targets for the treatment of AD can include: observing the effect of invention of candidate medicine or target regulation on enzyme activity of PI4KIIIα, if the invention of candidate medicine or target regulation negatively affects the function of PI4KIIIα kinase in the detection system, i.e., characterized in reduction of PI4KIIIα kinase activity or plasmalemmal $PI_4P$ level, then it indicates that the candidate medicine, agent or target is a potential medicine or therapeutic target for treating AD. After such screening, it is further detected that whether intracellular Aβ (particularly $Aβ_{42}$) accumulation is reduced and whether extracellular Aβ secretion is facilitated. With these methods, screening efficiency of candidates can be greatly improved.

According to one specific embodiment of the present invention, the method for screening medicines or therapeutic targets for the treatment of AD can include: determining based on directly analyzing whether invention of candidate medicine or regulation of therapeutic target re-distributes plasmalemmal PI4KIIIα protein to endochylema so as to reduce the quantity of PI4KIIIα protein on membrane and induces a reduction of the aggregation/oligomerization of plasmalemma Aβ monomer as well as increasing extracellular secretion. Preferably, fluorescently labeled PI4KIIIα can be selected for observation, such as PI4KIIIα labeled with fluorescent protein (GFP-PI4KIIIα), and observing whether the fluorescently labeled PI4KIIIα transfers from plasmalemma to endochylema.

According to one specific embodiment of the present invention, the method for screening medicines or therapeutic targets for the treatment of AD can also be conducted with methods such as co-immunoprecipitation assay in which interactions between proteins are analyzed. If invention of candidate medicine or regulation of therapeutic target reduces interactions between RBO/EFR3/EFR3A/EFR3B protein, TTC7 protein, and PI4KIIIα protein, it indicates that the medicine or therapeutic target is capable of weakening the capacity of PI4KIIIα protein in forming membrane protein complexes so as to reduce aggregation of plasmalemma Aβ monomer as well as increasing extracellular secretion.

According to one specific embodiment of the present invention, the method for screening medicines or therapeutic targets for the treatment of AD can also be performed by directly analyzing whether invention of candidate medicine or regulation of therapeutic target reduces plasmalemmal $PI_4P$ level. Preferably, fluorescence microscope, confocal microscope, or two-photon microscope can be utilized to observe whether fluorescently labeled molecule that specifically binds to $PI_4P$, such as OSH2-PH2X or OSH2-2x-PH fusion protein labeled with fluorescent protein, is decreased in plasmalemma quantity or transferred from plasmalemma to endochylema.

The present invention will be further illustrated in detail below. However, ways to carry out the present invention are not limited to the following examples.

Hereinafter, data are obtained mainly through animal and cell culture experiments, and are analyzed with SPSS software. Unless otherwise specified, data are represented by mean±sem. $P<0.05$ indicates the difference is statistically significant. All data shown here and below are represented by mean±sem. "*", "", and "*" each represents that $p<0.05$, $0.01$, and $0.001$, respectively.

Example 1: *Drosophila* Strains and Genetics Methods

Standard culture medium, alternating cycle of 12-hour light and 12-hour dark, culturing under constant temperature of 25° C.

The following transgenic *Drosophila* strains were utilized in the invention: $rbo^{S3584}$, [UAS]$Aβ_{arc}$, [UAS]$Aβ_{42}$, [UAS]dtau, [UAS]mCD8-gfp (provided by Dr. Z. Wang), [UAS]shibire$^{ts1}$ (provided by Dr. A Guo), [Gal4]A307 (provided by Dr. O'Kane). Wherein, $rbo^{S3584}$ gene is a transgene constructed from wild type genome DNA comprising rbo gene via site-directed mutation, whose expression is driven by the pre-driver of the rbo gene itself. [Gal4]A307 expresses transcription factor Gal4, which drives [UAS]$Aβ_{arc}$, [UAS]$Aβ_{42}$, [UAS]dtau, [UAS]mCD8-gfp, [UAS]shibire$^{ts1}$ transgenes to express $Aβ_{arc}$, $Aβ_{42}$, dTau, mCD8-GFP, or temperature sensitive mutation Dynamin in neurons of Giant Fiber pathway and in a small amount of other neurons. *Drosophila* mutants utilized in the invention include: rbo$^{ts1}$ (temperature sensitive missense mutation), rbo$^2$ (knockdown mutation), itpr$^{sv35}$ (nonsense mutation, Bloomington Stock #30740), PI4KIIIα$^{def}$ (mutation with deletion of PI4KIIIα gene and peripheral DNA, Bloomington Stock #9518), PI4KIIIα$^{GS27}$, and PI4KIIIα$^{GJ86}$ (both are nonsense mutations). P{lacW}l(2)k14710k$^{15603}$ transposon is inserted into the first exon of l(2) k14710 gene in order to prevent transcription of l(2) k14710 (Bloomington Stock #11134);

P{EPgy2}bin3$^{EY9582}$ (Bloomington Stock #20043). In order to purify the genetic background, all transgenes and mutant flies were backcrossed with a wild isogenic strain (isogenic w$^{1118}$, Bloomington stock #5905) for more than 5 generations before use.

Prior research of the inventors discovered that flies (*Drosophila*) expressing wild type or the arctic mutant Aβ$_{42}$ (Aβ$_{42}$ or Aβ$_{arc}$ flies or *Drosophila*) in neurons of the GF pathway exhibit intraneuronal Aβ$_{42}$ accumulation, age dependent synaptic transmission failure, and premature death. Such flies also exhibit an age-dependent decline of climbing ability. In order to study the role of rbo gene in the neural deficits caused by intraneuronal Aβ$_{42}$ accumulation, two mutations of rbo gene, missense mutation (rbo$^{ts1}$) and knockdown mutation (rbo$^2$), were introduced into Aβ$_{arc}$ flies, and the effects on synaptic transmission, climbing ability, and age were respectively tested. Four groups of flies were constructed: control flies (control, ctrl), rbo$^{ts1/+}$ or rbo$^{2/+}$ heterozygotes (rbo), Aβ$_{arc}$ flies (Aβ$_{arc}$), and Aβ$_{arc}$ flies with rbo$^{ts1/+}$ or rbo$^{2/+}$ heterozygous mutation (Aβ$_{arc}$-rbo). Each group contains 1-2 strains, wherein, "ctrl" denotes wild type control flies having [Gal4]A307 transgene; "rbo$^{ts1/+}$" and "rbo$^{2/+}$" denotes rbo$^{ts1/+}$ and rbo$^{2/+}$ heterozygous flies having one copy of [Gal4]A307 transgene; "Aβ$_{arc}$" denotes [Gal4]A307 [UAS]Aβ$_{arc}$ double transgenic flies; "Aβ$_{arc}$-rbo$^{ts1/+}$" and "Aβ$_{arc}$-rbo$^{2/+}$" each denotes [Gal4]A307-rbo$^{ts1}$ [UAS]Aβ$_{arc}$ and [Gal4]A307-rbo$^2$ [UAS]Aβ$_{arc}$, respectively. The first two groups of flies did not express Aβ$_{arc}$ and were classified as "non-Aβ flies", whereas the latter two groups of flies express Aβ$_{arc}$ and were classified as "Aβ flies".

Example 2: Rbo Gene Mutation Specifically Suppresses Neural Deficits in Aβ$_{42}$-Expressing *Drosophila*, Tested by Synaptic Transmission Examination Examination method of synaptic transmission: Recording of excitatory junction potentials (EJPs) in Giant Fiber (GF) system intracellularly. Adult female fly of a certain day-age was mounted ventral side down on a glass slides with low-melting wax tackiwax (Boekel Scientific) under a dissection microscope. Recording system includes one reference electrode in abdomen, two stimulation electrodes inserted into two eyes, and one recording electrode inserted into dorsal longitudinal muscle cell. Both eyes were subjected to electric stimulation (100 Hz, 50 pulses). Stimulation intensity is 5-20 volts with a duration of 0.2 ms, approximately 150% of the threshold stimulation intensity. Electric signals were recorded and amplified by Axonal clamp 900A (Molecular Devices), and were digitized at a frequency of 10 kHz by Digidata 1440A (Molecular Devices). Data were recorded and analyzed by pClamp software (version 10.0; Molecular Devices). All electrodes are glass electrode filled with 3M KCl solution. Environment temperature was 25° C. during recording.

FIG. 1 shows representative records of brain stimulated EJP in different day-age in four groups of flies (FIG. 1 panel a) and quantitative analysis of success rates of elicited EJPs (FIG. 1 panel b). It is particularly noted that rbo mutation significantly inhibited the age dependent neuronal synaptic transmission failure caused by Aβ$_{arc}$. Statistical analysis was performed using one-way ANOVA on data of 3-7$^{th}$, 15-17$^{th}$, and 25-27$^{th}$ day (n=6~12), and 31-35th day (n=10~23).

According to the above examination method of synaptic transmission, intracellular recording of EJPs in the dorsal longitudinal muscle fibers under high-frequency electric stimulation (100 Hz, 50 pulses) was performed on the 3-7$^{th}$, 15-17$^{th}$, 25-27$^{th}$, and 31-35$^{th}$ days after eclosion. The success rate of EJPs elicited by high-frequency electric stimulation in the first group was not significantly differentiable from that in the other three groups on the 3-7$^{th}$ and 15-17$^{th}$ days (FIG. 1 panel a and b). On the 25-27$^{th}$ and 31-35$^{th}$ days, success rate of EJPs in Aβ$_{arc}$-rbo flies became lower than that in control flies and rbo flies, but was significantly higher than that in Aβ$_{arc}$ flies (FIG. 1 panel a and b).

These results illustrates that rbo gene mutation ameliorates the age-dependent synaptic transmission failure caused by intraneuronal Aβ$_{arc}$ accumulation. It is unlikely that the difference in genetic background has contributed to the amelioration, since the genetic background of the transgenic flies and rbo mutants used for creating the four groups of flies were backcrossed with a wild isogenic strain (isogenic w$^{1118}$) for more than 5 generations before use, thus the genetic background is essentially purified. Since total knockdown of rbo gene causes embryonic lethality, its effect on Aβ$_{arc}$ induced synaptic transmission failure could not be examined.

Example 3: Rbo Gene Mutation Specifically Suppresses Neural Deficits in Aβ$_{42}$-Expressing Flies, Tested by Tube-Climbing Ability Assay Tube climbing test: Climbing ability was examined by measuring the average climbing height of 10 flies at the seventh second from the bottom of vertically placed testing tubes. A fruit fly climbing ability testing apparatus with high reproducibility was developed. The apparatus includes: 1) a rectangular metal frame (32 cm width, 21 cm height) within which 10 transparent plastic tubes are mounted vertically; 2) an electric motor for driving the vertical movement of the metal frame; 3) a stepping actuator for controlling the electric motor at the working cycle of rapidly moving the metal frame up and down for four times for a predetermined height at a 1 minute interval; 4) a video camera for videotaping the climbing process; 5) an analyzing software for analyzing the climbing position of a fly at a certain time of the video. In experiments, 10 flies of a specific genotype were transferred into each transparent plastic tube. The tubes were evenly distributed and mounted in the metal box. The metal box can slide vertically along two metal rods which were mounted vertically on the base. In the climbing test, the stepping actuator controls the electric motor to lift up the metal box for 5.8 cm and then releases, such that the metal box drops to the original position by gravity. Upon the metal box stopped moving, files dropped down to the bottom of the tubes. After the metal box was moved up and down for 4 times in 3 seconds, all files were at the bottom of the tubes. Then the flies were allowed to climb up along the wall of the tubes. The whole processes were videotaped for subsequent analysis. The inventors developed a computer program for measuring the height of a fly at any given time after tube climbing was started.

In FIG. 1 panel c, rbo gene mutation ameliorated the age dependent climbing ability in Aβ$_{arc}$-expressing flies, one-way ANOVA analysis was performed, n=3 (3 groups of flies, 10 flies in each group).

Climbing ability was examined on the 3$^{rd}$, 16$^{th}$, 26$^{th}$, and 31$^{st}$ day after eclosion. On the 3$^{rd}$ and 16$^{th}$ day, the climbing abilities of flies in four groups were similar (FIG. 1 panel c). On the 26$^{th}$ and 31$^{st}$ day, Aβ$_{arc}$-rbo flies climbed significantly higher than Aβ$_{arc}$ flies, although not as high as control and rbo flies (FIG. 1 panel c).

Example 4: Rbo Gene Mutation Specifically Suppresses Neural Deficits in Aβ$_{42}$-Expressing Flies, Tested by Longevity Assay Longevity (lifespan) assay: 100 or 200 flies of each genotype were equally separated into 5 or 10 tubes containing standard fly food and dry yeast, and cultured at 25° C. Flies were transferred to tubes with fresh food and dry yeast every 3 days, and dead flies were counted at each transfer. Survival rates were analyzed with the SPSS 11 Kaplan-Meier software.

In FIG. 1 panel d, rbo gene mutation prolonged the lifespan of Aβ$_{arc}$-expressing flies. n=200 flies for each group, p<0.001, Log Rank test.

Figure 7:
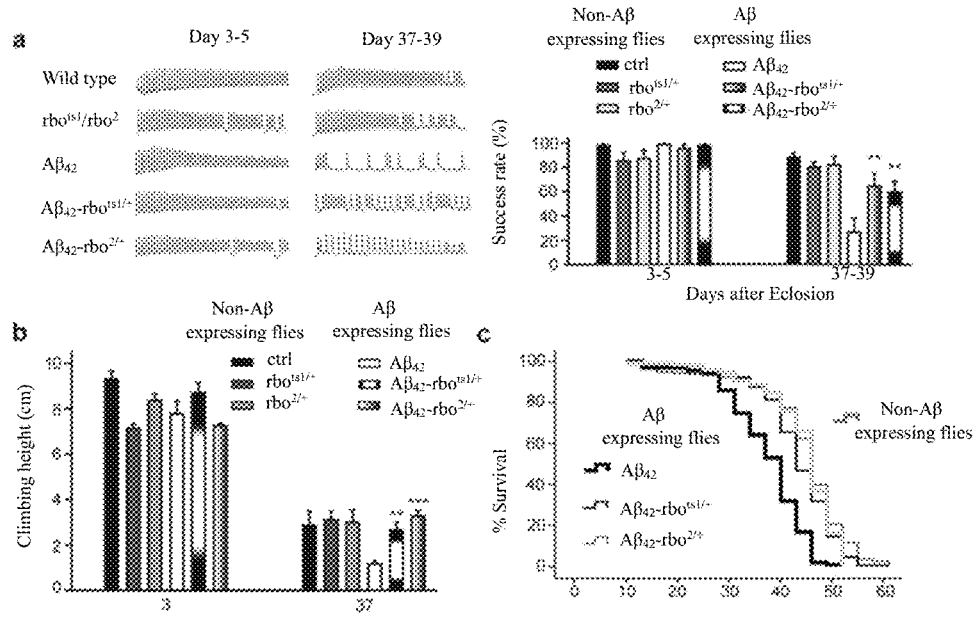
FIG. 7. rbo gene mutation ameliorates neural deficits in A$\beta_{42}$-expressing flies.

FIG. 7 shows representative records of brain stimulated EJP in different day-age in three groups of flies (FIG. 7 panel a) and quantitative analysis of success rates of elicited EJPs (FIG. 7 panel b). "ctrl" denotes wild type control flies having [Gal4]A307 transgene; "Aβ$_{42}$" denotes [Gal4]A307 [UAS]Aβ$_{42}$ double transgenic flies; "Aβ$_{42}$-rbo$^{ts1/+}$" and "Aβ$_{42}$-rbo$^{2/+}$" each denotes [Gal4]A307-rbots1/[UAS]Aβ$_{42}$ and [Gal4]A307-rbo2/[UAS]Aβ$_{42}$, respectively. It is noted that rbo mutation significantly inhibited the age dependent neuronal synaptic transmission failure caused by Aβ$_{42}$. n=6-12 for data of 3-5$^{th}$ day, and n=10~12 for data of 37-39$^{th}$ day, one-way ANOVA analysis.

In FIG. 7 panel c, rbo gene mutation ameliorated the age dependent climbing ability in Aβ$_{42}$-expressing flies, one-way ANOVA analysis was performed, n=3.

In FIG. 7 panel d, rbo gene mutation prolonged the lifespan of Aβ$_{42}$-expressing flies. n=200 flies for each group, p<0.001, Log Rank test.

Longevity assay showed that lifespan of Aβ$_{arc}$-rbo flies were longer than that of Aβ$_{arc}$ flies, although shorter than that of control and rbo flies (FIG. 1 panel d); same conclusion is obtainable by comparing mean lifespan of flies in four groups (Table 1). These results are consistent with those in the synaptic transmission examination. Further investigations on the effects of rbo gene mutation on the synaptic transmission, climbing ability, and lifespan of flies expressing wild-type Aβ$_{42}$ were conducted, and it exhibited even better improvement (FIG. 7 panels a-d).

TABLE 1

Mean lifespan of flies and comparison thereof

| Flies | Mean lifespan (days) | p value (compared to control group) | p value (compared to Aβ$_{arc}$ group) |
|---|---|---|---|
| ctrl | 47.5 | n.a. | <0.001 |
| rbo$^{ts1/+}$ | 46.2 | 0.201 | <0.001 |
| rbo$^{2/+}$ | 54.3 | <0.001 | <0.001 |
| Aβ$_{arc}$ | 27.0 | <0.001 | n.a. |
| Aβ$_{arc}$-rbo$^{ts1/+}$ | 39.9 | <0.001 | <0.001 |
| Aβ$_{arc}$-rbo$^{2/+}$ | 36.8 | <0.001 | <0.001 |

Figure 8:
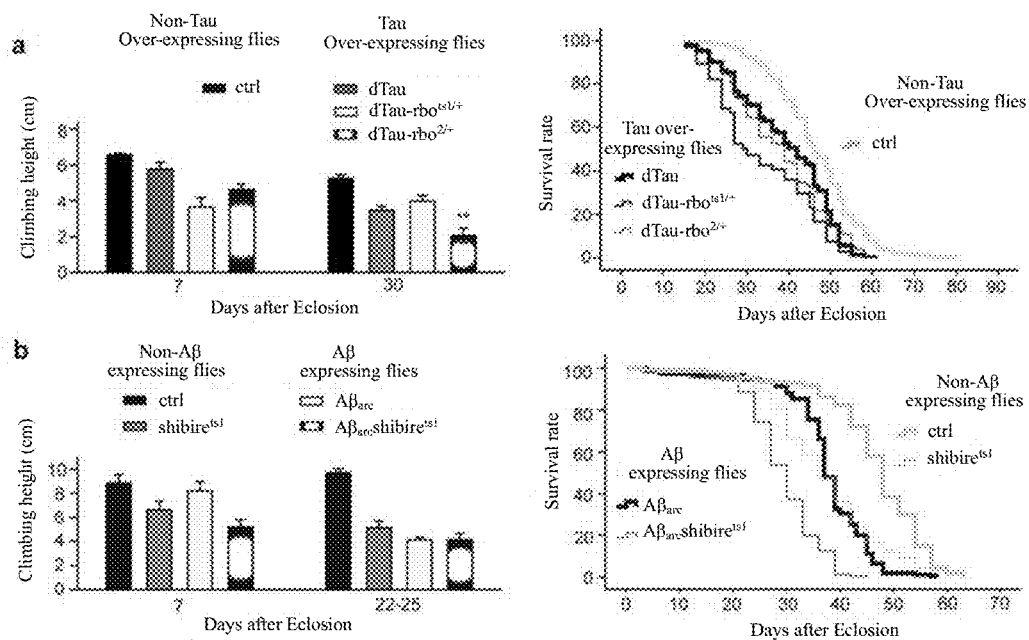
FIG. 8. Effects of rbo and shibire gene mutations on the motor ability and lifespan of flies over-expressing A$\beta_{arc}$ or *Drosophila* Tau, respectively.

FIG. 8 panel a shows the effect of rbo gene mutation on the motor defect (left) and premature death induced by *Drosophila* Tau protein over-expression in *Drosophila* giant fiber pathway. FIG. 8 panel b shows the effect of shibire gene mutation on the motor defect (left) and premature death induced by Aβ$_{arc}$ over-expression in *Drosophila* giant fiber pathway. In the longevity assay, n=100 flies for each group, Log Rank test.

The effect of rbo gene mutation against the Aβ$_{42}$ toxicity could not be ascribed to a general effect against intraneuronal accumulation of toxic proteins because rbo gene mutation could not ameliorate the lifespan shortening of flies over-expressing tau protein (FIG. 8 panel a). The effect of rbo gene mutation against the A042 toxicity could not be ascribed to a general effect potentially based on synaptic or endocytosis functions because introducing shibire gene mutation (shibire$^{ts1}$) into Aβ$_{arc}$ flies could not attenuate the premature death of Aβ$_{arc}$ flies (FIG. 8 panel b). Same as rbo$^{ts1}$ gene mutation, shibire$^{ts1}$ gene mutation also induced effects on temperature dependent synaptic transmission, bulk endocytosis, and motor ability.

With examples 1-4, the results showed that rbo gene mutation or insufficiency can specifically suppresses neural deficits in wild type and mutant Aβ$_{42}$-expressing flies.

Example 5: Deficiency or Inhibition of PI4KIIIα Enzyme which Interacts with RBO Protein Ameliorates the Neural Deficits in Aβ$_{arc}$ Flies, Tested by Immunoprecipitation Assay Immunoprecipitation and immunoblot: A total of 300 fly heads were collected and homogenized by milling in 500 μL pre-cooled Tris buffer. The formulation of Tris buffer contains: 50 mM Tris, 50 mM KCl, 1 mM EDTA, 1% cocktail protease inhibitor(Calbiochem), and pH adjusted to 7.4. Tissue homogenate was centrifuged at 10000 g for 10 min. Supernatant was collected and subjected to immunoprecipitation or immunoblot test with about 1 μg of a mouse monoclonal antibody against RBO or a rabbit polyclonal antibody against *Drosophila* PI4KIIIα. Two antibodies were generated in collaboration with Abmart (Shanghai) or with Abgent (China), respectively. RBO antibody was generated using the 251$^{th}$-500$^{th}$ amino acids of *Drosophila* subtype C RBO protein; PI4KIIIα antibody was generated using the peptide NH2-KRSNRSKRLQYQKDSYC-CONH2 (SEQ ID NO: 3). In immunoblot tests, antibodies against *Drosophila* RBO and PI4KIIIα were diluted by 1:2000. Head tissue homogenates of wild type and corresponding homozygous mutants were respectively used to detect antibodies against *Drosophila* RBO and PI4KIIIα.

Figure 9:
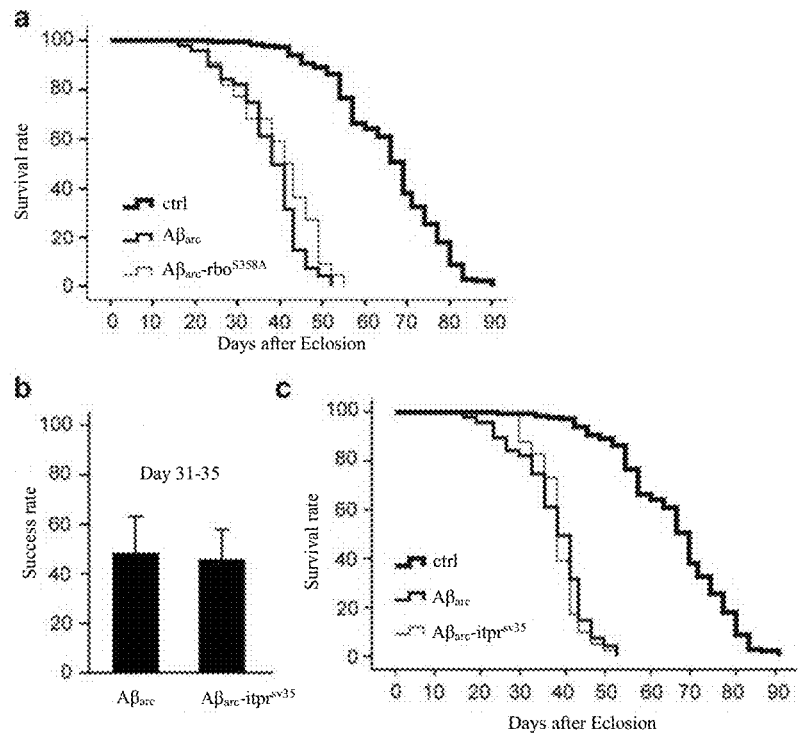
FIG. 9. Effects of rbo$^{S358A}$ and itpr$^{SV35}$ gene mutations in A$\beta_{arc}$-expressing flies.

In FIG. 9 panel a, rbo$^{S358A}$ gene mutation did not improve the lifespan of Aβ$_{arc}$-expressing flies (P=0.07).

Although RBO might be a putative diacylglycerol (DAG) lipase, and the activity of DAG lipase was reported to be increased in the hippocampus of AD patients and animal models, RBO protein might not regulate Aβ$_{arc}$ toxicity by acting as a DAG lipase because introduction of a transgene rbo$^{S358A}$ into Aβ$_{arc}$ flies could not change the premature death (FIG. 9 panel a). In RBO protein encoded by rbo$^{S358A}$ gene, a putative enzymatic active center was mutated.

FIG. 1 panel e shows a representative immunoblot of the coimmunoprecipitation of RBO protein and PI4KIIIα protein, n=3.

FIG. 1 panel f shows representative immunoblot (left) and semi-quantitative analysis (right) of RBO protein and PI4KIIIα protein levels in wild type control flies and rbo heterozygotes, n=7, one-way ANOVA analysis.

FIG. 1 panel g shows representative immunoblot (left) and semi-quantitative analysis (right) of PI4KIIIα coimmunoprecipitated with the wild-type (wtRBO) and mutant (mRBO) RBO protein, n=4, t-test analysis.

FIG. 1 panel h shows RT-PCR quantitative analysis of the PI4KIIIα mRNA expression levels in Aβ$_{arc}$, Aβ$_{arc}$-rbo$^{ts1/+}$, and Aβ$_{arc}$-rbo$^{2/+}$ flies, n=5-6, one-way ANOVA analysis.

The RBO homologs in yeast and mouse recruit PI4KIIIα and form a complex with it on cell membrane. Consistent with this, RBO protein specifically coimmunoprecipitated with Drosophila PI4KIIIα (FIG. 1 panel e). In addition, removing one copy of rbo gene (rbo$^{2/+}$) in Aβ$_{arc}$-rbo Drosophila can significantly reduce the expression levels of RBO protein and PI4KIIIα protein (FIG. 1 panel f), whereas rbo$^{ts1/+}$ gene mutation did not significantly reduce expression levels of RBO protein and PI4KIIIα protein but significantly weakened the interaction between RBO protein and PI4KIIIα protein (FIG. 1 panel g). Notably, neither of the two rbo mutations changed the transcription of PI4KIIIα gene (FIG. 1 panel h).

To test whether PI4KIIIα plays a similar role as RBO protein in neural deficits of Aβ$_{arc}$ flies, a chromosomal deficiency (deletion of a PI4KIIIα-containing DNA segment of a chromosome, pi4k$^{def/+}$) and a nonsense mutation of PI4KIIIα (PI4KIIIα$^{GS27/+}$) was separately introduced to Aβ$_{arc}$-expressing flies.

Figure 2:
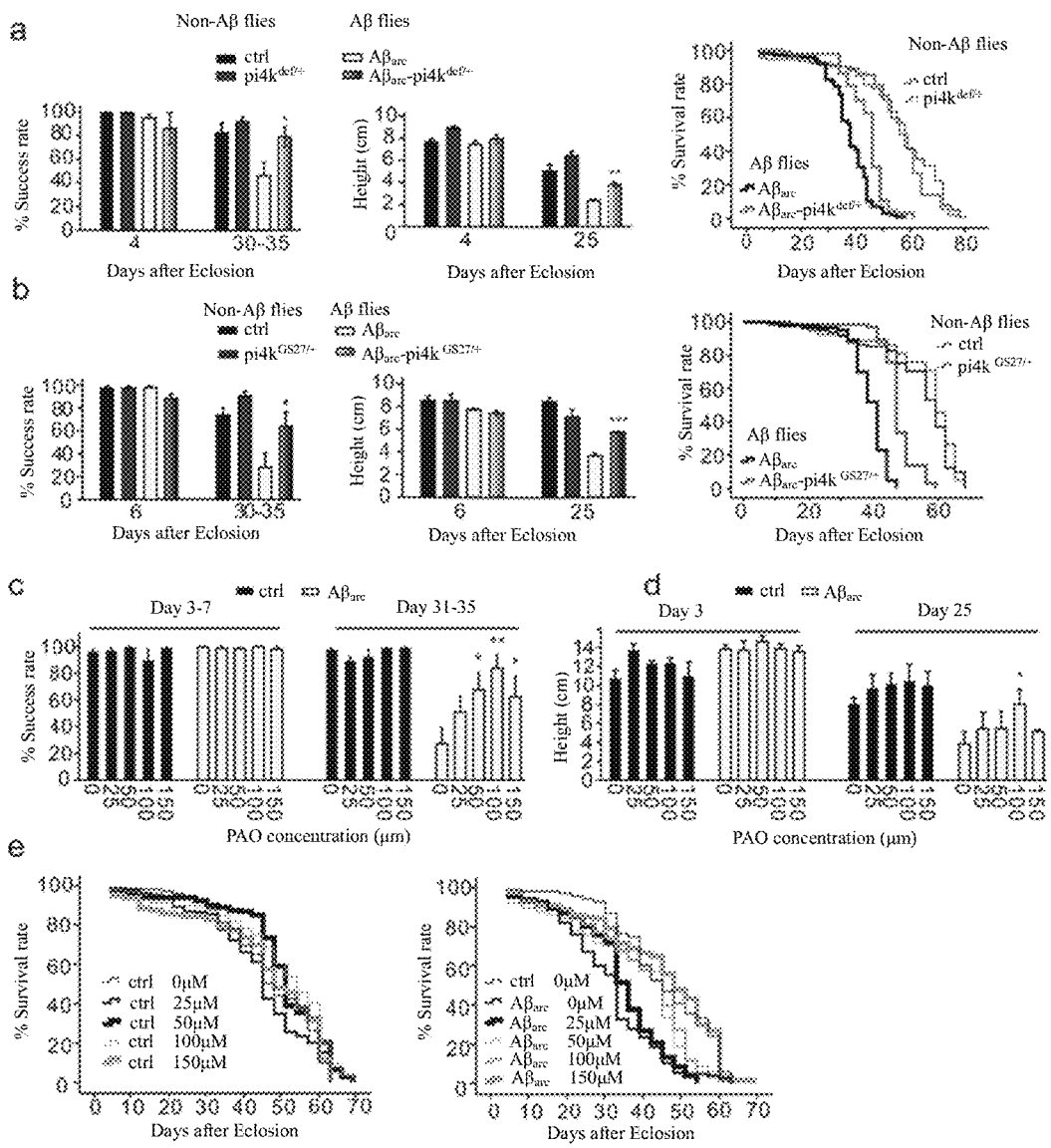
FIG. 2. Down-regulation or pharmaceutical inhibition of PI4KIIIα protein expression level ameliorates neural deficits in A$\beta_{arc}$-expressing flies.

FIG. 2 shows that the synaptic transmission, motor function, and premature death were suppressed by the heterozygous PI4KIIIα gene deletion (PI4KIIIα$^{def/+}$) (see FIG. 2 panel a) or the nonsense mutation (PI4KIIIα$^{GS27/+}$) (see FIG. 2 panel b), as well as were suppressed by PAO (FIG. 2 panels c-e). "ctrl" denotes wild type control flies having [Gal4]A307 transgene; "PI4KIIIα$^{def/+}$" and "PI4KIIIα$^{GS27/+}$" denotes PI4KIIIα$^{def/+}$ and PI4KIIIα$^{GS27/+}$ heterozygous flies having one copy of [Gal4]A307 transgene; "Aβ$_{arc}$" denotes [Gal4]A307 [UAS]A-$_{arc}$ double transgenic flies; "Aβ$_{arc}$-PI4KIIIα$^{def/+}$" and "Aβ$_{arc}$-PI4KIIIα$^{GS27/+}$" each denotes PI4KIIIα$^{def/+}$; [Gal4]A307/[UAS]Aβ$_{arc}$ and PI4KIIIα$^{GS27}$+; [Gal4]A307 [UAS]Aβ$_{arc}$, respectively. For EJP data recording in each group, n=6~10. For each climbing assay, n=3~5. For lifespan data of each fly strain, n=100~200, P value less than 0.001. The statistical analysis methods are as described above.

In fact, experimental results demonstrated that such PI4KIIIα mutations suppressed the Aβ$_{arc}$ induced defects in synaptic transmission, motor function, and lifespan (FIG. 2 panels a-b). Consistently, feeding Aβ$_{arc}$ flies with PI4KIIIα inhibitor PAO also significantly ameliorated these defects in a dose-dependent manner (FIG. 2 panels c-e).

In FIG. 9 panel b, itpr$^{SV35}$ gene mutation did not improve the synaptic transmission or lifespan of Aβ$_{arc}$-expressing flies (P=0.13). In the longevity assay, n=100 flies for each group, Log Rank test. In the success rate analysis of elicited EJP, n=5.

However, the suppression of the neural deficits by downregulating RBO/PI4KIIIα could not attribute to a toxicity effect caused by an attenuation of calcium release mediated by phospholipase C, PI$_{4,5}$P and the receptor of inositol triphosphate (IP3R) because introducing a nonsense mutation of the gene encoding IP3R into Aβ$_{arc}$-expression flies could not attenuate the synaptic failure or the premature death (FIG. 9 panels b-c).

Example 6: Down-Regulation of RBO/PI4KIIIα Decreases Intracellular Aβ$_{42}$ Accumulation, Detected by Staining and Imaging Staining and imaging: Central nervous system of Drosophila was stained as followed. The whole central nervous system (CNS) of flies, including the brain and ventral ganglion, was dissected out in cold PBS and fixed with 4% PFA in PBS for about 45 min. Preparations were washed with PBS for 30 min, treated with formic acid (70% in water) for 45 min to reexpose the antigenic determinant, washed repetitively with 5% BSA in PBS solution supplemented with 0.25% Triton, incubated with primary antibody (6E10, 1:100 dilution) at 4° C. for 10-12 h, washed with PBS again, and finally incubated with cy3-conjugated secondary antibody (Jackson ImmunoResearch Laboratories, 1:200 dilution) at room temperature for 2 h. Images were taken under Nikon A1R-A1 confocal microscope; the genotypes of fly CNS were blind to the imaging personnel.

Figure 3:
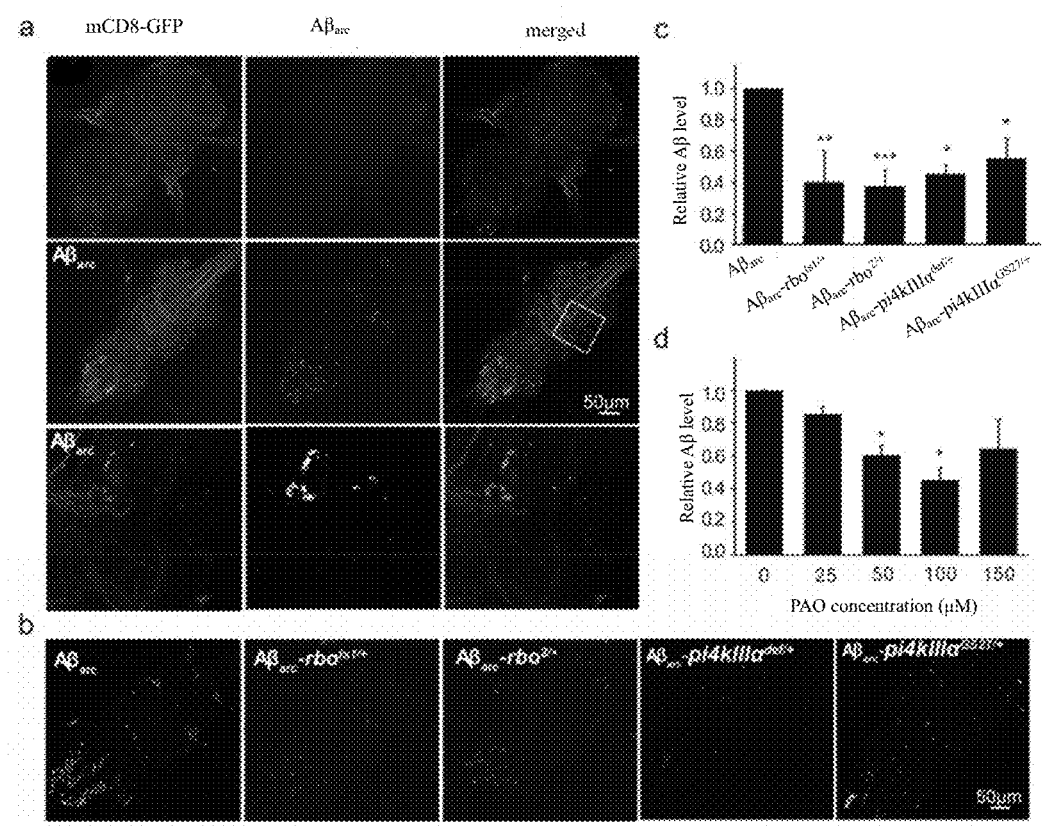
FIG. 3. Down-regulation of RBO/PI4KIIIα protein expression level or function reduces intraneuronal Aβ accumulation.

FIG. 3 panel a shows confocal images of whole-mount Aβ staining of the ventral ganglion in control flies expressing mCD8-GFP (top row) and Aβ$_{arc}$-expressing flies (middle row) of 21-25 day-age; the expression of mCD8-GFP and Aβ$_{arc}$ were both driven by [Gal4]A307. Each group of staining was repeated twice; bottom row represents an enlarged view of the region defined by the square in the middle row. FIG. 3 panel b shows representative confocal images of whole-mount Aβ staining of the ventral ganglion of Aβ$_{arc}$, Aβ$_{arc}$-rbo$^{ts1/+}$, Aβ$_{arc}$-rbo$^{2/+}$, Aβ$_{arc}$-PI4KIIIα$^{def/+}$, and Aβ$_{arc}$-PI4KIIIα$^{GS27}$ flies of 21-25 day-age with each group of staining repeated twice; while FIG. 3 panel c (top) shows head Aβ level quantified by ELISA method. FIG. 3 panel c (bottom) shows head Aβ level in Aβ$_{arc}$-expressing flies with PAO treatment at different concentrations, quantified by ELISA method. n=3-5 for each group of data in ELISA quantification assay, one-way ANOVA analysis. In FIG. 3 panels a-b, the scale bar represents 50 μm.

Previously, neuronal damage induced by Aβ$_{arc}$-expression in GF pathway was attributed to intracellular accumulation Aβ protein. Here, we further confirmed the intraneuronal accumulation of Aβ by introducing uas-mCD8-gfp transgene into Aβ$_{arc}$ flies. uas-mCD8-GFP expresses mCD8-GFP fluorescent protein, which targets the plasma membrane and was driven by the same driver as that of Aβ$_{arc}$, so that the Aβ$_{arc}$-expressing neurons could be labeled with GFP. Confocal imaging revealed that Aβ immunostaining signal colocalized with GFP signal (FIG. 3 panel a), demonstrating the phenomenon of intraneuronal Aβ accumulation in this fly model.

To analyze whether RBO/PI4KIIIα insufficiency affects intracellular Aβ accumulation, Aβ immunostaining was performed in Aβ$_{arc}$, Aβ$_{arc}$-rbo, and Aβ$_{arc}$-PI4KIIIα flies. It is found that immunostaining signal of Aβ$_{arc}$-rbo and Aβ$_{arc}$-PI4KIIIα flies significantly decreased as compared to that of Aβ$_{arc}$ flies (FIG. 3 panel b).

Example 7: Down-Regulation of RBO/PI4KIIIα Decreases Intracellular Aβ$_{42}$ Accumulation, Detected by ELISA Quantitative Analysis ELISA method analysis: ELISA was performed using Aβ$_{42}$ Human ELISA Kit (Invitrogen) according to the manufacturer's specifications. To analyze Aβ$_{42}$ level in CNS, intact brains of 25 flies per strain were dissected out in cold PBS and placed immediately into cold ELISA sample dilution buffer supplemented with cocktail protease inhibitor (Calbiochem). Brains were homogenized thoroughly, incubated at room temperature for 4 h, and stored under −20° C.

Similar as in Example 6, ELISA quantitative analysis shows that the amount of Aβ$_{42}$ was significantly decreased in Aβ$_{arc}$-rbo flies, Aβ$_{arc}$-PI4KIIIα flies, and Aβ$_{arc}$ flies after PAO treatment (FIG. 3 panels c and d).

Figure 10:
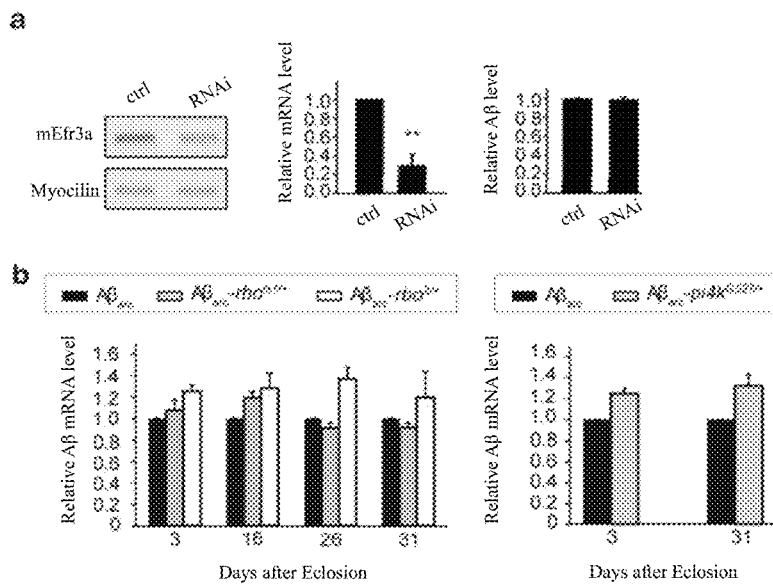
FIG. 10. Effects of Efr3a gene knockdown on endocytosis of extracellular Aβ of N2a cells, and effects of rbo and PI4KA gene mutations on A$\beta_{arc}$ transcription in A$\beta_{arc}$-expressing flies.

FIG. 10 panel a shows representative images of knockdown efficiency of EFR3a gene (left) and normalized quantification (middle) in N2 cells by RT-PCR method, right image illustrates that EFR3a gene knockdown does not affect endocytosis of extracellular Aβ of N2a cells. The sequence used for constructing Efra knockdown RNAi is 5'-AGGTATCATTCAGGTTCTGTT-3' (SEQ ID NO: 4). FIG. 10 panel b shows that rbo and PI4KIIIα gene mutations do not decrease Aβ$_{arc}$ transcription level in Aβ$_{arc}$-expressing flies by RT-PCR method.

With Examples 6-7, it is demonstrated that decreasing of intraneuronal Aβ accumulation induced by RBO/PI4KIIIα down-regulation is unlikely due to reduction of intake of extracellular Aβ$_{42}$. The reasons are: 1) intake of extracellular Aβ$_{42}$ in N2a cells having rbo homolog gene knockdown does not reduce significantly (FIG. 10 panel a); 2) Aβ$_{arc}$ mRNA expressing levels in Aβ$_{arc}$-rbo and Aβ$_{arc}$-PI4KIIIα flies of different age are not reduced as compared to Aβ$_{arc}$ flies in the experiment group (FIG. 10 panel b).

Example 8: Solution Preparation and Toxicity Examination of PI4KIIIα Inhibitors PAO, A1 and G1

HEK293 cells, *Drosophila* larva, and adult flies were treated with PAO or A1, stock solutions of 10 mM and 0.9 mM A1 was made separately by dissolving PAO powder (Sigma-Aldrich, CAS NO. 637-03-6) and A1 powder in DMSO. Then gradiently diluted with distilled water to the desired concentrations; the final concentration of DMSO was adjusted to identical level to ensure the experimental results were not influenced by DMSO variation.

To test the toxicity of PAO on living flies, we cultured wild type flies with fly food containing 50, 100, 200, 300, 400, and 600 μM PAO, started from embryonic stage. It is found that PAO treatment at 200 μM or less neither changed the eclosion rate nor altered the climbing ability after eclosion. Thus 25, 50, 100, and 150 μM PAO were chosen for culturing Aβ$_{arc}$ and control flies.

To test the toxicity of PAO on dissected *Drosophila* third instar larvae, Schneider's culture medium containing 50, 100, 200, 300, 400, and 500 nM PAO were used to incubate dissected *Drosophila* third instar larvae at 25° C. overnight. It is found that salivary gland cells and CNS neurons in the larvae treated with PAO at 300 nM or more turned white, reflecting damage, whereas no such effect with PAO at 150 nM or less. Thus 50, 100, and 150 nM PAO were chosen for culturing.

To test the toxicity of PAO and A1 on HEK293T cells, DMEM culture medium containing 50, 100, 200, 300, 400, and 600 nM PAO or A1 were used to incubate HEK239 cells for 12 h. According to MTT tests, it is found that PAO or A1 at 250 nM or more killed most of the cells, whereas no such effect at 150 nM or less. Thus 25, 50, 100, and 150 nM PAO or A1 were chosen for culturing.

To test the toxicity of PAO oral gavage on mice, PAO powder was dissolved in DMSO to prepare a stock solution of 30 mg/mL. Then gradiently diluted with distilled water to the desired concentrations; the final concentration of DMSO was adjusted to identical level to ensure the experimental results were not influenced by DMSO variation. C57BL/6 mice of 3 month-age were subjected to gavage at doses of 18, 10 and 6 mg/kg body weight, two mice for each dose level. All mice were found dead on the second day. Then mice were subjected to gavage at doses of 4.5 and 2.0 mg/kg body weight, five mice for each dose level. With respect to 4.5 mg/kg body weight dose, gavage once a day for five consecutive days, four mice out of five survived. With respect to 2.0 mg/kg body weight dose, gavage once a day every Monday through Friday, no gavage on weekends. After two consecutive weeks, all five mice survived. Therefore, with respect to C57/B6 mice, median lethal dose of PAO gavage is 2-6 mg/kg body weight, approximately 4 mg/kg body weight. Thus 0.1, 0.3 and 1.0 mg/kg body weight doses were chosen for PAO gavage in APP/PS1 mice and control mice, gavage once a day every Monday through Friday, no gavage on weekends, for six consecutive weeks.

Example 9: Down-Regulation of RBO/PI4KIIIα Facilitates Aβ$_{42}$ Secretion, Detected by Culturing of Aβ-Expressing Larvae Tissue Culturing of Aβ-expressing larvae tissue: Third instar larvae were washed with water and sterilized with 70% alcohol for 2 min, and were dissected along the dorsal middle line in Schneider's (Sigma) culture medium. The tracheal, gut, and fat body of larvae were removed with caution. The dissected larvae were washed with Schneider's culture medium and transferred into 2 mL centrifuge tube containing 150 μL Schneider's culture medium supplemented with gentamycin (20 mg/mL). Each tube contained 5 dissected larvae. The centrifuge tubes were placed in a humid and dark environment at 25° C. for 8 h. Then 100 μL was taken from each tube and was used for ELISA quantification of Aβ$_{42}$. ELISA was performed using Aβ$_{42}$ Human ELISA Kit (Invitrogen).

Figure 4:
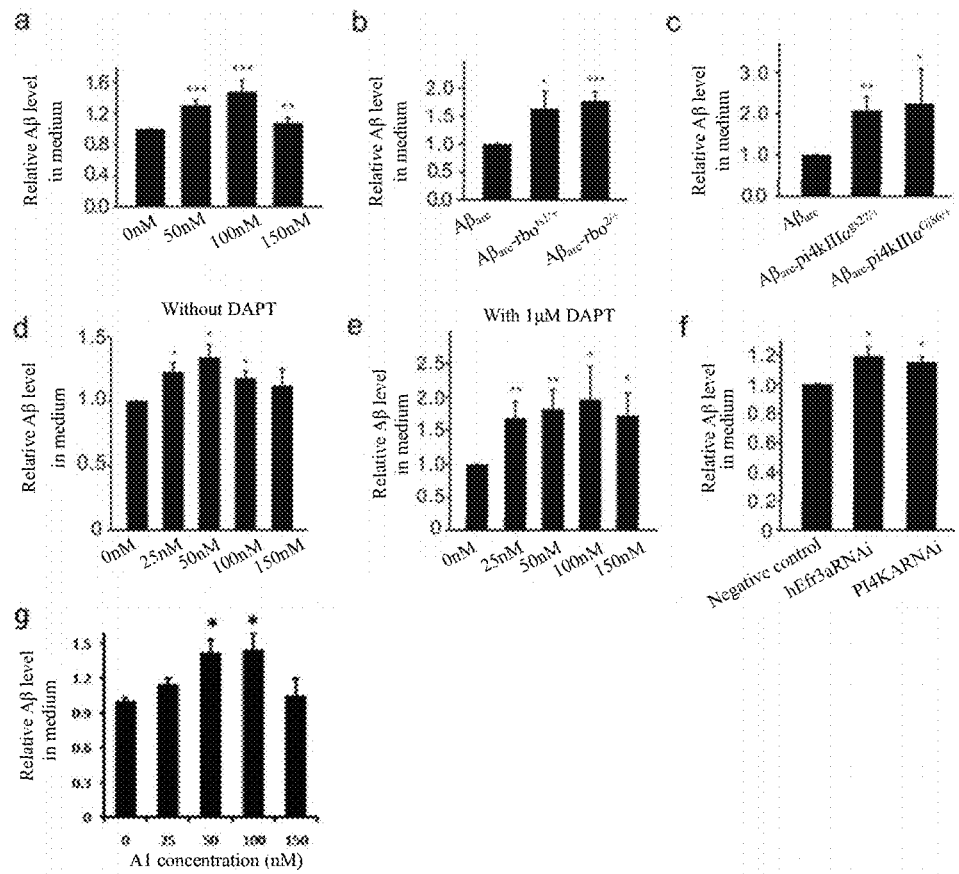
FIG. 4. Down-regulation of RBO/PI4KIIIα protein expression level or function facilitates A$\beta_{42}$ secretion.

In FIG. 4, panels a-c show normalized quantification of A1342 levels in media incubating dissected Aβ$_{arc}$-expressing third instar *Drosophila* larvae with PAO treatment at different concentration, rbo and PI4KIIIα gene mutations.

To investigate the mechanism of PAO treatment and RBO/PI4KIIIα insufficiency decreasing intraneuronal Aβ accumulation, Aβ$_{42}$ secretion while incubation of dissected sample of Aβ$_{arc}$-expressing third instar larvae in Schneider's culture medium was detected. ELISA assay shows that PAO treatment facilitates Aβ$_{42}$ secretion and exhibits a tendency of drug dose dependency (FIG. 4 panel a), which demonstrates that inhibition of PI4KIIIα enzyme activity facilitates Aβ$_{42}$ secretion. Consistently, compared with the medium culturing the dissected Aβ$_{arc}$ larvae, Aβ$_{42}$ concentrations in media culturing the Aβ$_{arc}$-rbo and Aβ$_{arc}$-PI4KIIIα larvae increase significantly (FIG. 4 panels b-c).

Example 10: Down-Regulation of RBO/PI4KIIIα Facilitates Aβ$_{42}$ Secretion, Detected by Culturing of Human-Derived APP-Expressing HEK293T Cells Culturing of human-derived APP-expressing HEK293T cells: HEK293T cells stably transfected with human APP (here named as HEK293T-APP cells) were cultured in DMEM (Hyclone) supplemented with 10% FBS (Gibco), penicillin, streptomycin, and G418 (100 μg/mL). Recombinant plasmid pSUPER.basic-expressing shRNA of target genes were transiently transfected into HEK293T using Lipofectamine™ 2000 (Invitrogen). Cells were incubated for two days after transfection, followed with subsequent experiments. For ELISA quantification of Aβ$_{42}$ concentration in culture medium, freshly-changed culture medium was examined after culturing cells for 12 h.

Assay of activities of α, β, and γ secretase of APP and APP expression level in HEK293T-APP cells: HEK293T-APP cells were incubated in 12-well plate, culture fluids contained PAO at concentrations of 0, 25, 50, 100, or 150 nM. After 6-8 hours incubation, same amounts of cells were collected separately. To analyze secretase activities, cells were lysed separately with 500 μL of TBS buffer, centrifuged for 15 min, supernatants were collected and precipitates were resuspended with 500 μL of TBS buffer. To analyze the activities of α and β secretases, 100 μL supernatant was mixed with 2× reaction solution (50 mM Tris- HCl, pH 6.8, 4 mM EDTA, 0.5% CHAPSO (w/v)) containing 10 μM of specific fluorogenic substrates of α or β secretase (Calbiochem, Cat. No. 565767/565758); to analyze activity of γ secretase, 100 μL resuspended solution was mixed with 2× reaction solution (50 mM Tris-HCl, pH 6.8, 4 mM EDTA, 0.5% CHAPSO (w/v)) containing 10 μM of specific fluorogenic substrates of γ secretase (Calbiochem, Cat. No. 565764). After reacting at 37° C. for 30 min, analyze with microplate reader (excitation/emission: 365/490 nm for α/β enzyme activity, 365/440 for γ enzyme activity).

When analyzing the expression level of APP, Western Blotting was performed using anti-APP/Aβ antibody (6E10) on collected cells after lysed with TBS buffer containing protease inhibitor (1% cocktail, invitrogen).

Figure 14:
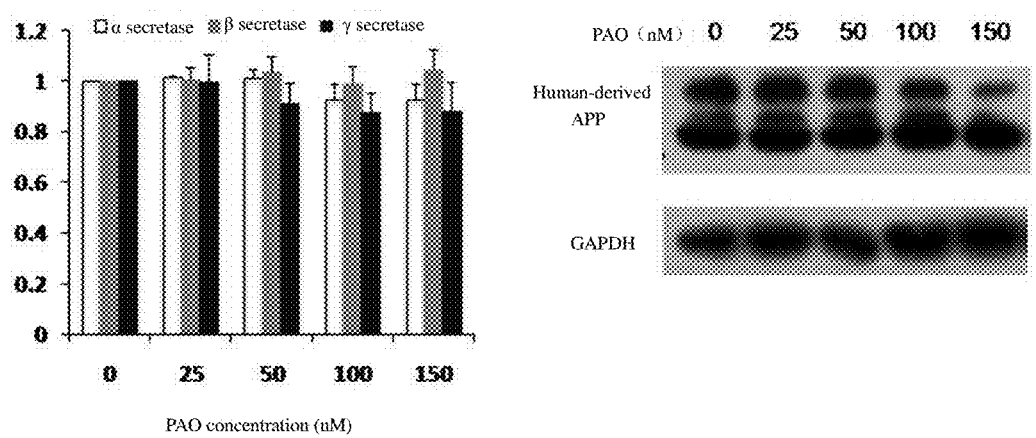
FIG. 14. Effects of PAO on APP expression level and activities of α, β, and γ secretase.

FIG. 14 panel a shows the normalized quantification of the effects of PAO on the activities of α, β, and γ secretase of HEK293T-APP cells, n=5 for each data point, one-way ANOVA analysis; FIG. 14 panel b shows representative immunoblot showing APP-APP cells after PAO treatment at different concentrations, the experiments were repeated for 3 times or more.

Figure 16:
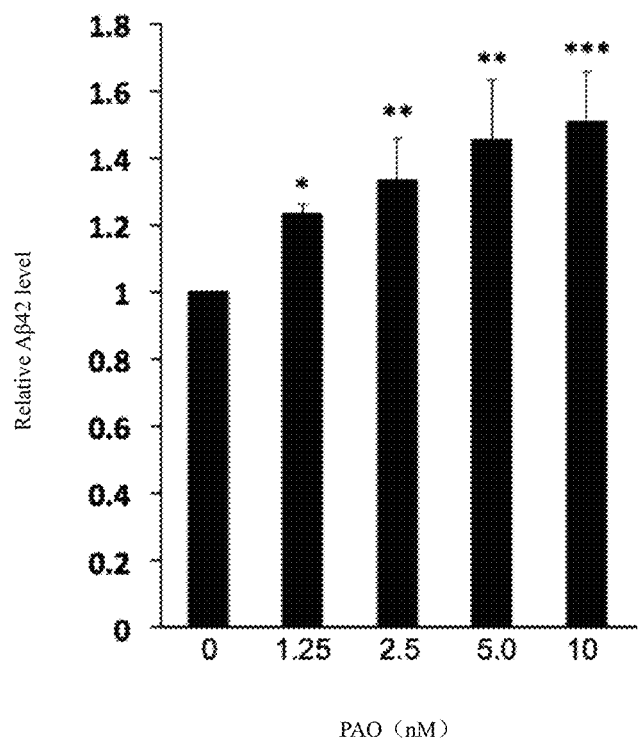
FIG. 16. Concentration dependency of facilitation effect of PAO on $A\beta_{42}$ secretion from HEK293T stably transfected with APP.

To detect whether such facilitation affect the secretion of $A\beta_{42}$ derived from cleavage of β amyloid precursor protein (APP), $A\beta_{42}$ secretion of HEK293T-APP cells was tested. FIG. 4, panels d-g show normalized quantification of $A\beta_{42}$ levels in media incubating HEK293T-APP cells with PAO and A1 treatment at different concentration, EFR3a and PI4KA knockdown. In fact, PAO treatment in culture medium has similar effect in increasing $A\beta_{42}$ concentration in culture medium (FIG. 4 panel d), and PAO even increases $A\beta_{42}$ concentration in culture medium under the presence of DAPT (1 μM), which is a γ secretase inhibitor (FIG. 4 panel e). Notably, PAO still has a stable effect even when PAO concentration is quite low (as low as 1.0 nM) (FIG. 16). Further, knockdown of EFR3a or PI4KA gene or applying A1 treatment in HEK293T-APP cells can significantly increase $A\beta_{42}$ concentration in culture medium (FIG. 4 panels f-g). n=4~15 for each group of data, one-way ANOVA analysis.

PAO and PAO derivatives were analyzed according to $A\beta_{42}$ secretion detected in HEK293T-APP cells, and the following results were obtained as listed in Table 2.

TABLE 2

| PAO, PAO derivatives, and activities thereof | | | | |
| --- | --- | --- | --- | --- |
| No. | Chemical structure | Name | Mw | Activity |
| 1 | | oxo(phenyl)arsane | 168.0 | +++ |
| 2 | | oxo(o-tolyl)arsane | 182.1 | + |
| 3 | | (3-methoxyphenyl)(oxo)arsane | 198.15 | + |
| 4 | | oxo(4-(trifluoromethyl)phenyl)arsane | 236.0 | ++ |
| 5 | | (4-fluorophenyl)(oxo)arsane | 186.0 | ++ |
| 6 | | 4-(oxoarsanyl)aniline (PAPAO) | 183.0 | ++ |

TABLE 2-continued

PAO, PAO derivatives, and activities thereof

| No. | Chemical structure | Name | Mw | Activity |
|---|---|---|---|---|
| 7 | 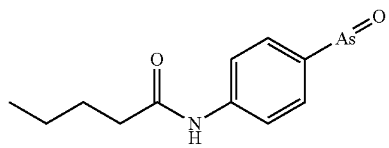 | N-(4-(oxoarsanyl)phenyl) pentanamide | 267.2 | + |
| 8 | 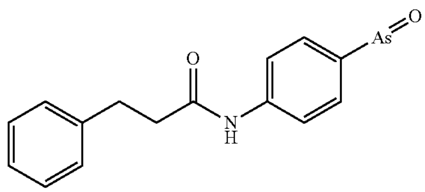 | N-(4-(oxoarsanyl)phenyl)-3-phenylpropanamide | 315.2 | + |
| 9 | 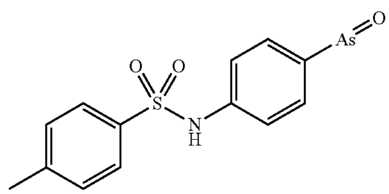 | 4-methyl-N-(4-(oxoarsanyl) phenyl)benzenesulfonamide | 337.2 | + |
| 10 | 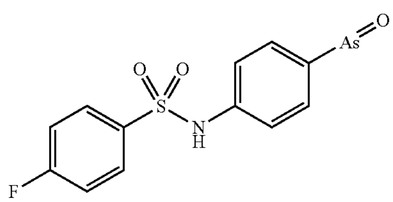 | 4-fluoro-N-(4-(oxoarsanyl) phenyl)benzene-sulfonamide | 341.2 | + |
| 11 | 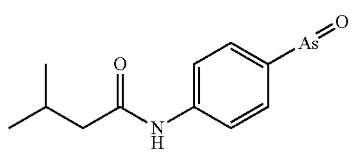 | 3-methyl-N-(4-(oxoarsanyl) phenyl)butanamide | 267.2 | + |
| 12 | 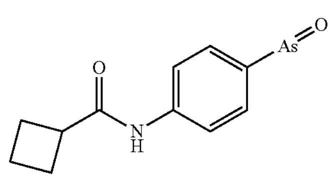 | N-(4-(oxoarsanyl)phenyl) cyclobutanecarboxamide | 265.1 | + |
| 13 | 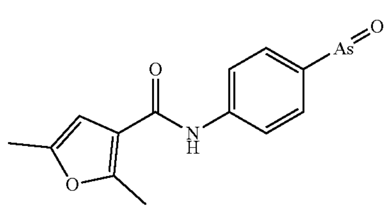 | 2,5-dimethyl-N-(4-(oxo-arsanyl)phenyl)furan-3-carboxamide | 305.2 | + |
| 14 | 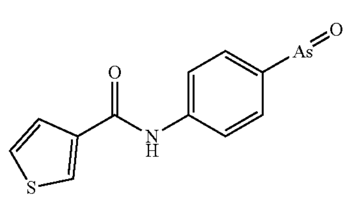 | N-(4-(oxoarsanyl)phenyl) thiophene-3-carboxamide | 293.2 | + |

TABLE 2-continued

| | PAO, PAO derivatives, and activities thereof | | | |
|---|---|---|---|---|
| No. | Chemical structure | Name | Mw | Activity |
| 15 | | 1-(4-(oxoarsanyl)phenyl)-3-(pyridin-3-yl)urea | 303.2 | + |
| 16 | | 1-(cyclopropylmethyl)-3-(4-(oxoarsanyl)phenyl)urea | 280.2 | + |
| 17 | | 1-cyclohexyl-3-(4-(oxoarsanyl)phenyl)urea | 308.2 | + |
| 18 | | N-(4-arsorylphenyl)acetamide | 225.0 | + |
| 19 | | N-(4-arsorylphenyl)propionamide | 239.0 | + |
| 20 | | ethyl(4-arsorylphenyl)carbamate | 255.0 | + |
| 21 | | methyl 4-((4-arsorylphenyl)amino)-4-oxobutanoate) | 297.0 | + |
| 22 | | N-(4-arsorylphenyl)cyclopentanecarboxamide | 279.0 | + |
| 23 | | but-3-yn-1-yl (4-arsorylphenyl)carbamate | 279.0 | + |

TABLE 2-continued

PAO, PAO derivatives, and activities thereof

| No. | Chemical structure | Name | Mw | Activity |
|---|---|---|---|---|
| 24 | 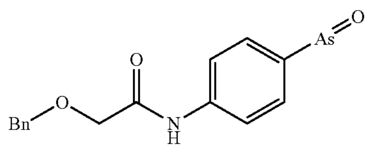 | N-(4-arsorylphenyl)-2-(benzyloxy)acetamide | 331.0 | + |
| 25 | 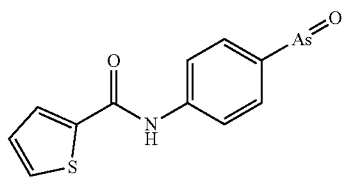 | N-(4-arsorylphenyl)thiophene-2-carboxamide | 292.9 | + |
| 26 | 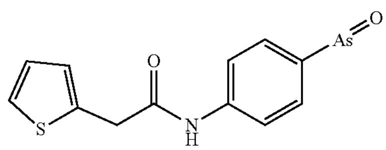 | N-(4-arsorylphenyl)-2-(thiophen-2-yl)acetamide | 307.0 | + |
| 27 | 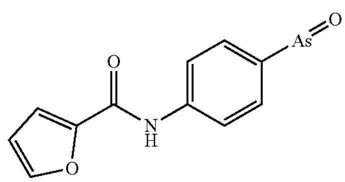 | N-(4-arsorylphenyl)furan-2-carboxamide | 277.0 | + |
| 28 | 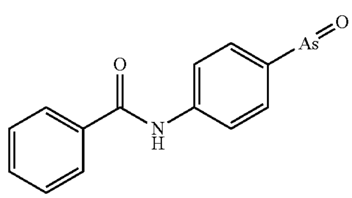 | N-(4-arsorylphenyl)benzamide | 287.0 | ++ |
| 29 | 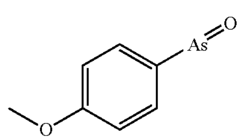 | (4-methoxyphenyl)(oxo)arsine | 198.0 | ++ |
| 30 | 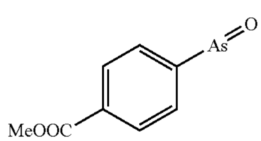 | methyl 4-arsorylbenzoate | 226.0 | + |
| 31 | 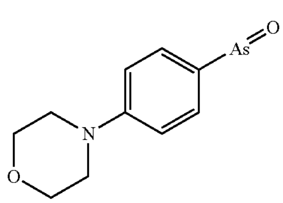 | 4-(4-arsorylphenyl)morpholine | 253.0 | + |
| 32 | 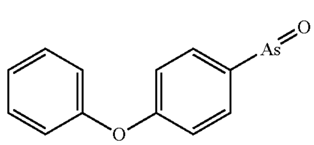 | oxo(4-phenoxyphenyl)arsine | 260.0 | + |

TABLE 2-continued

PAO, PAO derivatives, and activities thereof

| No. | Chemical structure | Name | Mw | Activity |
|---|---|---|---|---|
| 33 | 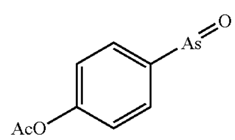 | 4-arsorylphenyl acetate | 226.0 | ++ |
| 34 | 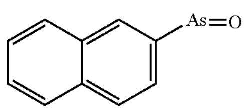 | naphthalen-2-yl(oxo)arsine | 218.0 | ++ |
| 35 | 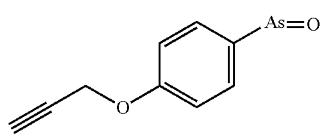 | oxo(4-(prop-2-yn-1-yloxy)phenyl)arsine | 222.0 | + |
| 36 | 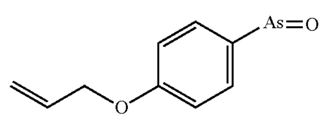 | oxo(4-(prop-2-yn-1-yloxy)phenyl)arsine | 224.0 | + |
| 37 | 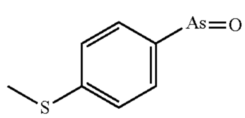 | (4-(methylthio)phenyl)(oxo)arsine | 213.9 | + |
| 38 | 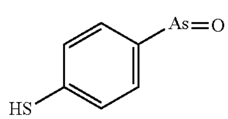 | 4-arsorylbenzenethiol | 199.9 | + |
| 39 | 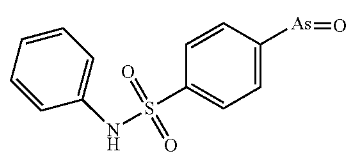 | 4-arsoryl-N-phenyl-benzenesulfonamide | 323.0 | + |
| 40 | 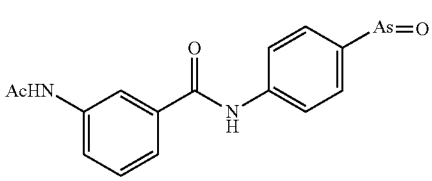 | 3-acetamido-N-(4-arsoryl-phenyl)benzamide | 344.0 | + |
| 41 | 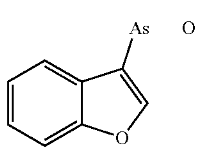 | benzofuran-3-yl(oxo)arsine | 208.0 | + |
| 42 | 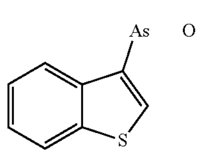 | benzo[b]thiophen-3-yl(oxo)arsine | 224.0 | + |

TABLE 2-continued

PAO, PAO derivatives, and activities thereof

| No. | Chemical structure | Name | Mw | Activity |
|---|---|---|---|---|
| 43 | 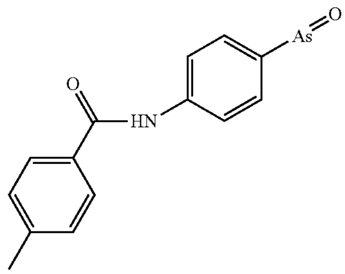 | N-(4-arsorylphenyl)-4-methylbenzamide | 301.0 | + |
| 44 | 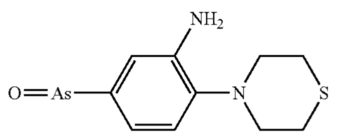 | 5-arsoryl-2-thiomorpholino-aniline | 284.0 | + |
| 45 | 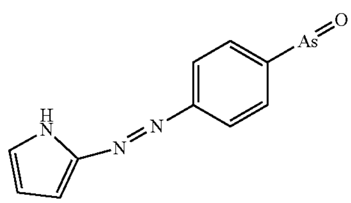 | 2-((4-arsorylphenyl)diazenyl)-1H-pyrrole | 261.0 | + |
| 46 | 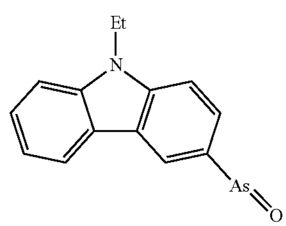 | 3-arsoryl-9-ethyl-9H-carbazole | 285.0 | + |
| 47 | 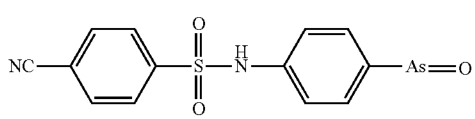 | N-(4-arsorylphenyl)-4-cyanobenzenesulfonamide | 335.9 | + |
| 48 | 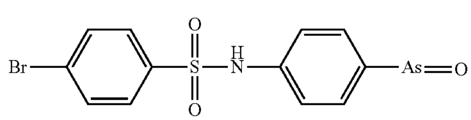 | N-(4-arsorylphenyl)-4-bromobenzene-sulfonamide | 400.9 | + |
| 49 | 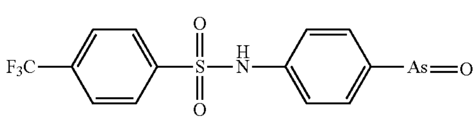 | N-(4-arsorylphenyl)-4-(trifluoromethyl)benzene sulfonamide | 300.9 | + |
| 50 | 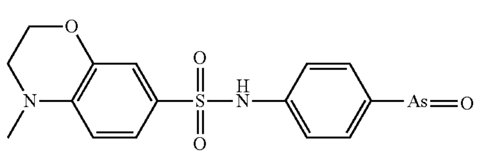 | N-(4-arsorylphenyl)-4-methyl-3,4-dihydro-2H-benzo[b][1,4]oxazine-7-sulfonamide | 394 | + |
| 51 | 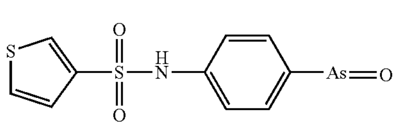 | N-(4-arsorylphenyl)thiophene-3-sulfonamide | 328.9 | + |

TABLE 2-continued

PAO, PAO derivatives, and activities thereof

| No. | Chemical structure | Name | Mw | Activity |
|---|---|---|---|---|
| 52 | 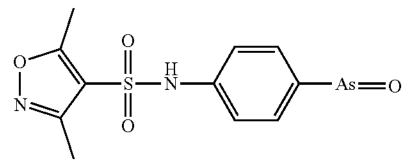 | N-(4-arsorylphenyl)-3,5-dimethylisoxazole-4-sulfonamide | 342.0 | + |
| 53 | 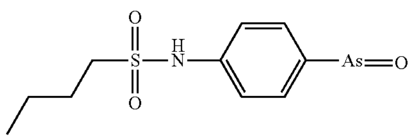 | N-(4-arsorylphenyl) butane-1-sulfonamide | 303.0 | + |
| 54 | 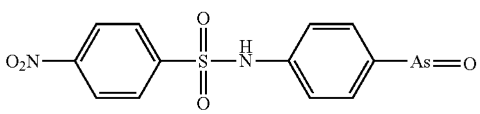 | N-(4-arsorylphenyl)-4-nitrobenzenesulfonamide | 367.9 | + |
| 55 | 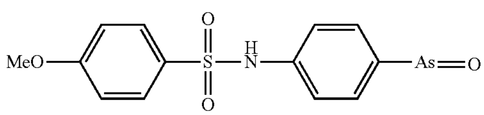 | N-(4-arsorylphenyl)-4-methoxybenzenesulfonamide | 353.0 | + |
| 56 | 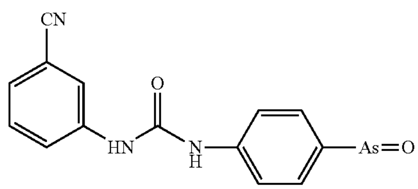 | 1-(4-arsorylphenyl)-3-(3-cyanophenyl)urea | 327.0 | + |
| 57 | 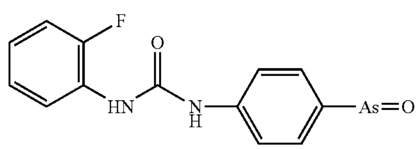 | 1-(4-arsorylphenyl)-3-(2-fluorophenyl)urea | 320.0 | + |
| 58 | 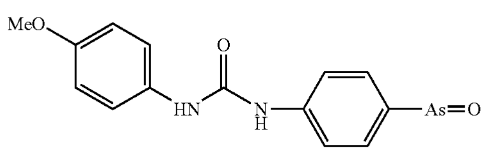 | 1-(4-arsorylphenyl)-3-(4-methoxyphenyl)urea | 332.0 | + |
| 59 | 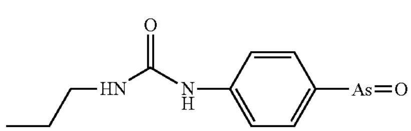 | 1-(4-arsorylphenyl)-3-propylurea | 368.0 | + |
| 60 | 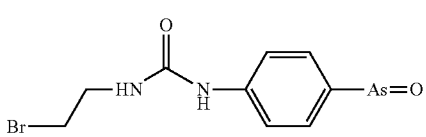 | 1-(4-arsorylphenyl)-3-(2-bromoethyl)urea | 331.9 | + |
| 61 | 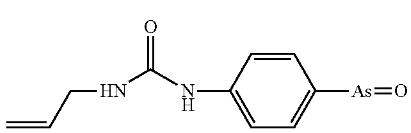 | 1-allyl-3-(4-arsorylphenyl)urea | 266.0 | + |

TABLE 2-continued

PAO, PAO derivatives, and activities thereof

| No. | Chemical structure | Name | Mw | Activity |
|---|---|---|---|---|
| 62 | 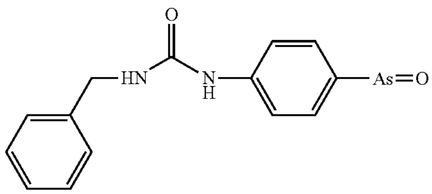 | 1-(4-arsorylphenyl)-3-benzylurea | 316.0 | + |
| 63 | 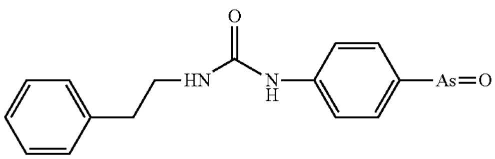 | 1-(4-arsorylphenyl)-3-phenethylurea | 330.0 | + |
| 64 | 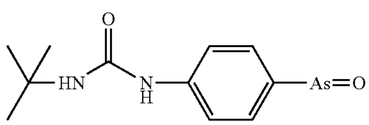 | 1-(4-arsorylphenyl)-3-(tert-butyl)urea | 282.0 | + |
| 65 | 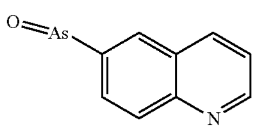 | 6-arsorylquinoline | 219.0 | + |
| 66 | 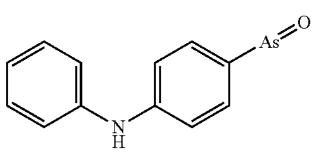 | 4-arsoryl-N-phenylaniline | 259.0 | + |
| 67 | 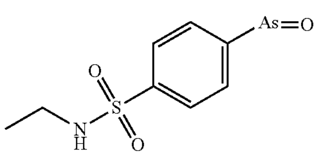 | 4-arsoryl-N-ethylbenzene-sulfonamide | 275.0 | + |
| 68 | 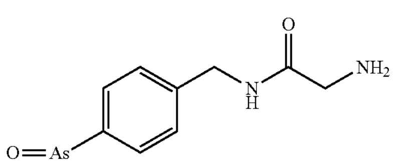 | 2-amino-N-(4-arsorylbenzyl)acetamide | 254.0 | + |
| 69 | 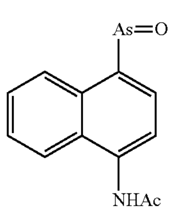 | N-(4-arsorylnaphthalen-1-yl)acetamide | 275.0 | + |
| 70 | 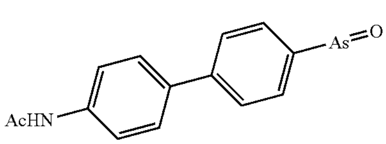 | N-(4'-arsoryl-[1,1'-biphenyl]-4-yl)acetamide | 301.0 | + |

TABLE 2-continued
| No. | Chemical structure | Name | Mw | Activity |
|---|---|---|---|---|
| 71 | 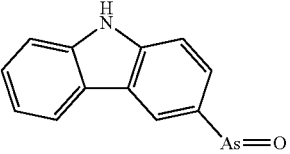 | 3-arsoryl-9H-carbazole | 257.0 | + |
| 72 | 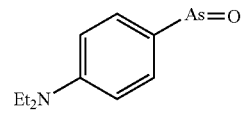 | 4-arsoryl-N,N-diethyl-aniline | 239.0 | + |
| 73 | 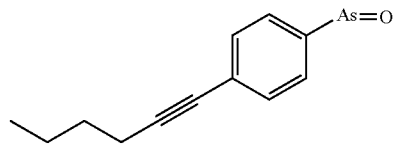 | (4-(hex-1-yn-1-yl)phenyl)(oxo)arsine | 248.0 | + |
| 74 | 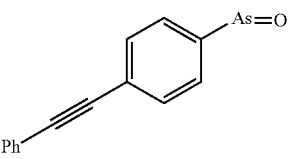 | oxo(4-(phenylethynyl)phenyl)arsine | 268.0 | + |
| 75 | 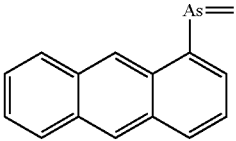 | anthracen-1-yl(oxo)arsine | 268.0 | ++ |
| 76 | 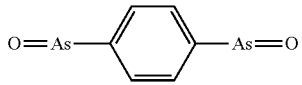 | 1,4-diarsorylbenzene | 257.9 | ++ |
| 77 | 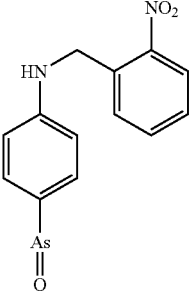 | 4-arsoryl-N-(2-nitrobenzyl)aniline | 318.16 | + |
| 78 | 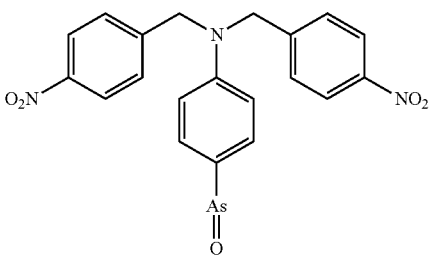 | 4-arsoryl-N,N-bis(4-nitrobenzyl)aniline | 453.3 | +++ |

TABLE 2-continued

PAO, PAO derivatives, and activities thereof

| No. | Chemical structure | Name | Mw | Activity |
|---|---|---|---|---|
| 79 | 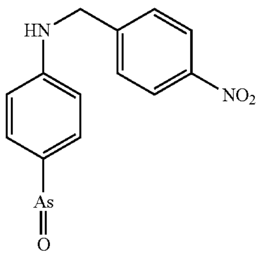 | 4-arsoryl-N-(4-nitrobenzyl)aniline | 318.16 | ++ |
| 80 | 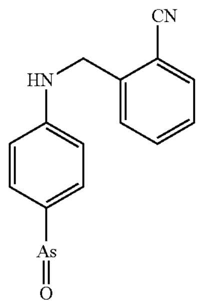 | 2-(((4-arsorylphenyl)amino)methyl)benzonitrile | 298.17 | ++ |
| 81 | 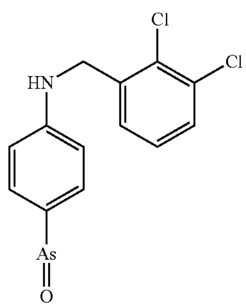 | 4-arsoryl-N-(2,3-dichlorobenzyl)aniline | 342.05 | + |
| 82 | 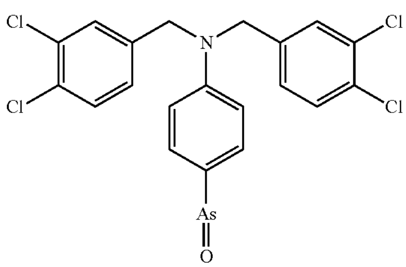 | 4-arsoryl-N,N-bis(3,4-dichlorobenzyl)aniline | 501.06 | + |
| 83 | 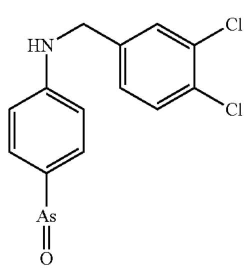 | 4-arsoryl-N-(3,4-dichlorobenzyl)aniline | 342.05 | + |

In addition, PAO facilitates Aβ$_{42}$ secretion in HEK293T cells stably transfected with human-derived APP without affecting the activities of α, β, and γ secretase which cleaves APP (FIG. 14 panel a) or causing an increase of APP level (FIG. 4 panel b).

Figure 17:
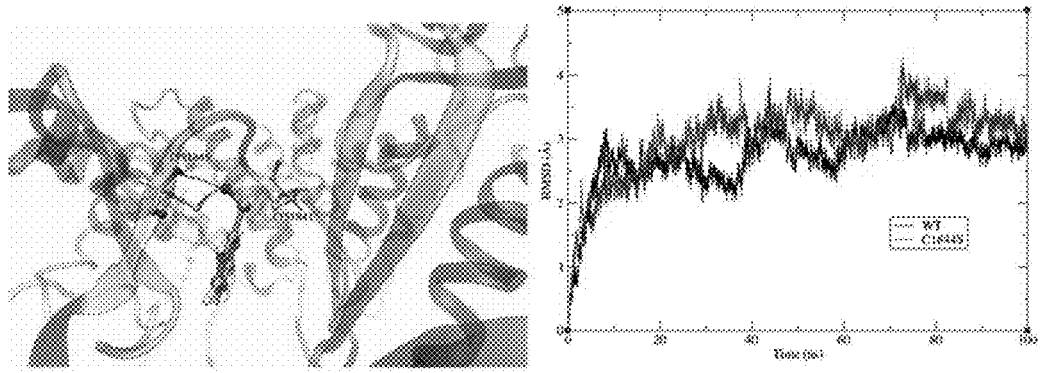
FIG. 17. Structural simulation of the binding of enzyme active center of human PI4KIIIα with PAO.

Binding simulations of PAO and derivatives thereof with PI4KIIIα: At present, structure of PI4KIIIα is yet to be measured and reported. The inventors adopt two commonly used software, SWISS-MODEL and MODELLER, with reference to the reported 4D0L structure of PI4KIIIβ, 4YKN structure of PI3Kα and 1e8x structure of PI3Kγ as templates to construct 6 structural models of PI4KIIIα. It is found that the structures of 6 models are highly consistent with each other; root mean square deviation between the structures is less than 3 Å. Interaction parameters between PAO and PI4KIIIα was simulated and calculated with this model. PAO can bind to enzyme active center of PI4KIIIα from human and other mammals, while forming two strong hydrogen bonds (bond length ~2.03 Å) with the characteristic 1840th or 1844th cysteine of enzyme active center of PI4KIIIα (FIG. 17, left), rather than forming covalent bonds with adjacent cysteines after dehydration as hypothesized in literature. In addition, dynamic simulation of binding of PAO with wild type PI4KIIIα or PI4KIIIα having mutation at the 1844th cysteine is also conducted. It is found that binding of PAO with wild type PI4KIIIα tends to stabilize after 80 nanoseconds (FIG. 17, right).

It is obvious from the simulation that PAO forms two hydrogen bonds with the backbone N atom and the side chain S atom of CYS1844, wherein the hydrogen bond to N is also strong with a O—H distance of 2.03 Å. In the dynamic simulation graph of the binding of PAO to wild type PI4KIIIα (black) and PI4KIIIα having mutation at the $1844^{th}$ cysteine (red), the root mean square deviations of the protein scaffold with respect to the original structure of the two simulation trajectories tend to stabilize after 80 nanoseconds, wherein the structural change is greater in C1844S.

Example 11: Virus Generation and Microinjection in Mice

Lentivirus was produced by invitrogen (Shanghai) using the BLOCK-iT™ HiPerform™ Lentiviral Pol II miR RNAi Expression System with EmGFP. Four miRNAs oligos targeting Efr3a were synthesized and inserted into pcDNA™6.2-GW/EmGFPmi vector. Knockdown efficiency was tested by RT-PCR or Western Blot method. Results showed that one of the vectors was most effective in knocking down Efr3a expression in HEK293T cells over-expressing EFR3a gene. Sequence of vector having the highest knockdown efficiency is AGGTATCAT-TCAGGTTCTGTT. The most effective miRNA vector was recombinated with pDONRTM221 and pLenti6/V5 DEST to generate the pLENT6/V5-GW/±EmGFP-miRNA vector via Gateway® recombination reactions. Lentivirus was generated by co-transfection of the pLENT6/V5-GW/±EmGFP-miRNA vector and Packaging Mix. Viral titer was obtained by serial dilutions in HEK293T cells. EGFP-positive cells were counted every 3 days. Knockdown efficiency was further obtained in lentivirus-transfected primary hippocampal neurons.

Male transgenic APP/PS1 mice (B6C3-Tg(APPswe, PSEN1dE9)85Dbo/Mmjax (MMRRC ID 034832-JAX) was maintained by crossing to C57BL mice. At 6 month-age, mice were anesthetized with 100 mg/kg Ketamine plus 20 mg/kg Xylazine and mounted ventral side down on stereotaxic apparatus with an electric blanket placed under its abdomen. Hair on the head was removed, skin was cut open, and a small hole was made through the skull. 2 μL lentivirus solution (viral titer: 6×10$^7$) was injected with a syringe pump (Harvard Apparatus) within 20 min through a cannula system (external diameter, 0.29 mm, internal diameter, 0.1 mm, RWD Life Science Co., Ltd) at 2.1 mm posterior to bregma, 2.3 mm lateral and 1.9 mm ventral. 5 min after injection, the needle was removed, skin was sutured, and the mouse was moved to 25° C. environment with supply of food and water. At 12 month-age, the mice were anesthetized again, and subjected to transcardiac perfusion using 4% para-formaldehyde (PFA) in PBS. Experiments complied with the policy of the Society for Neuroscience (USA) on the use of animals.

Example 12: EFR3a Knockdown May Repair Atrophy of Neuronal Dendrites in APP/PS1 Mice, Tested by GFP Staining in Mouse Brain Slices GFP staining in mouse brain slices: Brain slices (60 μm thickness) were blocked with PBS-0.3% triton-5% BSA for 1 hr., followed by incubation with rabbit anti-GFP antibody (A11122, invitrogen, 1:100 dilution) overnight at 4° C. Then wash with PBS, incubate with biotinylated goat anti-rabbit IgG antibody (H+L) (AbboMax, Inc, 1:100 dilution) overnight at 4° C. PBS wash again, incubate with Cy3-Streptavidin (Jackson ImmunoResearch Laboratories Inc, 1:1000 dilution) for 2 hrs at RT. Images were taken under Zeiss LSM 511 confocal microscope, deconvoluted with Auto-Quant X2, and analyzed with NeuronStudio software. The genotypes of brain slices and images of dendrites were blind to the imaging and analyzing personnel, respectively.

Figure 11:
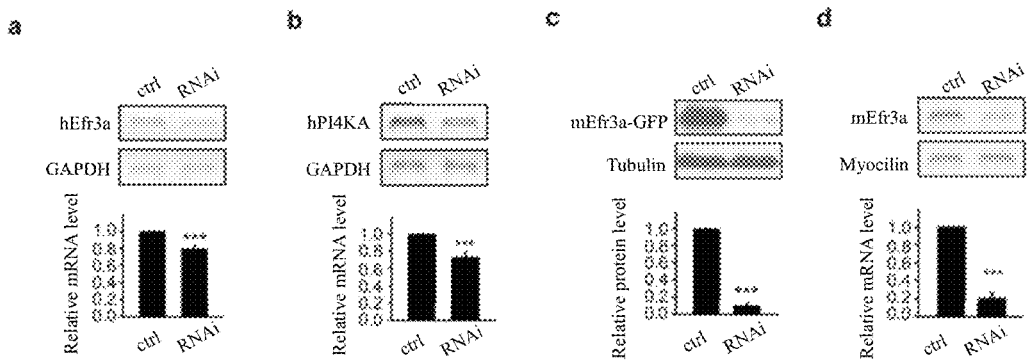
FIG. 11. Efficiency of Efr3a or PI4KA gene knockdown in HEK293 cells or primary hippocampal neurons of mice.

In FIG. 11, RT-PCR was adopted to analyze the knock-down efficiency of internal EFR3a (a) and PI4KA gene (b) in HEK293 cells, over-expressing mouse EFR3a-gfp recombinant gene (c) in HEK293 cells, and internal Efr3a gene (d) in primary hippocampal neurons of mice. Representative images are on top and normalized quantification are on bottom. The sequences used for constructing Efr3a and PI4KA gene knockdown RNAi are 5'-GGTTATTGAAAT-TCGAACT-3' (SEQ ID NO: 5) and 5'-TGCTCATT-AGCAGTAAAGA-3' (SEQ ID NO: 6), respectively. n=3-5 for each data, t-tested to obtain P value.

Figure 5:
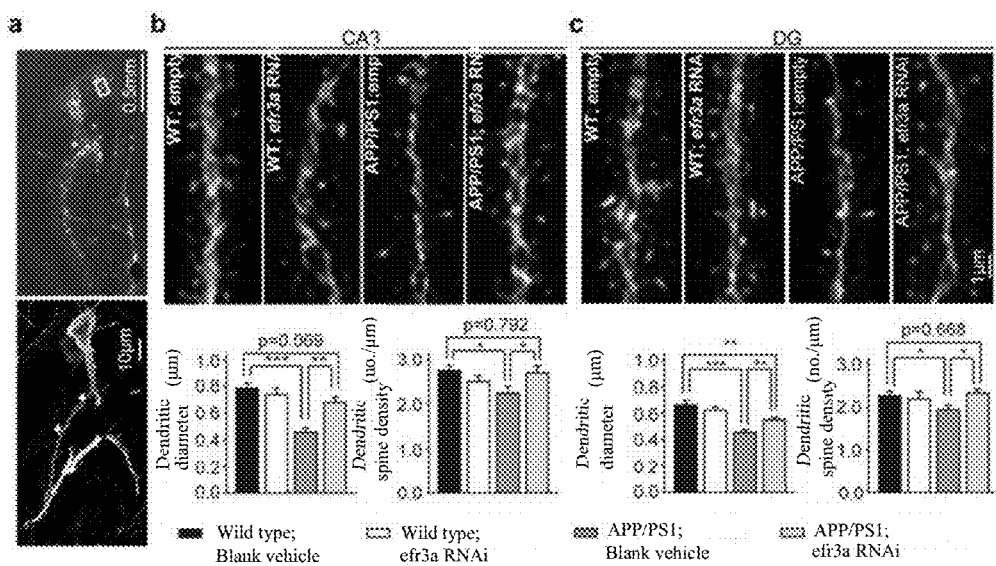
FIG. 5. Effects of Efr3a gene knockdown on dendritic diameter and spine density of neurons in hippocampal CA3 and DG segments in APP/PS1 mice and control mice.

In FIG. 5 panel a, confocal images show anti-GFP immunostained whole hippocampus slices (top) and lentivirus-transfected pyramidal cells in CA3 segments (bottom). Dendrite fragment of about 30 μm was selected for quantification of dendritic diameter and spine density. The scale bars represent 500 μm (top) and 50 μm (bottom), respectively. In CA3 segment pyramidal neurons (FIG. 5 panel b) and CA3 segment granule neurons (FIG. 5 panel c) of APP/PS1 mice and control littermates, EFR3a gene knockdown affects dendritic diameter and spine density. Representative images of CA3 and DG segment dendrites are on top and quantification of dendritic diameter and spine density are on bottom. Each data point was obtained from n≥25 slices of 3~4 animals, P values were obtained by one-way ANOVA analysis. In FIG. 5 panels b-c, the scale bar represents 1.0 μm.

Mice and human possess two rbo homologs, EFR3a and EFR3b, both of which are enriched in the hippocampus and the like regions (Allen Brain Atlas) which are highly susceptible to AD. We investigated whether down-regulation of EFR3a gene can protect hippocampal neurons in APP/PS1 mice by using EGFP-tagged RNAi method. RNAi knockdown efficiency was shown in FIG. 11 panels a-b. Confocal imaging revealed that the EGFP-expressing lentivirus infected a small number of neurons in CA3 and DG segment (FIG. 11 panel a). Dendritic diameter and spine density were measured on randomly selected proximal segments (~30 μm in length) of the second-order apical dendrites. The values of the two parameters of both CA3 and DG segment neurons of APP/PS1 mice infected with control lentivirus were significantly decreased than those in wild-type control mice and APP/PS1 mice (FIG. 5 panels b-c), which indicates atrophy of dendrites and spines of hippocampal neurons in APP/PS1 mice. Comparing between APP/PS1 mice, the values of the two parameters were significantly increased in neurons infected with RNAi lentivirus, there are no significant difference to the values in wild-type mice (Fig. panels b-c). Therefore, down-regulation of the rbo homolog EFR3a in hippocampal neurons in APP/PS1 mice also protects the neurons.

Example 13: PAO Improves Learning and Memory, Increases $A\beta_{42}$ in CSF, but Decreases $A\beta_{42}$ in Brain Membrane in APP/PS1 Mice, Detected by Composition Analysis of CSF and Membrane of Fractionated Mouse Brain Cerebrospinal fluid collection: Mice were anesthetized with Ketamine and Xylazine, and were secured with head adaptors. The skin of the neck was shaved and cut open, the underlying subcutaneous tissue and muscles were separated laterally with forceps to expose the dura above the cisterna magna. A sharp-tipped glass capillary with a blunt end connected to a microinjection syringe was used to penetrate the dura. Following a noticeable change in resistance to the capillary tube insertion, the capillary entered the cisterna magna, CSF flowed into the capillary tube, until approximately 10-20 μL was collected. The collected CSF was transferred into an Eppendorf tube containing protease inhibitor, and stored at −80 OC until use.

Fractionation of mouse brain membrane: Obtain detergent-soluble $A\beta_{42}$ through serial extraction. 5 times in volume of mouse brain hemisphere of Tris-buffered saline (TBS) was added for grounding and homogenizing, centrifuged at 100,000 g for 60 min and the supernatant was the TBS extract. The precipitate was collected, added 5 times in volume TBS containing 1% polyethylene glycol octylphenol ether for grounding, centrifuged and the supernatant was the TBS-Triton extract. The precipitate was collected again, added 5 times in volume TBS containing 1% SDS for grounding, centrifuged and the supernatant was the TBS-SDS extract. All three supernatants were collected, aliquoted and stored in −80° C. refrigerator for ELISA assay.

The foregoing results in cultured cells and flies demonstrate that PAO facilitates $A\beta_{42}$ secretion, reduces intraneuronal $A\beta_{42}$ accumulation, and ameliorates synaptic failure, indicating that PAO is a potential drug for treating AD by facilitating $A\beta_{42}$ secretion. To test this, we performed behavioral and biochemical experiments with APP/PS1 mice gavaged with PAO at different doses.

Figure 6:
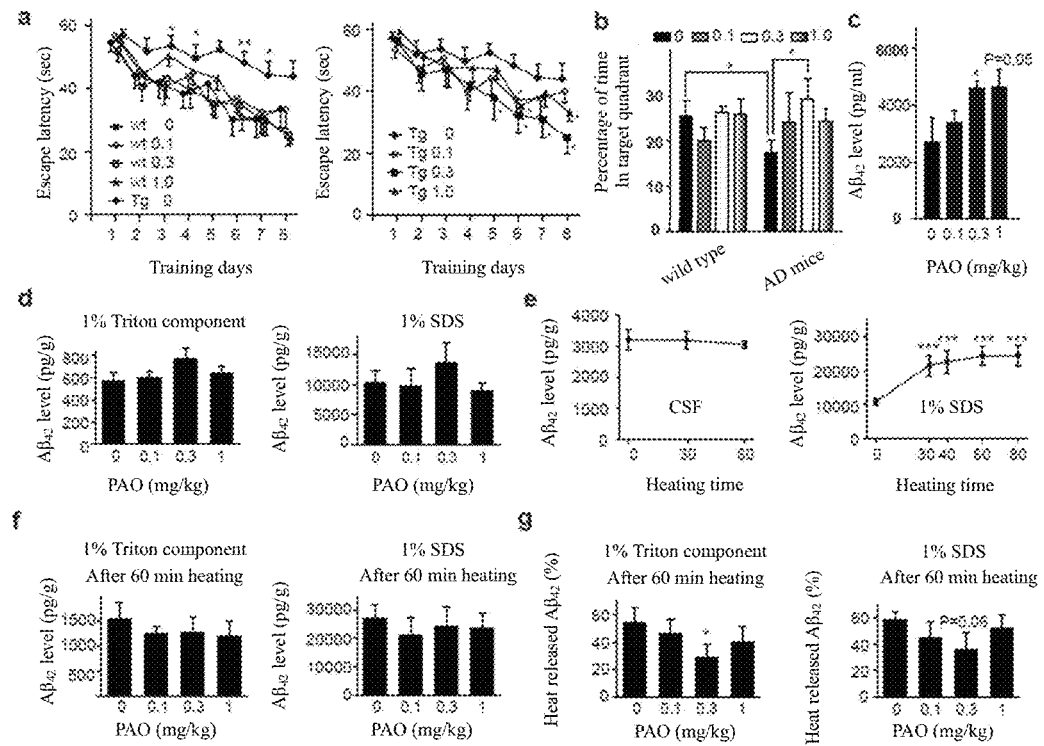
FIG. 6. Effects of PAO treatment on learning and memory, CSF- and brain membrane-associated A$\beta_{42}$ level in APP/PS1 mice and control mice.

FIG. 6 panel a shows the Morris Water Maze training curves of APP/PS1 mice treated with PAO at different doses (left) and wild-type littermates (right). For comparison purposes, learning curve of APP/PS1 mice gavaged with 0 PAO was shown in both the left and right graphs. FIG. 6 panel b shows percentage of searching time spent in the target quadrant to total searching time of control and APP/PS1 mice after training. ELISA quantification was used to analyze $A\beta_{42}$ level in CSF of APP/PS1 mice treated with different PAO concentrations (FIG. 6 panel c), and in fractionated brain membrane extracted with TBS containing 1% Triton and 1% SDS (FIG. 6 panel d). FIG. 6 panel e shows effect of heat treatment time at 100° C. on measured $A\beta_{42}$ value in ELISA quantification of CSF of APP/PS1 mice (left) and fractionated brain membrane extracted with TBS containing 1% SDS (right). FIG. 6 panel f shows $A\beta_{42}$ level in ELISA quantification of fractionated brain membrane extracted with TBS containing 1% Triton and 1% SDS after heat treatment at 100° C. for 60 min. FIG. 6 panel g shows percentage of $A\beta_{42}$ released after heat treatment at 100° C. for 60 min in fractionated brain membrane extracted with TBS containing 1% Triton and 1% SDS to total $A\beta_{42}$. In FIG. 6 panels a-b, n=6-8 for wild-type control, n=7-8 for each APP/PS1 group. In FIG. 6 panel e, n=3 for left graph and n=23 for right graph. In FIG. 6 panels c, d, and f, n=5-6. All P values were obtained by one-way ANOVA analysis.

Having examined the toxicity of PAO gavage in wild-type mice as described in Example 8, the following experiments were performed with a concentration gradient of 0, 0.1, 0.3 and 1.0 mg/kg. 4 month-age APP/PS1 mice and wild-type mice were subjected to PAO gavage, once a day every Monday through Friday for 6 consecutive weeks. Then, PAO administration was stopped for one week, and learning and memory abilities of mice were tested by the water maze experiment according to Vorhees and Williams. Compared to wild-type control, APP/PS1 mice without PAO treatment exhibited impaired spatial learning and memory abilities (FIG. 6 panels a-b). This impairment was significantly reduced in PAO-treated APP/PS1 mice, most notably at the dosage of 0.3 mg/kg (FIG. 6 panels a-b). This result indicates that PAO can be used to treat learning and memory dysfunction in APP/PS1 mice. After the behavior test, CSF were collected and brain membrane fractionation were extracted from each APP/PS1 mouse. The brains were subjected to fractionation for extracting membrane-associated $A\beta_{42}$ with two TBS buffers containing 1% Triton X-100 or 1% SDS for ELISA quantification assay. It was found that PAO increased $A\beta_{42}$ level contained in CSF (FIG. 6 panel c), and also unexpectedly increased the $A\beta_{42}$ level in brain membrane, most notably at the dosage of 0.3 mg/kg (FIG. 6 panel d). However, FIG. 6 panel f shows that PAO treatment reduced aggregated $A\beta_{42}$ level in brain membrane, most notably at the dosage of 0.3 mg/kg.

Example 14: PAO Gavage Ameliorates Cognitive Impairment of APP/PS1 Mice at Older Month-Age In order to study the treatment effect of PAO on APP/PS1 mice already having identifiable learning and memory dysfunction, 8 month-age APP/PS1 mice and wild type littermates were subjected to PAO gavage at doses of 0 or 0.3 mg/kg body weight, once a day every Monday through Friday for 6 consecutive weeks. Then, administration was stopped for one week, and mice were subjected to novel object recognition test (NOR). The results showed that PAO treated mice spend significantly more time exploring novel object than old object that was explored the day before. In order to study effect of PAO on older month-age APP/PS1 mice, as well as toxicity of prolonged administration on mice, 20 APP/PS1 mice at 18 month-age was randomly divided into two groups with 10 mice in each group. One group was subjected to PAO gavage at doses of 0.3 mg/kg body weight, once a day every Monday through Friday, the other group was subjected to water gavage; no administration at weekends. After 8 consecutive months, administration was stopped for one week, and mice were subjected to NOR test. During 8 months of gavage, two mice were dead in each group. NOR test showed that mice in PAO treatment group spend significantly more time exploring novel object than mice in the other group (FIG. 18).

Figure 18:
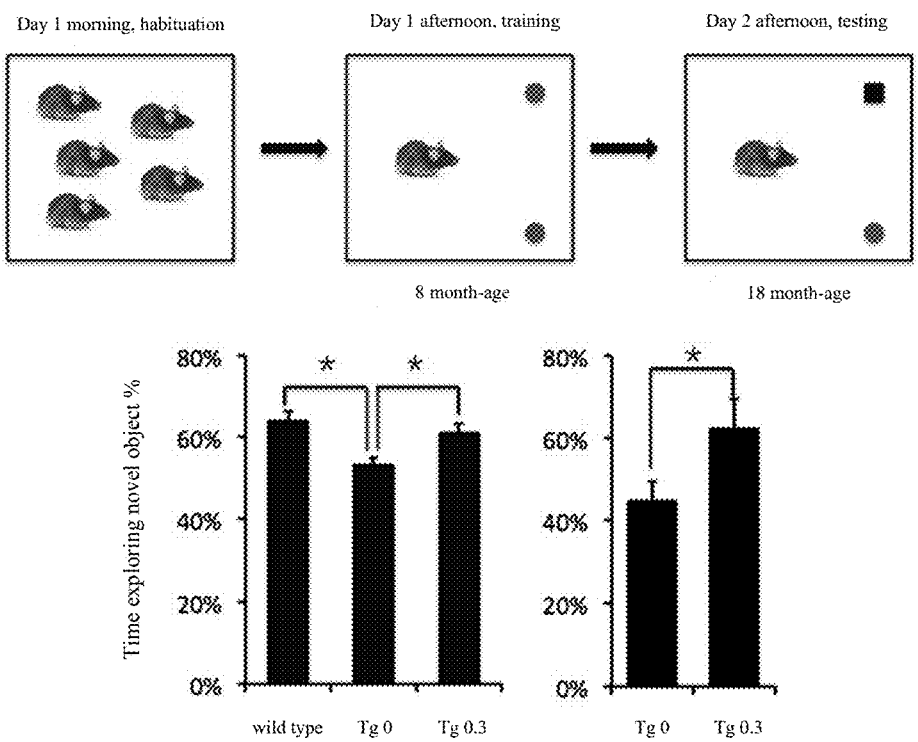
FIG. 18. Treatment effect of PAO on cognitive defect in APP/PS1 mice at older month-age.

NOR test designing and FIG. 18: In the first morning, mice were placed into a 20×20×32 cm transparent acrylic glass box from the rear door, then took out after habituation for 30 min; do not clean the box. In the afternoon of the same day, a camera was placed in front of the box and two identical objects were placed in the two corners of the box facing the camera. A single mouse was placed into the box; after 7 min, the mouse and two objects were taken out.

Again, the box was not cleaned; another two identical objects were placed and then the second mouse. Repeat in this manner until all mice finished training. In the afternoon of the second day, test was conducted using the same box. Two objects were placed into the box, wherein one objected was explored by the mouse in the first day and the other object was new to the mouse. The whole process from the mouse entering the box till test was finished after 7 min was video-taped. During the whole test procedure, the box was not cleaned. In offline analysis, playback video in a computer and time spent by the mouse on exploring novel and old objects were separately counted by a person not involved in the NOR test.

In FIG. 18, the top row is a schematic diagram of the designing of the mouse NOR test. The bottom row is the percentage of time spent on exploring novel object compared to the total time exploring both novel and old objects by the mouse in the NOR test. Each group of data in the left graph is the Mean and SEM of 9 mice. Each group of data in the right graph is the Mean and SEM of 8 mice. T-test, single-tailed.

Figure 12:
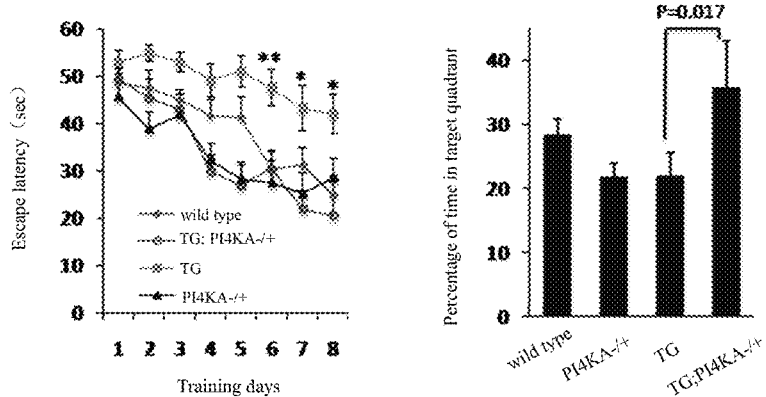
FIG. 12. Transposon insertion into one copy of PI4KA gene of APP/PS1 mice significantly ameliorates learning and memory defect.

Example 15: PI4KIIIα Mutation Ameliorates Learning and Memory Defect in APP/PS1 Mice, Tested by Water Maze Experiment Genetic down-regulation of PI4KIIIα expression level or inhibition of its enzyme activity with PAO in Aβ$_{42}$-expressing flies both ameliorates neural dysfunction; inhibition of PI4KIIIα enzyme activity with PAO in APP/PS1 mice also improves learning and memory abilities. In order to further clarify the role of PI4KIIIα ion the neurodegeneration in APP/PS1 mice, the effect of heterozygous mutation of PI4KIIIα (Pi4ka$^{Gt(RRO073)Byg/+}$: insertion of transposon pGT2Lxf into one copy of PI4KA gene may impede transcription of the gene copy, the resulted mRNA may only translate the truncated protein formed by the first ~265 amino acids on the N-terminus of PI4KIIIα and the protein encoded by the reporter gene) on water maze experiment in APP/PS1 mice was examined. Pi4ka$^{Gt(RRO073)Byg/+}$ mutation heterozygotes (MMRRC, Cat. #016351-UCD) were crossed with APP/PS1 mice to obtain four groups of genotype mice: wild-type (WT), PI4KIIIα mutation heterozygote (PI4K$^{*/+}$), APP/PS1 (TG) and APP/PS1 with PI4KIIIα heterozygous mutation (TG;PI4K$^{*/+}$). When mice in the four groups reached 5 month-age, water maze experiments were performed according to Vorhees and Williams. As shown in FIG. 12, PI4KIIIα heterozygous mutation can significantly ameliorate the spatial learning and memory defect of 5 month-age APP/PS1 mice. Left of FIG. 12 shows the learning curves of four groups of genotype mice, right of FIG. 12 shows percentage of swimming time in the target quadrant to total time on the first day after training day of four groups of genotype mice.

Example 16: Down-Regulation of PI4KIIIα Expression Level and Inhibition of PI4KIIIα Enzyme Activity by PAO Both Significantly Ameliorate Synaptic Transmission Plasticity Impairment in the Hippocampus of APP/PS1 Mice In order to detect the effect of down-regulation of PI4KIIIα expression level and inhibition of PI4KIIIα enzyme activity by PAO on the synaptic transmission plasticity impairment in hippocampus of mouse, we induced and recorded long-term potentiation (LTP) of hippocampus CA3-CA1 synapses in mouse brain slices. 4 month-age APP/PS1 mice and wild type littermates were subjected to PAO gavage at doses of 0 or 0.3 mg/kg body weight, once a day every Monday through Friday for 4 consecutive weeks. Then, administration was stopped for one week. We found that the LTP amplitude of APP/PS1 mice without PAO treatment was significantly lower than the LTP amplitude of wild type mice and APP/PS1 mice treated with PAO (FIG. 19 panel a), which indicated that PAO treatment significantly ameliorated synaptic transmission plasticity impairment in the hippocampus of APP/PS1 mouse. Consistently, PI4KA gene with one less copy also significantly ameliorated synaptic transmission plasticity impairment in the hippocampus of APP/PS1 mouse (FIG. 19 panel b), while PI4KA with one less copy did not affect LTP itself (FIG. 19 panel c).

Method: Preparation of mouse hippocampal slices and recording of LTP of hippocampus CA3-CA1: Take a mouse of about 6 month-age, 30 g body weight, clean grade. Anesthetize the mouse by intraperitoneal injection of 1% pentobarbital sodium. Anesthetized to coma and surgery by thoracotomy to expose the entire heart; cut to open the right auricle; inject 30 mL of 4° C. PBS rapidly with a 50 mL syringe and a #3 needle through the left ventricle; decapitate; fix the head and cut with scissors along the skull midline and along both sides of the cranial base to open the skull, while continually washing the brain with ~0° C. anatomy fluid (the anatomy fluid is pre-filled with a mixed gas comprising 95% $O_2$+5% $CO_2$ for 30 min); then place the entire brain on a plate containing ~0° C. anatomy fluid; remove olfactory bulb and cerebellum with surgery knife and curved tweezers; separate the two cerebral hemispheres along the cranial line; after trimming brain block, add a small amount of ethyl α-cyanoacrylate glue to the base to ensure stably standing of the hippocampus tissue; rapidly place the base in the slicer tank containing ~0° C. anatomy fluid while continually filling of the mixed gas; cut sagittally to obtain brain slice with a thickness of 400 m; place the brain slice in a glass cup containing artificial cerebrospinal fluid (ACSF, pre-filled with a mixed gas for 30 min); incubate at room temperature (~25° C.) for 1-2 h before use. (ACSF in mM: 124 NaCl, 2 KCl, 2 $MgSO_4$, 1.25 $KH_2PO_4$, 2 $CaCl_2$, 26 $NaHCO_3$, 10 D-glucose [pH 7.4], 300 mOsm).

Record field excitatory postsynaptic potentials (fEPSPs) at hippocampus CA1 region according to standard procedure: place two stimulating probes (FHC Inc., Bowdoin, Me.) at the Schaffer collaterals of hippocampus CA3 region, place one glass microelectrode and one recording electrode at the stratum radiatum of the CA1 region. Distance between the stimulating probe and the recording probe is about 200~300 μm. Stimulating intensity is 30-50% of the stimulating intensity to induce maximum amplitude of fEPSPs; stimulating frequency is 0.05 Hz. After the amplitude of induced fEPSPs was stabilized for 20 min, high frequency stimulation at 100 Hz was given through the stimulating probes and was repeated after 20 sec. After stimulation, continue with 0.05 Hz stimulation and record fEPSPs for 80 min. high frequency filter at 1 kHz, recording frequency at 20 kHz, pre-amplifier is Heka EPC 10 amplifier (Harvard Bioscience Inc., Ludwigshafen, HRB).

Figure 19:
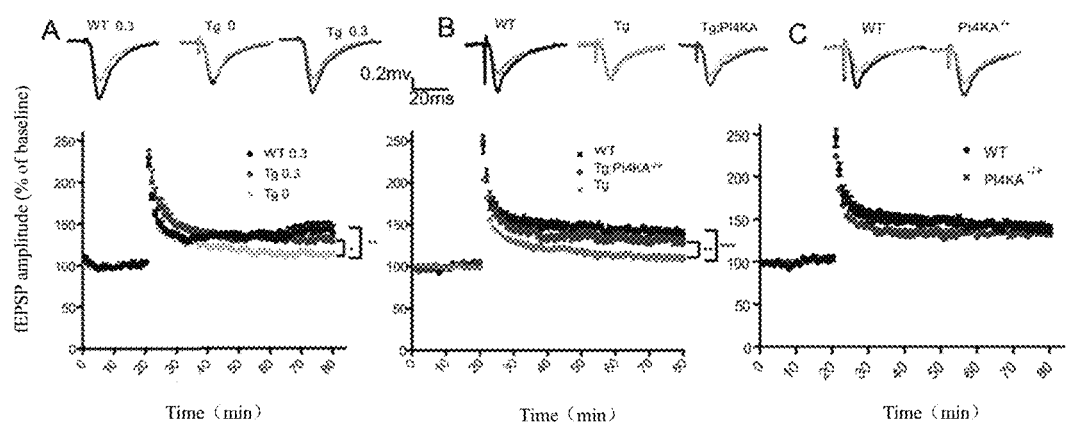
FIG. 19. Down-regulation of PI4KIIIα expression level and inhibition of PI4KIIIα enzyme activity by PAO both significantly ameliorate synaptic transmission plasticity impairment in the hippocampus of mouse.

FIG. 19 shows that down-regulation of PI4KIIIα expression level and inhibition of PI4KIIIα enzyme activity by PAO both significantly ameliorate synaptic transmission plasticity disorder impairment in the hippocampus of APP/PS1 mice. In A-C, the top row is representative fEPSP records of CA1 before (grey) and after (black) high frequency stimulation, the bottom row is quantitative analysis. Mouse brain slices were derived from three groups of littermate mice at 6 month-age: PAO treated wild type mice (WT 0.3), untreated APP/PS1 mice (Tg 0), and PAO treated APP/PS1 mice (Tg 0.3); or were derived from four groups of littermate mice: wild type (WT), PI4KA$^{-/+}$, APP/PS1 (Tg) and APP/PS1; PI4KA$^{-/+}$ (Tg;PI4KA$^{-/+}$). Each data point is derived from the Mean and SEM of 7~9 brain slices from 3~4 mice. One-way ANNOVA analysis.

Example 17: Effects of PI, PI$_4$P, PI$_{4,5}$P on Aβ$_{42}$ Aggregation/Oligomerization in Liposomes, Tested by Liposome Experiment Liposome Experiment:
1) Dissolving synthetic Aβ$_{42}$ with hexafluoro-2-propranol (HFIP) at a ratio of 1:1 (mg:mL), followed by 50 Hz sonication at RT for 15 min for homogenization. The sonicator is KUDOS ultrasonic instrument (Model SK250HP).
2) Dissolving the lipids (Table 1) with chloroform separately to prepare the lipids used for generating liposomes (Table 3) at a ratio of 1:1 (mg:mL), followed by 50 Hz sonication at RT for 15 min for homogenization.
3) Mixing the lipids according to the composition as listed Table 3, following by removing organic solvents from solution with lyophilizer.
4) Resuspending the precipitate after lyophilization with 1.0 mL Tris buffer (50 mM Tris, 120 mM NaCl, pH 7.0), followed by sonication in ice water for 30 min for homogenization. Stay at 4° C. for 48 hours for immunoblot analysis (primary antibody is anti-humanized Aβ monoclonal antibody 6E10, 1:1000 dilution). Before immunoblot analysis, 15 min of sonication is required for homogenization.

TABLE 3

Composition of liposome preparations

|  | CAS # | Mw | Mole % | Volume (1 mg/ml) |
|---|---|---|---|---|
| Phosphatidylserine (PS) | 145849-32-7 | 757.95 | 8.9 | 68 µL |
| Phosphatidylcholine (PC) | 63-89-8 | 734.04 | 15.4 | 121 µL |
| Phosphatidylethanolamine (PE) | 1069-79-0 | 748.07 | 26.5 | 196 µL |
| Cholesterol (CH) | 57-88-5 | 386.65 | 14.8 | 57 µL |
| Sphingomyelin (SM1) | 85187-10-6 | 973.55 | 8.9 | 86 µL |
|  |  |  | Final conc. |  |
| Aβ$_{42}$ |  | 4514.04 | 1.0 µM | 4.5 µL |
| PI (diC16) | 119943-95-2 | 833.01 | 20 µM | 17 µL |
| PI$_4$P (diC16) | 214332-61-3 | 956.96 | 20 µM | 19 µL |
| PI$_{4,5}$P (diC16) | 120595-88-2 | 1080.9 | 20 µM | 22 µL |

Figure 13:
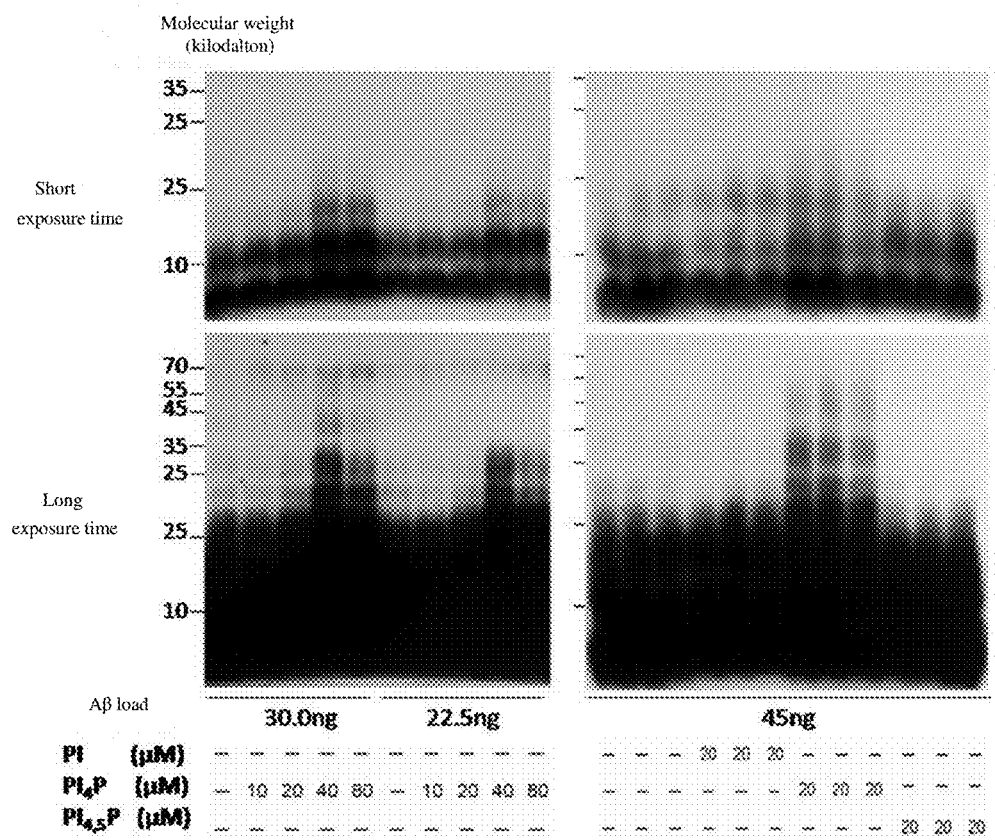
FIG. 13. PI4P facilitates the oligomerization of A$\beta_{42}$ in liposomes.

Effects of PI, PI$_4$P, PIP$_2$ on the aggregation/oligomerization of Aβ$_{42}$ in liposome were analyzed and compared. In FIG. 13, left column shows that PI$_4$P facilitates the oligomerization of Aβ$_{42}$ in liposome in a concentration dependent manner, wherein top and bottom are results of a same immumoblotting membrane under short and long light exposure, respectively; it is noted that at PI$_4$P concentration of 80 jµM, the facilitation effect on oligomerization of Aβ$_{42}$ decreases as compared to a concentration of 40 jµM. Right column of FIG. 13 shows facilitation effects of PI, PI$_4$P, and PIP$_2$ on Aβ$_{42}$ aggregation in liposomes, wherein top and bottom are results of a same immumoblotting membrane under short and long light exposure, respectively; it is noted that at the effect of PI$_4$P is significantly stronger than PI and PIP$_2$, while the facilitation effect of PI$_4$P on the oligomerization of Aβ$_{42}$ trimer and above is stronger than those of PI and PIP$_2$.

Example 18: Complex Formation of RBO/EFR3/EFR3A/EFR3B, PI4KIIIα, and TTC7 on Cell Membrane It is reported that yeast EFR3 protein forms a complex with PI4KIIIα and a scaffold protein YYP1 (referred to as TC7 in mammals, including two homologs TTC7A and TTC7B) on cell membrane and aggregates as PIK patches, and together regulate plasmalemma PI$_4$P level and even PI$_{4,5}$P level. YYP1 interacts directly with N-terminus and central region of yeast PI4KIIIα protein, thus playing an important role in construction and stabilization of PIK patches (Baird D, Stefan C, et al., 2008, J Cell Biol). Formation and function of PIK patches are also conservative in mammal cells (Nakatsu F, Baskin J F, et al., 2012, J Cell Biol). *Drosophila* homolog of TTC7 in flies is encoded by lethal (2) k14710 (l(2) k14710) gene.

To test the role of TTC7 protein in the neurodegeneration caused by intraneuronal Aβ accumulation, two transposon mediated transgenes were introduced into Aβ$_{arc}$ flies. P{lacW}l(2)k14710k$^{15603}$ transposon (Bloomington Cat. #11134) was inserted into the first exon of l(2) k14710 gene in order to prevent transcription of l(2) k14710; the other one is P{EPgy2}bin3$^{EY09582}$ (Bloomington Stock #20043). Four groups of flies were constructed in this experiment: control flies (ctrl), Aβ$_{arc}$ flies (Aβ$_{arc}$), Aβ$_{arc}$ flies having one copy of P{lacW}l(2) k14710k$^{15603}$ (Aβ$_{arc}$-dttc7$^{+/-}$, TTC7 down-regulating) and Aβ$_{arc}$ flies having one copy of P{EPgy2}bin3$^{EY9582}$ (Aβ$_{arc}$-dttc7-OE, TTC7 over-expressing). When adult flies of four groups reached age period of 5-10 day-age and 30-35 day-age, recording of EJP in GF pathway were conducted under 100 Hz brain stimulation.

Figure 15:
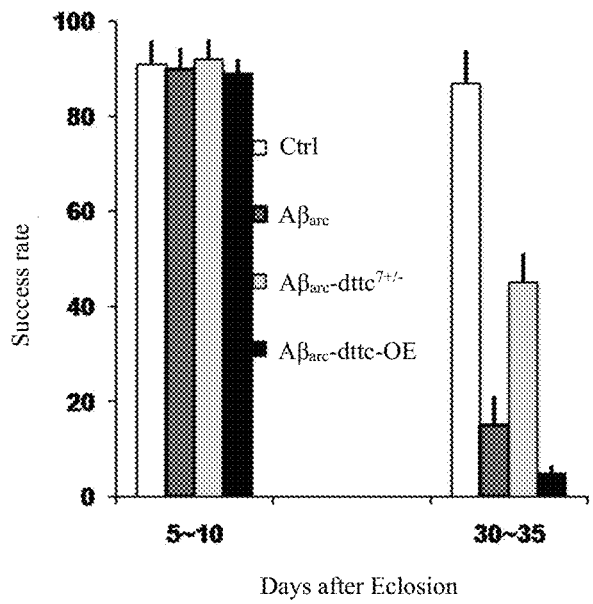
FIG. 15. Effects of ttc7 gene mutation and over-expression on neural deficits in $A\beta_{arc}$-expressing flies.

FIG. 15 shows quantification analysis of effects of ttc7 down-regulation and over-expression on neural transmission in Aβ$_{arc}$ flies. At 5-10 day-age, there are no significant differences in the success rates of 100 Hz brain stimulation-induced neural transmission; however, at 30-35 day-age, success rate of Aβ$_{arc}$ flies is significantly lower than that of contrl flies (ctrl), TTC7 over-expression (Aβ$_{arc}$-dttc7-OE) further decreases the success rate, while TTC7 down-regulation (Aβ$_{arc}$-dttc7$^{+/-}$) increases the success rate of neural transmission.

Preferred embodiments for carrying out the invention are described herein. The present invention is not limited to above embodiments. Any variation, modification, substitution, combination, and simplification without departing from the spirit and principle of the present invention belongs to equivalents of the present invention and is included within the scope of protection of the present invention.

The invention claimed is:

1. A method for treating ameliorating or inhibiting Alzheimer's disease and its symptoms in a subject in need thereof, the method comprising administering to the subject a PI4KIIIα inhibitor.

2. The method of claim 1, wherein said PI4KIIIα inhibitor is an antibody against PI4KIIIα, an inhibitory nucleotide specific to PI4KIIIα, or a small molecule compound inhibitor specific to PI4KIIIα.

3. The method of claim 2, wherein said inhibitory nucleotide specific to PI4KIIIα has the nucleotide sequence as shown in SEQ ID NO: 6.

4. The method of claim 2, wherein said PI4KIIIα inhibitor is a small molecule compound inhibitor selected from the group consisting of PAO, a PAO derivative, G1, A1, analogues of G1, and analogues of A1.

5. The method of claim 4, wherein said PAO derivative is a small molecule compound inhibitor selected from the group consisting of:

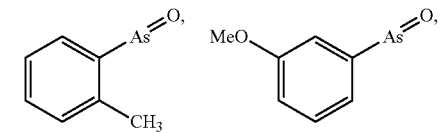

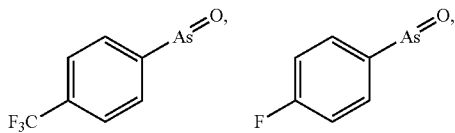

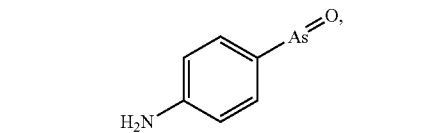

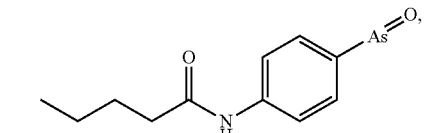

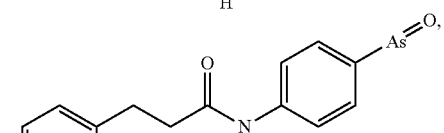

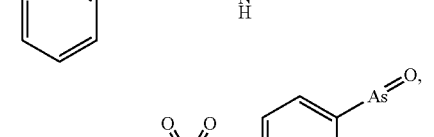

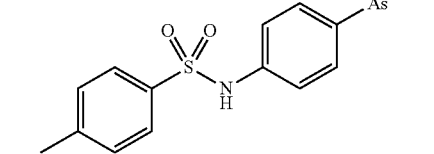

-continued

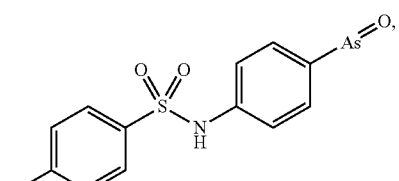

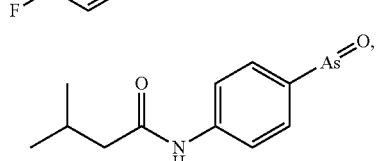

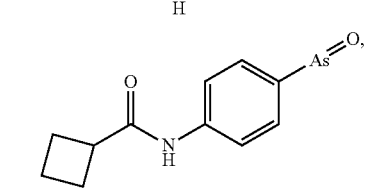

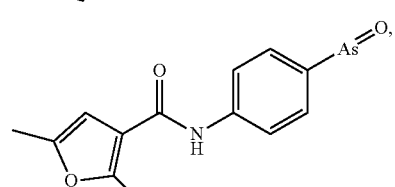

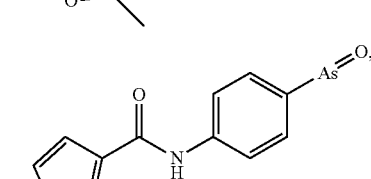

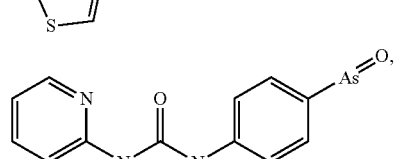

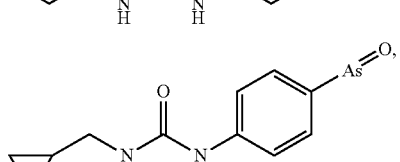

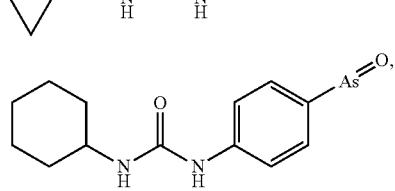

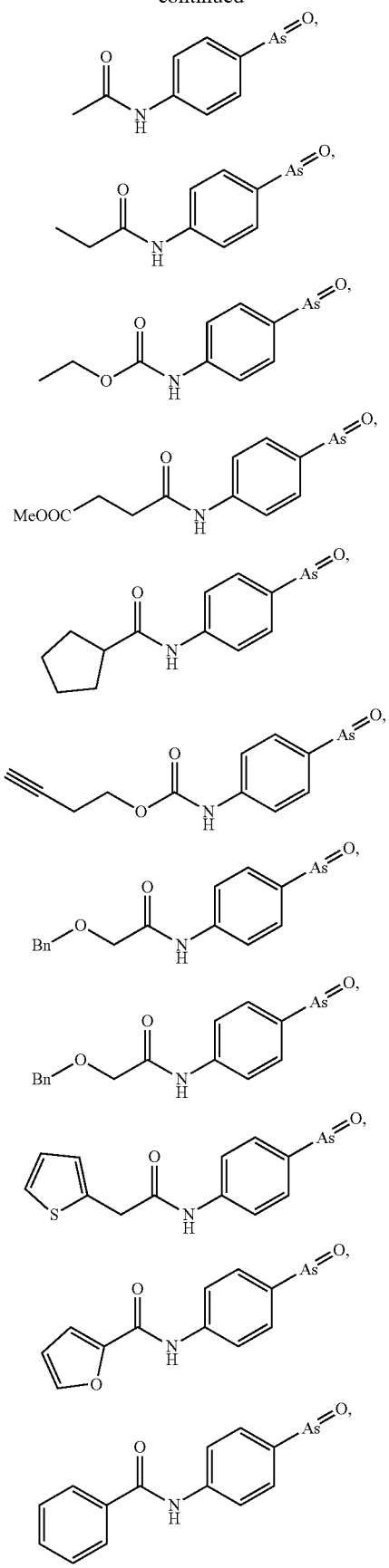
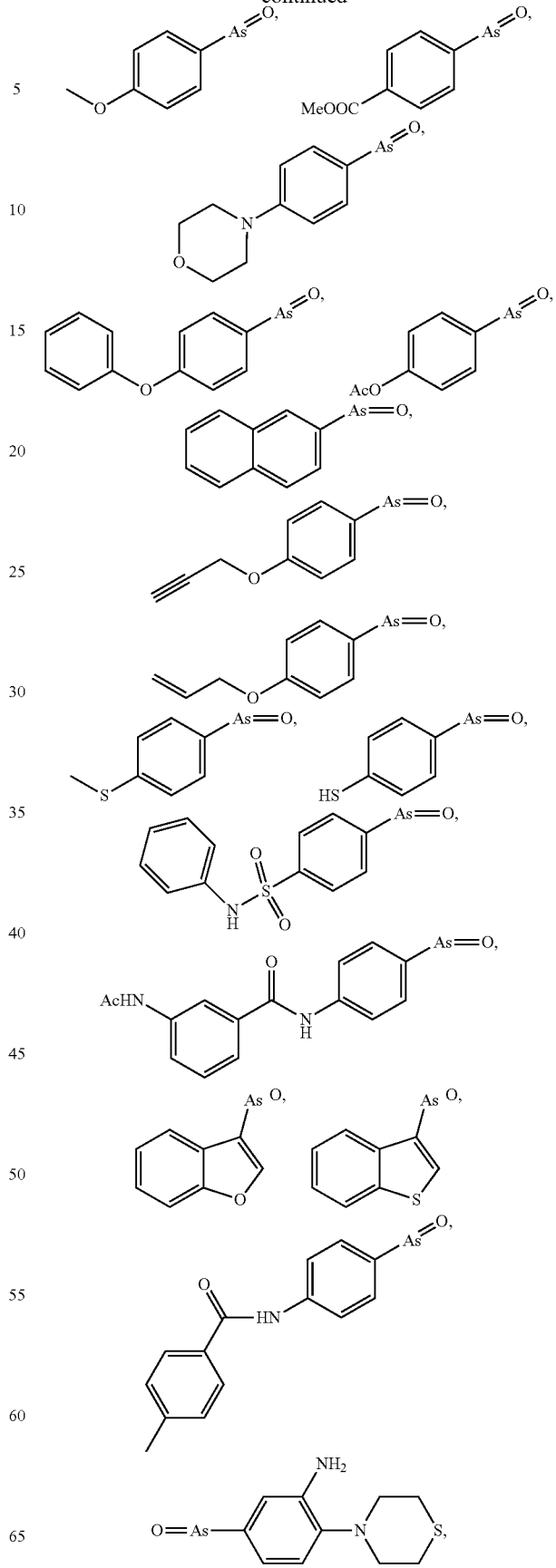

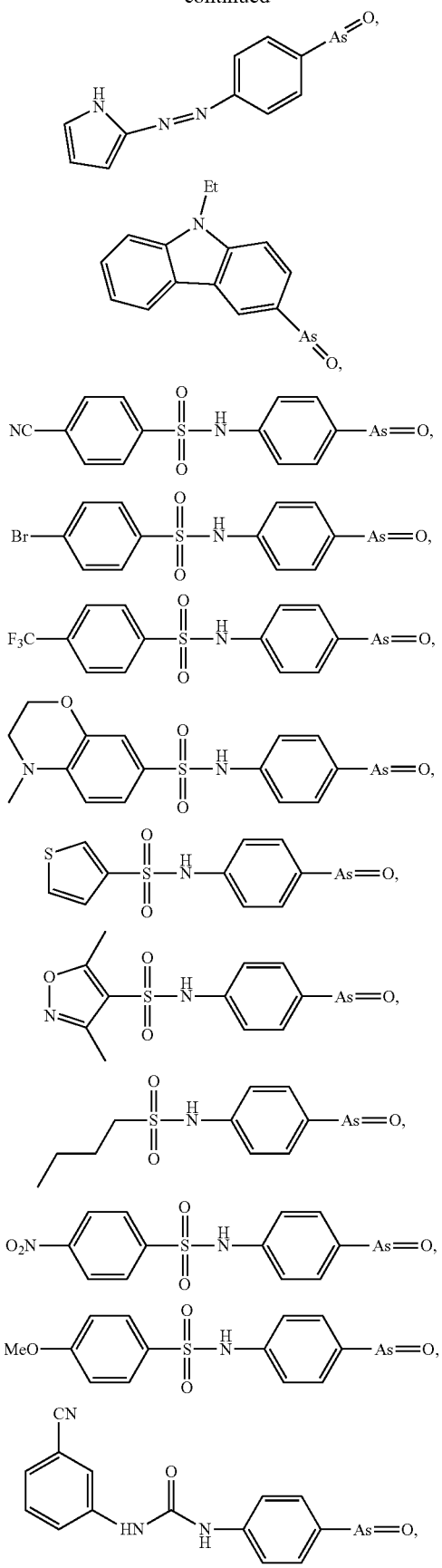
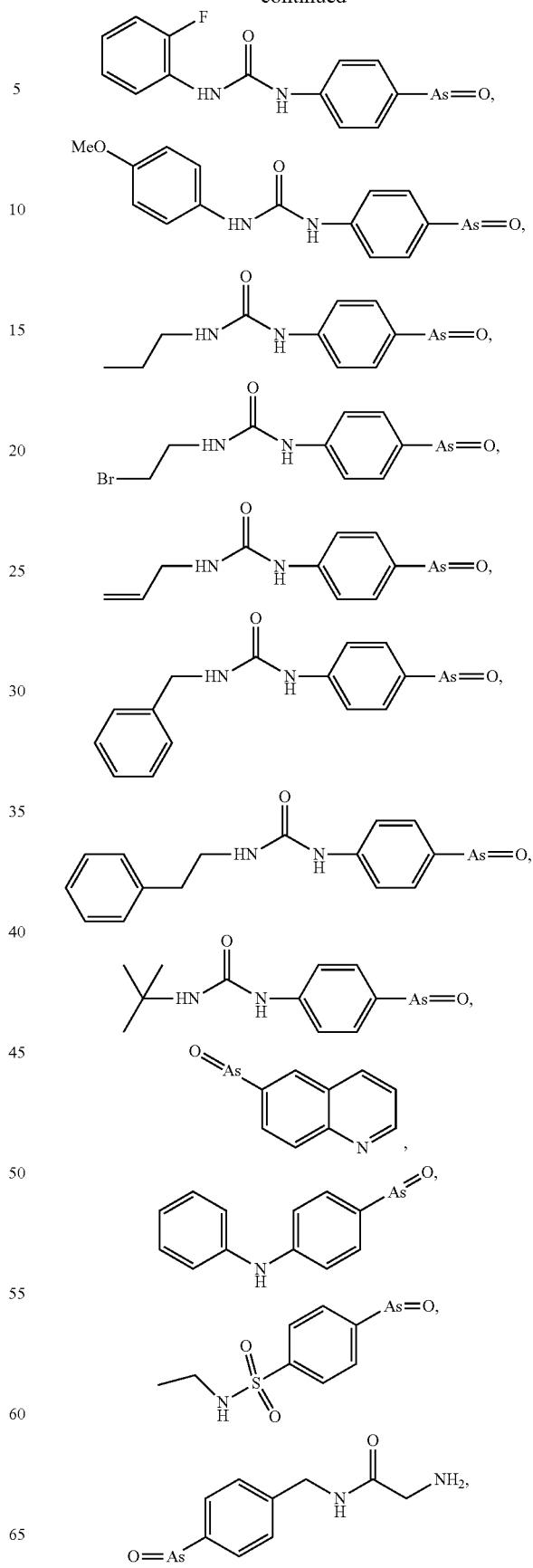

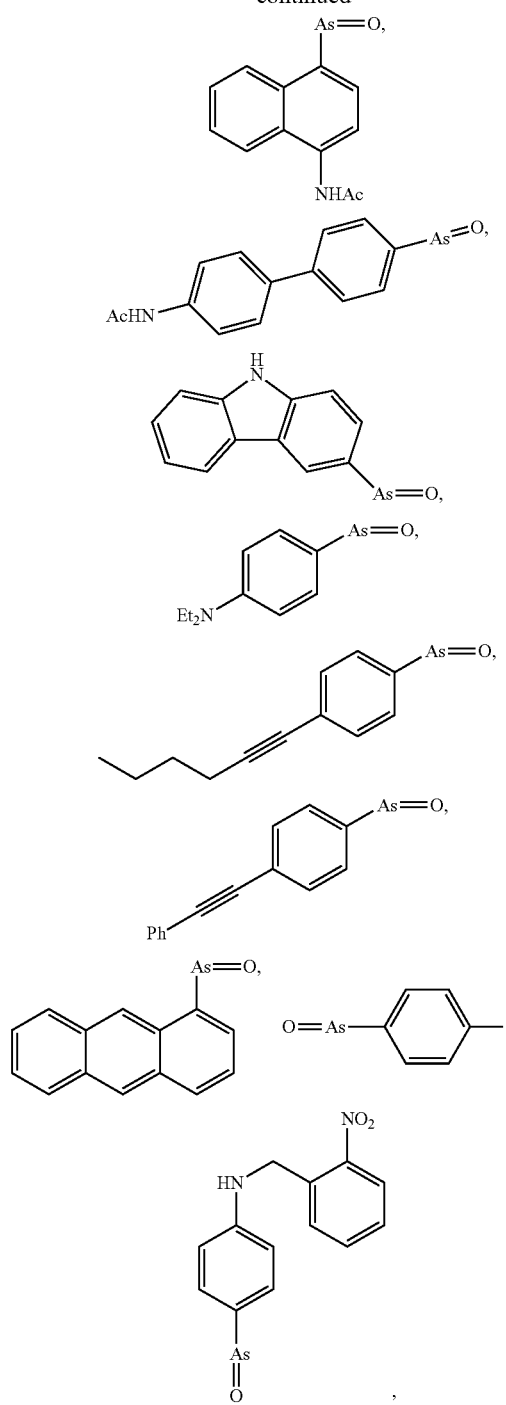
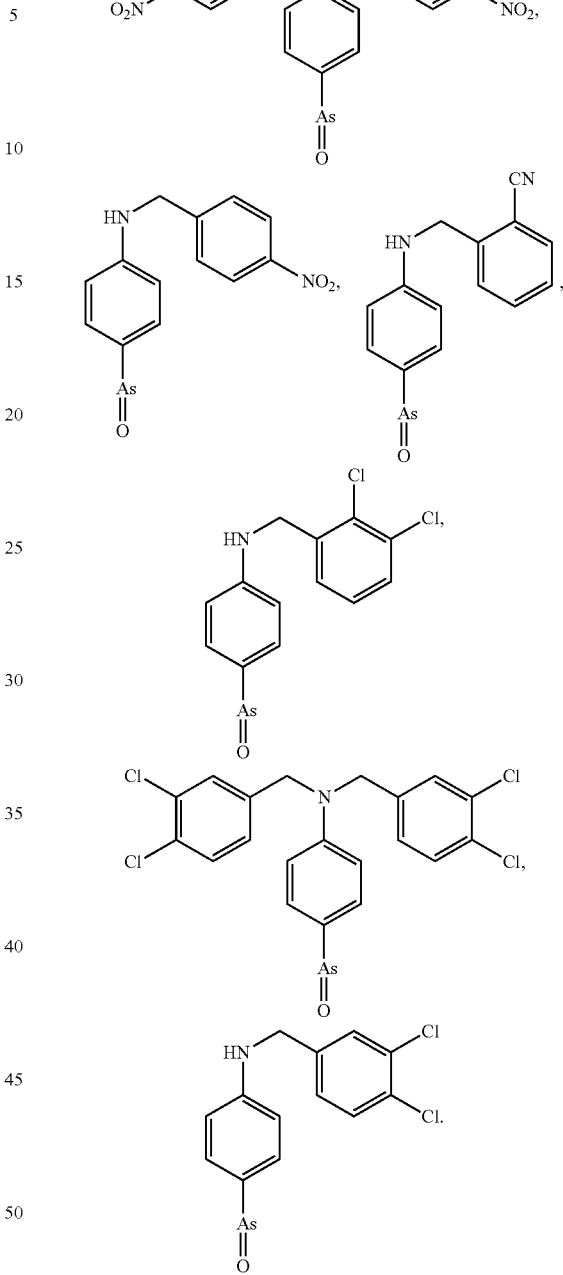
* * * * *

SEQUENCE LISTING

<160> NUMBER OF SEQ ID NOS: 6

<210> SEQ ID NO 1
<211> LENGTH: 65

```
<212> TYPE: PRT
<213> ORGANISM: Drosophila melanogaster

<400> SEQUENCE: 1

Met Ala Ser Lys Val Ser Ile Leu Leu Leu Thr Val His Leu Leu
1               5                   10                  15

Ala Ala Gln Thr Phe Ala Gln Asp Ala Glu Phe Arg His Asp Ser Gly
            20                  25                  30

Tyr Glu Val His His Gln Lys Leu Val Phe Phe Ala Glu Asp Val Gly
        35                  40                  45

Ser Asn Lys Gly Ala Ile Ile Gly Leu Met Val Gly Gly Val Val Ile
    50                  55                  60

Ala
65

<210> SEQ ID NO 2
<211> LENGTH: 24
<212> TYPE: PRT
<213> ORGANISM: Rattus norvegicus

<400> SEQUENCE: 2

Met Ala Gln Phe Leu Arg Leu Cys Ile Trp Leu Leu Ala Leu Gly Ser
1               5                   10                  15

Cys Leu Leu Ala Thr Val Gln Ala
            20

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Lys Arg Ser Asn Arg Ser Lys Arg Leu Gln Tyr Gln Lys Asp Ser Tyr
1               5                   10                  15

Cys

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
aggtatcatt caggttctgt t                                            21

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ggttattgaa attcgaact                                               19

<210> SEQ ID NO 6
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tgctcattag cagtaaaga                                                19
```

UNITED STATES PATENT AND TRADEMARK OFFICE
CERTIFICATE OF CORRECTION

| | |
|---|---|
| PATENT NO. | : 11,766,420 B2 |
| APPLICATION NO. | : 15/570681 |
| DATED | : September 26, 2023 |
| INVENTOR(S) | : Huang et al. |

It is certified that error appears in the above-identified patent and that said Letters Patent is hereby corrected as shown below:

In the Claims

Column 53, Line 13, Claim 1 replace "A method for treating ameliorating or inhibiting" with --A method for ameliorating or inhibiting--.

Signed and Sealed this
Fourteenth Day of November, 2023

Katherine Kelly Vidal
*Director of the United States Patent and Trademark Office*